United States Patent
Demopulos et al.

(10) Patent No.: US 11,628,217 B2
(45) Date of Patent: Apr. 18, 2023

(54) HIGHLY CONCENTRATED LOW VISCOSITY MASP-2 INHIBITORY ANTIBODY FORMULATIONS, KITS, AND METHODS

(71) Applicant: Omeros Corporation, Seattle, WA (US)

(72) Inventors: Gregory A. Demopulos, Mercer Island, WA (US); Kenneth M. Ferguson, Seattle, WA (US); William Joseph Lambert, Seattle, WA (US); John Steven Whitaker, Seattle, WA (US)

(73) Assignee: OMEROS CORPORATION, Seattle, WA (US)

( * ) Notice: Subject to any disclaimer, the term of this patent is extended or adjusted under 35 U.S.C. 154(b) by 0 days.

(21) Appl. No.: 15/691,266

(22) Filed: Aug. 30, 2017

(65) Prior Publication Data

US 2018/0153988 A1    Jun. 7, 2018

Related U.S. Application Data

(60) Provisional application No. 62/382,156, filed on Aug. 31, 2016.

(51) Int. Cl.
| | | |
|---|---|---|
| *A61K 39/395* | (2006.01) | |
| *C07K 16/40* | (2006.01) | |
| *A61K 9/08* | (2006.01) | |
| *A61K 47/12* | (2006.01) | |
| *A61P 25/26* | (2006.01) | |
| *A61K 9/00* | (2006.01) | |
| *A61K 47/18* | (2017.01) | |
| *A61K 47/26* | (2006.01) | |

(52) U.S. Cl.
CPC ........ *A61K 39/3955* (2013.01); *A61K 9/0019* (2013.01); *A61K 9/08* (2013.01); *A61K 47/12* (2013.01); *A61K 47/183* (2013.01); *A61K 47/26* (2013.01); *A61P 25/26* (2018.01); *C07K 16/40* (2013.01); *C07K 2317/94* (2013.01)

(58) Field of Classification Search
None
See application file for complete search history.

(56) References Cited

U.S. PATENT DOCUMENTS

| | | |
|---|---|---|
| 7,390,786 B2 | 6/2008 | Warne et al. |
| 7,919,094 B2 | 4/2011 | Schwaeble et al. |
| 8,652,477 B2 | 2/2014 | Schwaeble et al. |
| 8,840,893 B2 | 9/2014 | Schwaeble et al. |
| 8,951,522 B2 | 2/2015 | Demopulos et al. |
| 9,011,860 B2 | 4/2015 | Dudler et al. |
| 9,644,035 B2 | 5/2017 | Demopulos et al. |
| 10,040,855 B2 * | 8/2018 | Diluzio ................ A61K 9/0019 |
| 2012/0282263 A1 | 5/2012 | Dudler et al. |
| 2013/0266560 A1 | 10/2013 | Demopulos et al. |
| 2013/0344073 A1 | 12/2013 | Schwaeble et al. |
| 2014/0341885 A1 | 11/2014 | Diluzio et al. |
| 2015/0166675 A1 | 6/2015 | Demopulos et al. |
| 2015/0166676 A1 | 6/2015 | Demopulos et al. |
| 2017/0189525 A1 | 7/2017 | Brunskill et al. |
| 2017/0253667 A1 | 9/2017 | Brunskill et al. |
| 2017/0283508 A1 | 10/2017 | Demopulos et al. |

FOREIGN PATENT DOCUMENTS

| | | |
|---|---|---|
| WO | WO 2012/151481 A1 | 11/2012 |
| WO | WO 2014/141149 A1 | 9/2014 |
| WO | WO 2015/058143 A1 | 4/2015 |
| WO | WO 2016/034648 A1 | 3/2016 |
| WO | WO 2016/109822 A1 | 7/2016 |

OTHER PUBLICATIONS

Roos, A., et al., "Glomerular activation of the lectin pathway of complement in IgA nephropathy is associated with more severe renal disease," *J Am Soc Nephrol* 17(6):1724-1734 (2006).
Fitch, C. A., et al., "Arginine: Its pKa value revisited," *Protein Sci* 24(5):752-761 (2015).
Degn, S. E., et al., "Disease-causing mutations in genes of the complement system," *Am J Hum Genet* 88(6):689-705 (2011).
U.S. Appl. No. 15/347,434, Demopulos et al.
U.S. Appl. No. 62/315,857, Demopulos et al.
U.S. Appl. No. 62/275,025, Brunskill et al.
U.S. Appl. No. 62/527,926, Brunskill et al.
Vorup-Jensen, T., et al., "Distinct pathways of mannan-binding lectin (MBL)- and C1-complex autoactivation revealed by reconstitution of MBL with recombinant MBL-associated serine protease-2," *J Immunology* 165:2093-2100 (2000).
Ambrus, G., et al., "Natural substrates and inhibitors of mannan-binding lectin-associated serine protease-1 and -2: A study on recombinant catalytic fragments," *J Immunology* 170:1374-1382 (2003).
Kumura, E., et al., "Coagulation disorders following acute head injury," *Acta Neurochir (Wien)* 85:23-28 (1987).
Zipfel, P.F., et al., "Deletion of complement factor H-related genes CFHR1 and CFHR3 is associated with atypical hemolytic uremic syndrome," *PLoS Genetics* 3(3):0387-0392 (2007).
Schwaeble, W.J., et al., "Targeting of mannan-binding lectin-associated serine protease-2 confers protection from myocardial and gastrointestinal ischemia/reperfusion injury," *PNAS* 108(18):7523-7528 (2011).
Noris, M., et al., "Atypical hemolytic-uremic syndrome," *NEJM* 361(17):1676-87 (2009).
Ricklin, D., et al., "Complement—a key system for immune surveillance and homeostasis," *Nat Immunol* 11(9):785-797 (2010).
Shire, S.J., et al., "Challenges in the development of high protein concentration formulations," *J Pharmaceutical Sciences* 93(6):1390-1402 (2004).
Ho, V.T., et al., "Blood and marrow transplant clinical trials network toxicity committee consensus summary: Thrombotic microangiopathy after hematopoietic stem cell transplantation," *Biology of Blood and Marrow Transplantation* 11:571-575 (2005).

(Continued)

*Primary Examiner* — Yunsoo Kim
(74) *Attorney, Agent, or Firm* — Tineka J. Quinton

(57) ABSTRACT

The present invention relates to stable, high-concentration low-viscosity formulations of MASP-2 inhibitory antibodies, kits comprising the formulations and therapeutic methods using the formulations and kits for inhibiting the adverse effects of MASP-2 dependent complement activation.

28 Claims, 11 Drawing Sheets

Specification includes a Sequence Listing.

(56) References Cited

OTHER PUBLICATIONS

Wyatt, R.J., et al., "IgA nephropathy," *NEJM* 368(25):2402-14 (2013).
Goto, M., et al., "A scoring system to predict renal outcome in IgA nephropathy: a nationwide 10-year prospective cohort study," *Nephrol Dial Transplant* 24:3068-3074 (2009).
Berthoux, F., et al., "Predicting the risk for dialysis or death in IgA nephropathy," *J Am Soc Nephrol* 22:752-761 (2011).
Coppo, R., et al., "Factors predicting progression of IgA nephropathies," *J Nephrol* 18:503-512 (2005).
Reich, H.N., et al., "Remission of proteinuria improves prognosis in IgA nephropathy," *J Am Soc Nephrol* 18:3177-3183 (2007).
D'Amico, G., "Natural history of idiopathic IgA nephropathy: Role of critical and histological prognostic factors," *Am J Kid Dis* 36(2):227-237 (2000).
Pisetsky, D.S., et al., "Systemic lupus erythematosus," *Med Clin North America* 81(1):113-128 (1997).
Burckbuchler, V., et al., "Rheological and syringeability properties of highly concentrated human polyclonal immunoglobulin solutions," *Eur J Pharmaceut Biopharmaceut* 76:351-356 (2010).
Cilurzo, F., et al., "Injectability evaluations: An open issue," *AAPS PharmaSciTech* 12(2):604-609 (2011).
Sukumar, M., et al., "Opalescent appearance of an IgG1 antibody at high concentrations and its relationship to noncovalent association," *Pharmaceutical Research* 21(7):1087-1093 (2004).
Salinas, B.A., et al., "Buffer-dependent fragmentation of a humanized full-length monoclonal antibody," *J Pharm Sci* 99(7):2962-2974 (2010).
Alford, J.R., et al., "High concentration formulations of recombinant human interleukin-1 receptor antagonist: II. Aggregation kinectics," *J Pharmaceutical Sciences* 97(8):3005-3021 (2008).
Wang, W., et al., "Anibody structure, instability, and formulation," *J Pharmaceutical Sciences* 96(1):1-26 (2007).
Stockwin, L.H., et al., "Antibodies as therapeutic agents: vive la renaissance!" *Expert Opin Biol Ther* 3(7):1133-1152 (2003).
Connolly, B.D., et al., "Weak interactions govern the viscosity of concentrated antibody solutions: High-throughput analysis using the diffusion interaction parameter," *Biophysical Journal* 103:69-78 (2012).
Koda-Kimble and Youngs Applied Therapeutics, 10th Edition, Section 5, pp. 792-799, 2012. Brian K. Alldredge, Editor, Wolters Kluwer—Lippincott Williams 7 Wilkins, Publisher.
Overcashier, D.E., et al., "Technical considerations in the development of prefilled syringes for protein products," *Am Pharmecutical Review* 9(6):77-83 (2006).

\* cited by examiner

SEQUENCE LISTING

```
<160> NUMBER OF SEQ ID NOS: 7

<210> SEQ ID NO 1
<211> LENGTH: 671
<212> TYPE: PRT
<213> ORGANISM: Homo sapiens

<400> SEQUENCE: 1

Thr Pro Leu Gly Pro Lys Trp Pro Glu Pro Val Phe Gly Arg Leu Ala
1               5                  10                  15

Ser Pro Gly Phe Pro Gly Glu Tyr Ala Asn Asp Gln Glu Arg Arg Trp
            20                  25                  30

Thr Leu Thr Ala Pro Pro Gly Tyr Arg Leu Arg Leu Tyr Phe Thr His
        35                  40                  45

Phe Asp Leu Glu Leu Ser His Leu Cys Glu Tyr Asp Phe Val Lys Leu
    50                  55                  60
```

```
Ser Ser Gly Ala Lys Val Leu Ala Thr Leu Cys Gly Gln Glu Ser Thr
 65                  70                  75                  80

Asp Thr Glu Arg Ala Pro Gly Lys Asp Thr Phe Tyr Ser Leu Gly Ser
                 85                  90                  95

Ser Leu Asp Ile Thr Phe Arg Ser Asp Tyr Ser Asn Glu Lys Pro Phe
                100                 105                 110

Thr Gly Phe Glu Ala Phe Tyr Ala Ala Glu Asp Ile Asp Glu Cys Gln
            115                 120                 125

Val Ala Pro Gly Glu Ala Pro Thr Cys Asp His His Cys His Asn His
130                 135                 140

Leu Gly Gly Phe Tyr Cys Ser Cys Arg Ala Gly Tyr Val Leu His Arg
145                 150                 155                 160

Asn Lys Arg Thr Cys Ser Ala Leu Cys Ser Gly Gln Val Phe Thr Gln
                165                 170                 175

Arg Ser Gly Glu Leu Ser Ser Pro Glu Tyr Pro Arg Pro Tyr Pro Lys
                180                 185                 190

Leu Ser Ser Cys Thr Tyr Ser Ile Ser Leu Glu Glu Gly Phe Ser Val
                195                 200                 205

Ile Leu Asp Phe Val Glu Ser Phe Asp Val Glu Thr His Pro Glu Thr
210                 215                 220

Leu Cys Pro Tyr Asp Phe Leu Lys Ile Gln Thr Asp Arg Glu Glu His
225                 230                 235                 240

Gly Pro Phe Cys Gly Lys Thr Leu Pro His Arg Ile Glu Thr Lys Ser
                245                 250                 255

Asn Thr Val Thr Ile Thr Phe Val Thr Asp Glu Ser Gly Asp His Thr
                260                 265                 270

Gly Trp Lys Ile His Tyr Thr Ser Thr Ala Gln Pro Cys Pro Tyr Pro
                275                 280                 285

Met Ala Pro Pro Asn Gly His Val Ser Pro Val Gln Ala Lys Tyr Ile
290                 295                 300

Leu Lys Asp Ser Phe Ser Ile Phe Cys Glu Thr Gly Tyr Glu Leu Leu
305                 310                 315                 320

Gln Gly His Leu Pro Leu Lys Ser Phe Thr Ala Val Cys Gln Lys Asp
                325                 330                 335

Gly Ser Trp Asp Arg Pro Met Pro Ala Cys Ser Ile Val Asp Cys Gly
                340                 345                 350

Pro Pro Asp Asp Leu Pro Ser Gly Arg Val Glu Tyr Ile Thr Gly Pro
                355                 360                 365

Gly Val Thr Thr Tyr Lys Ala Val Ile Gln Tyr Ser Cys Glu Glu Thr
                370                 375                 380

Phe Tyr Thr Met Lys Val Asn Asp Gly Lys Tyr Val Cys Glu Ala Asp
385                 390                 395                 400

Gly Phe Trp Thr Ser Ser Lys Gly Glu Lys Ser Leu Pro Val Cys Glu
                405                 410                 415

Pro Val Cys Gly Leu Ser Ala Arg Thr Thr Gly Gly Arg Ile Tyr Gly
                420                 425                 430

Gly Gln Lys Ala Lys Pro Gly Asp Phe Pro Trp Gln Val Leu Ile Leu
                435                 440                 445

Gly Gly Thr Thr Ala Ala Gly Ala Leu Leu Tyr Asp Asn Trp Val Leu
                450                 455                 460

Thr Ala Ala His Ala Val Tyr Glu Gln Lys His Asp Ala Ser Ala Leu
465                 470                 475                 480
```

```
Asp Ile Arg Met Gly Thr Leu Lys Arg Leu Ser Pro His Tyr Thr Gln
                485                 490                 495

Ala Trp Ser Glu Ala Val Phe Ile His Glu Gly Tyr Thr His Asp Ala
            500                 505                 510

Gly Phe Asp Asn Asp Ile Ala Leu Ile Lys Leu Asn Asn Lys Val Val
            515                 520                 525

Ile Asn Ser Asn Ile Thr Pro Ile Cys Leu Pro Arg Lys Glu Ala Glu
530                 535                 540

Ser Phe Met Arg Thr Asp Asp Ile Gly Thr Ala Ser Gly Trp Gly Leu
545                 550                 555                 560

Thr Gln Arg Gly Phe Leu Ala Arg Asn Leu Met Tyr Val Asp Ile Pro
                565                 570                 575

Ile Val Asp His Gln Lys Cys Thr Ala Ala Tyr Glu Lys Pro Pro Tyr
            580                 585                 590

Pro Arg Gly Ser Val Thr Ala Asn Met Leu Cys Ala Gly Leu Glu Ser
            595                 600                 605

Gly Gly Lys Asp Ser Cys Arg Gly Asp Ser Gly Gly Ala Leu Val Phe
            610                 615                 620

Leu Asp Ser Glu Thr Glu Arg Trp Phe Val Gly Gly Ile Val Ser Trp
625                 630                 635                 640

Gly Ser Met Asn Cys Gly Glu Ala Gly Gln Tyr Gly Val Tyr Thr Lys
                645                 650                 655

Val Ile Asn Tyr Ile Pro Trp Ile Glu Asn Ile Ile Ser Asp Phe
                660                 665                 670

<210> SEQ ID NO 2
<211> LENGTH: 118
<212> TYPE: PRT
<213> ORGANISM: Artificial Sequence
<220> FEATURE:
<223> OTHER INFORMATION: Synthetic

<400> SEQUENCE: 2

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Arg Gly
                20                  25                  30

Lys Met Gly Val Ser Trp Ile Arg Gln Pro Pro Gly Lys Ala Leu Glu
            35                  40                  45

Trp Leu Ala His Ile Phe Ser Ser Asp Glu Lys Ser Tyr Arg Thr Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Arg Arg Gly Gly Ile Asp Tyr Trp Gly Gln Gly Thr
            100                 105                 110

Leu Val Thr Val Ser Ser
        115

<210> SEQ ID NO 3
<211> LENGTH: 103
<212> TYPE: PRT
<213> ORGANISM: Artificial Sequence
<220> FEATURE:
<223> OTHER INFORMATION: Synthetic
```

-continued

<400> SEQUENCE: 3

```
Gln Pro Val Leu Thr Gln Pro Pro Ser Leu Ser Val Ser Pro Gly Gln
1               5                   10                  15

Thr Ala Ser Ile Thr Cys Ser Gly Glu Lys Leu Gly Asp Lys Tyr Ala
            20                  25                  30

Tyr Trp Tyr Gln Gln Lys Pro Gly Gln Ser Pro Val Leu Val Met Tyr
        35                  40                  45

Gln Asp Lys Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu
            100
```

<210> SEQ ID NO 4
<211> LENGTH: 445
<212> TYPE: PRT
<213> ORGANISM: Artificial Sequence
<220> FEATURE:
<223> OTHER INFORMATION: Synthetic

<400> SEQUENCE: 4

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Arg Gly
            20                  25                  30

Lys Met Gly Val Ser Trp Ile Arg Gln Pro Pro Gly Lys Ala Leu Glu
        35                  40                  45

Trp Leu Ala His Ile Phe Ser Ser Asp Glu Lys Ser Tyr Arg Thr Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Arg Arg Gly Gly Ile Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 5
<211> LENGTH: 212
<212> TYPE: PRT
<213> ORGANISM: Artificial Sequence
<220> FEATURE:
<223> OTHER INFORMATION: Synthetic

<400> SEQUENCE: 5

Gln Pro Val Leu Thr Gln Pro Pro Ser Leu Ser Val Ser Pro Gly Gln
1               5                   10                  15

Thr Ala Ser Ile Thr Cys Ser Gly Glu Lys Leu Gly Asp Lys Tyr Ala
            20                  25                  30

Tyr Trp Tyr Gln Gln Lys Pro Gly Gln Ser Pro Val Leu Val Met Tyr
        35                  40                  45

Gln Asp Lys Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160
```

Thr Thr Thr Pro Ser Lys Gln Ser Asn Asn Lys Tyr Ala Ala Ser Ser
            165                 170                 175

Tyr Leu Ser Leu Thr Pro Glu Gln Trp Lys Ser His Arg Ser Tyr Ser
        180                 185                 190

Cys Gln Val Thr His Glu Gly Ser Thr Val Glu Lys Thr Val Ala Pro
        195                 200                 205

Thr Glu Cys Ser
    210

<210> SEQ ID NO 6
<211> LENGTH: 1395
<212> TYPE: DNA
<213> ORGANISM: Artificial sequence
<220> FEATURE:
<223> OTHER INFORMATION: Synthetic

<400> SEQUENCE: 6

```
atgatgtcct ttgtctctct gctcctggtt ggcatcctat tccatgccac ccaggcccag      60
gtcaccttga aggagtctgg tcctgtgctg gtgaaaccca cagagaccct cacgctgacc     120
tgcaccgtct ctgggttctc actcagcagg gtaaaatgg gtgtgagctg atccgtcag      180
cccccaggga aggccctgga gtggcttgca cacatttttt cgagtgacga aaaatcctac     240
aggacatcgc tgaagagcag gctcaccatc tccaaggaca cctccaaaaa ccaggtggtc     300
cttacaatga ccaacatgga ccctgtggac acagccacgt attactgtgc acggatacga     360
cgtggaggaa ttgactactg gggccaggga accctggtca ctgtctcctc agcctccacc     420
aagggcccat ccgtcttccc cctggcgccc tgctccagga gcacctccga gagcacagcc     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacgaagac ctacacctgc     660
aacgtagatc acaagcccag caacaccaag gtggacaaga gagttgagtc caaatatggt     720
cccccatgcc caccatgccc agcacctgag ttcctggggg gaccatcagt cttcctgttc     780
cccccaaaaac ccaaggacac tctcatgatc tcccggaccc ctgaggtcac gtgcgtggtg     840
gtggacgtga gccaggaaga ccccgaggtc cagttcaact ggtacgtgga tggcgtggag     900
gtgcataatg ccaagacaaa gccgcgggag gagcagttca acagcacgta ccgtgtggtc     960
agcgtcctca ccgtcctgca ccaggactgg ctgaacggca aggagtacaa gtgcaaggtc    1020
tccaacaaag gctcccgtc ctccatcgag aaaaccatct ccaaagccaa agggcagccc    1080
cgagagccac aggtgtacac cctgccccca tcccaggagg agatgaccaa gaaccaggtc    1140
agcctgacct gcctggtcaa aggcttctac cccagcgaca tcgccgtgga gtgggagagc    1200
aatgggcagc cggagaacaa ctacaagacc acgcctcccg tgctggactc cgacggctcc    1260
ttcttcctct acagcaggct aaccgtggac aagagcaggt ggcaggaggg gaatgtcttc    1320
tcatgctccg tgatgcatga ggctctgcac aaccactaca cacagaagag cctctccctg    1380
tctctcggga aatga                                                    1395
```

<210> SEQ ID NO 7
<211> LENGTH: 696
<212> TYPE: DNA
<213> ORGANISM: Artificial sequence
<220> FEATURE:
<223> OTHER INFORMATION: Synthetic
<220> FEATURE:
<221> NAME/KEY: misc_feature

```
<222> LOCATION: (303)..(303)
<223> OTHER INFORMATION: n is a, c, g, or t

<400> SEQUENCE: 7
atgatgtcct ttgtctctct gctcctggtt ggcatcctat tccatgccac ccaggcccag      60
ccagtgctga ctcagccccc ctcactgtcc gtgtccccag gacagacagc cagcatcacc     120
tgctctggag agaaattggg ggataaatat gcttactggt atcagcagaa gccaggccag     180 tccctgtgt  tggtcatgta tcaagataaa cagcggccct cagggatccc tgagcgattc     240
tctggctcca actctgggaa cacagccact ctgaccatca gcgggaccca ggctatggat     300
gangctgact attactgtca ggcgtgggac agcagcactg cggtattcgg cggagggacc     360
aagctgaccg tcctaggcca gcctaaggcg gcgccctcgg tcaccctgtt cccgccctcc     420
tctgaggagc ttcaagccaa caaggccaca ctggtgtgtc tcataagtga cttctacccg     480
ggagccgtga cagtggcctg gaaggcagat agcagccccg tcaaggcggg agtggagacc     540
accacaccct ccaaacaaag caacaacaag tacgcggcca gcagctatct gagcctgacg     600
cctgagcagt ggaagtccca cagaagctac agctgccagg tcacgcatga agggagcacc     660
gtggagaaga cagtggcccc tacagaatgt tcatag                               696
```

HIGHLY CONCENTRATED LOW VISCOSITY MASP-2 INHIBITORY ANTIBODY FORMULATIONS, KITS, AND METHODS

CROSS-REFERENCE TO RELATED APPLICATIONS

This application claims the benefit of U.S. Provisional Application No. 62/382,156, filed Aug. 31, 2016, which is hereby incorporated by reference in its entirety.

FIELD OF THE INVENTION

The present invention relates to stable, high-concentration low-viscosity formulations of MASP-2 inhibitory antibodies, kits comprising the formulations and therapeutic methods using the formulations and kits for inhibiting the adverse effects of MASP-2 dependent complement activation.

STATEMENT REGARDING SEQUENCE LISTING

The sequence listing associated with this application is provided in text format in lieu of a paper copy and is hereby incorporated by reference into the specification. The name of the text file containing the sequence listing is MP_1_0261_US_20170809_ST25.txt. The text file is 17 KB; was created on Aug. 9, 2017; and is being submitted via EFS-Web with the filing of the specification.

BACKGROUND

Antibody-based therapy is usually administered on a regular basis and often requires several mg/kg dosing by injection. A preferred form of delivery for treating chronic conditions is outpatient administration of high-dose monoclonal antibodies (several mg per kg) via subcutaneous (SC) injection (Stockwin and Holmes, *Expert Opin Biol Ther* 3:1133-1152 (2003); Shire et al., *J Pharm Sci* 93:1390-1402 (2004)). Highly concentrated pharmaceutical formulations of a therapeutic antibody are desirable because they allow lower volume administration and/or fewer administrations which consequently mean less discomfort to the patient. Additionally, such lower volumes allow packaging of the therapeutic doses of a monoclonal antibody in individual single-dose, pre-filled syringes for self-administration. SC delivery via pre-filled syringe or auto-injector technology allows for home administration and improved patient compliance of drug administration.

However, the development of a formulation with a high protein concentration poses challenges related to the physical and chemical stability of the protein, as well as difficulty with manufacture, storage and delivery of the protein formulation (see e.g., Wang et al., *J of Pharm Sci* vol 96(1): 1-26, (2007)). A challenge in the development of high protein concentration formulations is concentration-dependent solution viscosity. At a given protein concentration, viscosity varies dramatically as a function of the formulation. In particular, monoclonal antibodies are known to exhibit peculiar and diverse viscosity-concentration profiles that reveal a sharp exponential increase in solution viscosity with increasing monoclonal antibody concentration (see e.g., Connolly B. D. et al., *Biophysical Journal* vol 103:69-78, (2012)). Another challenge with liquid formulations at high monoclonal antibody concentration is protein physical stability (Alford et al., *J. Pharm Sci* 97:3005-3021 (2008); Salinas et al., *J Pharm Sci* 99:82-93 (2010); Sukumar et al., *Pharm Res* 21:1087-1093 (2004)). Therefore, the high viscosity of monoclonal antibody pharmaceutical formulations at high concentrations together with the potential for decreased stability can impede their development as products suitable for subcutaneous and/or intravenous delivery.

The complement system plays a role in the inflammatory response and becomes activated as a result of tissue damage or microbial infection. Complement activation must be tightly regulated to ensure selective targeting of invading microorganisms and avoid self-inflicted damage (Ricklin et al., *Nat. Immunol.* 11:785-797, 2010). Currently, it is widely accepted that the complement system can be activated through three distinct pathways: the classical pathway, the lectin pathway, and the alternative pathway. The classical pathway is usually triggered by a complex composed of host antibodies bound to a foreign particle (i.e., an antigen) and generally requires prior exposure to an antigen for the generation of a specific antibody response. Since activation of the classical pathway depends on a prior adaptive immune response by the host, the classical pathway is part of the acquired immune system. In contrast, both the lectin and alternative pathways are independent of adaptive immunity and are part of the innate immune system.

Mannan-binding lectin-associated serine protease-2 (MASP-2) has been shown to be required for the function of the lectin pathway, one of the principal complement activation pathways (Vorup-Jensen et al., *J. Immunol* 165:2093-2100, 2000; Ambrus et al., *J Immunol.* 170:1374-1382, 2003; Schwaeble et al., *PNAS* 108:7523-7528, 2011). Importantly, inhibition of MASP-2 does not appear to interfere with the antibody-dependent classical complement activation pathway, which is a critical component of the acquired immune response to infection. As described in U.S. Pat. No. 9,011,860 (assigned to Omeros corporation), which is hereby incorporated by reference, OMS646, a fully human monoclonal antibody targeting human MASP-2 has been generated which binds to human MASP-2 with high affinity and blocks the lectin pathway complement activity and is therefore useful to treat various lectin complement pathway-associated diseases and disorders.

As further described in U.S. Pat. Nos. 7,919,094, 8,840,893, 8,652,477, 8,951,522, 9,011,860; 9,644,035, U.S. Patent Application Publication Nos. US2013/0344073, US2013/0266560, US 2015/0166675; US2017/0189525; and co-pending U.S. patent application Ser. Nos. 15/476,154, 15/347,434, 15/470,647, 62/315,857, 62/275,025 and 62/527,926 (each of which is assigned to Omeros Corporation, the assignee of the instant application, each of which is hereby incorporated by reference), MASP-2-dependent complement activation has been implicated as contributing to the pathogenesis of numerous acute and chronic disease states. Therefore, a need exists for a stable, high-concentration, low-viscosity formulation of a MASP-2 monoclonal antibody that is suitable for parenteral (e.g., subcutaneous) administration, for treatment of subject suffering from MASP-2 complement pathway-associated diseases and disorders.

SUMMARY

In one aspect, the present disclosure provides a stable pharmaceutical formulation suitable for parenteral administration to a mammalian subject, comprising: (a) an aqueous solution comprising a buffer system having a pH of 5.0 to 7.0; and (b) a monoclonal antibody or fragment thereof that specifically binds to human MASP-2 at a concentration of about 50 mg/mL to about 250 mg/mL, wherein said antibody or fragment thereof comprises (i) a heavy chain variable region comprising CDR-H1, CDR-H2 and CDR-H3 of SEQ ID NO:2 and (ii) a light chain variable region comprising CDR-L1, CDR-L2 and CDR-L3 of SEQ ID NO:3, or a variant thereof comprising a heavy chain variable region having at least 95% identity to SEQ ID NO:2 and a light chain variable region having at least 95% identity to SEQ ID NO:3; wherein the formulation has a viscosity of between 2 and 50 centipoise (cP), and wherein the formulation is stable when stored at between 2° C. and 8° C. for at least one month. In some embodiments, the concentration of the antibody in the formulation is from about 150 mg/mL to about 200 mg/mL. In some embodiments, the viscosity of the formulation less than 25 cP. In some embodiments, the buffering system comprises histidine. In some embodiments, the buffering system comprises citrate. In some embodiments, the formulation further comprises an excipient, such as a tonicity modifying agent in a sufficient amount for the formulation to be hypertonic. In some embodiments, the formulation further comprises a surfactant. In some embodiments, the formulation further comprises a hyaluronidase enzyme in an amount effective to increase the dispersion and/or absorption of the antibody following subcutaneous administration.

In another aspect, the formulation is contained within a subcutaneous administration device, such as a pre-filled syringe.

In another aspect, the present disclosure provides a kit comprising a pre-filled container containing the formulation.

In another aspect, the present disclosure provides a pharmaceutical composition for use in treating a patient suffering from, or at risk for developing a MASP-2-dependent disease or condition, wherein the composition is a sterile, single-use dosage form comprising from about 350 mg to about 400 mg (i.e., 350 mg, 360 mg, 370 mg, 380 mg, 390 mg, or 400 mg) of MASP-2 inhibitory antibody, wherein the composition comprises about 1.8 mL to about 2.2 mL (i.e., 1.8 mL, 1.9 mL, 2.0 mL, 2.1 mL or 2.2 mL) of a 185 mg/mL antibody formulation, such as disclosed herein, wherein said antibody or fragment thereof comprises (i) a heavy chain variable region comprising the amino acid sequence set forth in SEQ ID NO:2 and (ii) a light chain variable region comprising the amino acid sequence set forth in SEQ ID NO:3; and wherein the formulation is stable when stored at between 2° C. and 8° C. for at least six months. In some embodiments, the MASP-2 dependent disease or condition is selected from the group consisting of aHUS, HSCT-TMA, IgAN and Lupus Nephritis (LN).

In another aspect, the present disclosure provides a method of treating a subject suffering from a disease or disorder amenable to treatment with a MASP-2 inhibitory antibody comprising administering the formulation comprising a MASP-2 antibody, as disclosed herein.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DESCRIPTION OF THE SEQUENCE LISTING

Figure 1A:
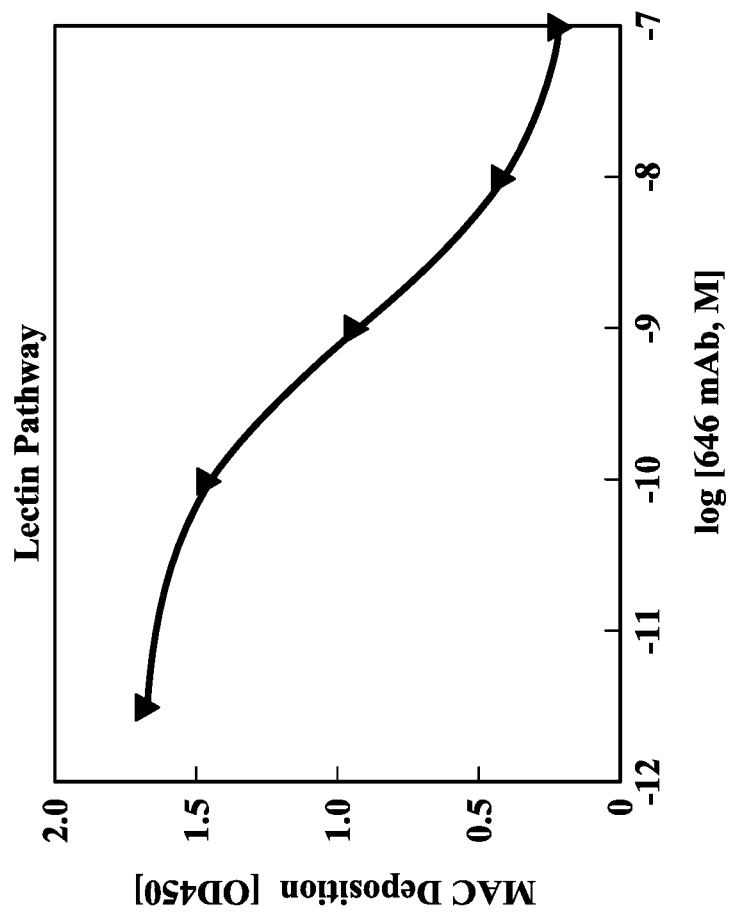
FIG. 1A graphically illustrates the amount of lectin pathway-dependent membrane attack complex (MAC) deposition in the presence of different amounts of human MASP-2 monoclonal antibody (OMS646), demonstrating that OMS646 inhibits lectin-mediated MAC deposition with an $IC_{50}$ value of approximately 1 nM, as described in Example 1.

SEQ ID NO:1 human MASP-2 protein (mature)
SEQ ID NO:2: OMS646 heavy chain variable region (VH) polypeptide
SEQ ID NO:3: OMS646 light chain variable region (VL) polypeptide
SEQ ID NO:4: OMS646 heavy chain IgG4 mutated heavy chain full length polypeptide
SEQ ID NO:5: OMS646 light chain full length polypeptide
SEQ ID NO:6: DNA encoding OMS646 full length heavy chain polypeptide
SEQ ID NO:7: DNA encoding OMS646 full length light chain polypeptide.

DETAILED DESCRIPTION

I. Definitions

Unless specifically defined herein, all terms used herein have the same meaning as would be understood by those of ordinary skill in the art of the present invention. The following definitions are provided in order to provide clarity with respect to the terms as they are used in the specification and claims to describe the present invention.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y.; Current Protocols in Molecular Biology (Greene Publ. Assoc. Inc. & John Wiley & Sons, Inc., NY, NY); Current Protocols in Immunology (Edited by: John E. Coligan, Ada M. Kruisbeek, David H. Margulies, Ethan M. Shevach, Warren Strober 2001 John Wiley & Sons, NY, NY); or other relevant Current Protocol publications and other like references. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

The term "pharmaceutical formulation" refers to a preparation that is in such form as to permit the biological activity of the active agent (e.g., MASP-2 inhibitory antibody) to be effective for treatment, and which contains no additional components that are unacceptably toxic to a subject in which the formulation would be administered. Such formulations are sterile. In one embodiment, the pharmaceutical formulation is suitable for parenteral administration, such as subcutaneous administration.

The term "MASP-2" refers to mannan-binding lectin-associated serine protease-2. Human MASP-2 protein (mature) is set forth as SEQ ID NO:1.

The term "MASP-2-dependent complement activation" comprises MASP-2-dependent activation of the lectin pathway, which occurs under physiological conditions (i.e., in the presence of $Ca^{++}$) leading to the formation of the lectin pathway C3 convertase C4b2a and upon accumulation of the C3 cleavage product C3b subsequently to the C5 convertase C4b2a(C3b)n.

The term "lectin pathway" refers to complement activation that occurs via the specific binding of serum and non-serum carbohydrate-binding proteins including mannan-binding lectin (MBL), CL-11 and the ficolins (H-ficolin, M-ficolin, or L-ficolin).

The term "classical pathway" refers to complement activation that is triggered by an antibody bound to a foreign particle and requires binding of the recognition molecule C1q.

The term "MASP-2 inhibitory antibody" refers to an antibody, or antigen binding fragment thereof, that binds to MASP-2 and effectively inhibits MASP-2-dependent complement activation (e.g., OMS646). MASP-2 inhibitory antibodies useful in the method of the invention may reduce MASP-2-dependent complement activation by greater than 20%, such as greater than 30%, or greater than 40%, or greater than 50%, or greater than 60%, or greater than 70%, or greater than 80%, or greater than 90%, or greater than 95%.

The term "OMS646 monoclonal antibody" refers to a monoclonal antibody comprising CDR-H1, CDR-H2 and CDR-H3 of the heavy chain variable region amino acid sequence set forth in SEQ ID NO:2 and comprising CDR-L1, CDR-L2 and CDR-L3 of the light chain variable region amino acid sequence set forth in SEQ ID NO:3. This particular antibody is an example of a MASP-2 inhibitory antibody that specifically binds to MASP-2 and inhibits MASP-2 dependent complement activation.

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific for the target antigen. The term "monoclonal antibody" encompasses not only intact monoclonal antibodies and full-length monoclonal antibodies, but also fragments thereof (such as Fab, Fab', F(ab')2, Fv), single chain (scFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody".

The term "antibody fragment" refers to a portion derived from or related to a full-length antibody, such as, for example, a MASP-2 inhibitory antibody, generally including the antigen binding or variable region thereof. Illustrative examples of antibody fragments include Fab, Fab', $F(ab)_2$, $F(ab')_2$ and Fv fragments, scFv fragments, diabodies, linear antibodies, single-chain antibody molecules and multispecific antibodies formed from antibody fragments.

As used herein, a "single-chain Fv" or "scFv" antibody fragment comprises the $V_H$ and $V_L$ domains of an antibody, wherein these domains are present in a single polypeptide chain. Generally, the Fv polypeptide further comprises a polypeptide linker between the $V_H$ and $V_L$ domains, which enables the scFv to form the desired structure for antigen binding.

The term "CDR region" or "CDR" is intended to indicate the hypervariable regions of the heavy and light chains of the immunoglobulin as defined by Kabat et al., 1991 (Kabat, E. A. et al., (1991) Sequences of Proteins of Immunological Interest, 5$^{th}$ Edition and later editions. An antibody typically contains 3 heavy chain CDRs and 3 light chain CDRs. The term CDR or CDRs is used here in order to indicate, according to the case, one of these regions, or several, or even the whole, of these regions which contain the majority of the amino acid residues responsible for the binding by affinity of the antibody for the antigen of the epitope which it recognizes.

The term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold). In certain embodiments, the affinity between a capture agent and analyte when they are specifically bound in a capture agent/analyte complex is characterized by a $K_D$ (dissociation constant) of less than about 100 nM, or less than about 50 nM, or less than about 25 nM, or less than about 10 nM, or less than about 5 nM, or less than about 1 nM.

The term "isolated antibody" refers to an antibody that has been identified and separated and/or recovered and/or purified from a component of its natural environment or cell culture expression system. In preferred embodiments, the antibody will be purified (1) to greater than 95% by weight of antibody and most preferably more than 99% by weight; as determined by a suitable method to measure protein concentration, such as, for example, the Lowry method, or absorbance at OD280, (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Typically an isolated antibody for use in the formulations disclosed herein will be prepared by at least one purification step.

As used herein, the amino acid residues are abbreviated as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (Hush), isoleucine (Ilia), leucine (Lull), lysine (Lys;K), methionine (Met;M), phenylalanine (Phe;F), proline (Pro; P), serine (Ser;S), threonine (Thr;T), tryptophan (Trp;W), tyrosine (Tyr;Y), and valine (Val;V).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further subclassed as follows. By "uncharged hydrophilic" amino acid is meant either Ser, Thr, Asn or Gln. By "acidic" amino acid is meant either Glu or Asp. By "basic" amino acid is meant either Lys, Arg or His.

As used herein the term "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

As used herein, "a subject" includes all mammals, including without limitation, humans, non-human primates, dogs, cats, horses, sheep, goats, cows, rabbits, pigs and rodents.

The term "pharmaceutically acceptable" with respect to an excipient in a pharmaceutical formulation means that the excipient is suitable for administration to a human subject.

The term "subcutaneous administration" refers to administration of a formulation under all layers of the skin of a subject.

The term "buffer" refers to a buffered solution that resists changes in pH by the action of its acid-base conjugate components. The buffer of this invention has a pH in the range from about 4 to about 8; preferably from about 5 to about 7; and most preferably has a pH in the range from about 5.5 to about 6.5. Examples of buffers that will control the pH in this range include acetate (e.g., sodium acetate), succinate (such as sodium succinate), gluconate, histidine, citrate, and other organic acid buffers. A "buffering agent" is a compound that is used to produce buffered solutions.

The term "histidine" specifically includes L-histidine unless otherwise specified. The term "isotonic" refers to a formulation that has essentially the same osmotic pressure as human blood. Isotonic formulations will generally have an osmotic pressure from about 250 to about 350 mOsmol/KgH$_2$O. Isotonicity can be measured using a vapor pressure or freezing point depression osmometer, for example.

The term "hypertonic" refers to a formulation with an osmotic pressure above that of human (i.e., greater than 350 mOsm/KgH$_2$O).

The term "tonicity modifying agent" refers to a pharmaceutically acceptable agent suitable to provide an isotonic, or in some embodiments, a hypertonic formulation.

The term "sterile" refers to a pharmaceutical product that is aseptic or free of viable bacteria, fungi or other microorganisms, which can be achieved by any suitable means, such as, for example, a formulation that has been aseptically processed and filled, or filtered through sterile filtration membranes, prior to, or following, preparation of the formulation and filled.

The term "stable formulation" refers to maintenance of the starting level of purity of a formulation over a period of time. In other words, if a formulation is at least 95% pure, such as at least 96% pure, at least 97% pure, at least 98% pure or at least 99% pure with respect to a given antibody species (e.g., MASP-2 inhibitory antibody) at time 0, stability is a measure of how well and for how long the formulation retains substantially this level of purity (e.g., without formation of other species, such as fragmented portions (LMW) or aggregates of the pure species (HMW)). A formulation is stable if the level of purity does not decrease substantially when stored at approximately 2-8° C. over a given period of time, such as at least 6 months, at least 9 months, at least 12 months, or at least 24 months. By "not decrease substantially," is meant that the level of purity of the formulation changes by less than 5%, such as by less than 4%, or by less than 3%, or by less than 2% or by less than 1% per time period (e.g., over 6 months, over 9 months or over 12 months or over 24 months). In one embodiment, a stable formulation is stable at a temperature of from 2-8° C. for a period of at least six months. In a preferred embodiment, a stable formulation is stable at a temperature of from 2-8° C. for a period of at least one year, or for a period of at least two years. In one embodiment, the formulation is stable if the MASP-2 inhibitory antibody remains at least 95% monomeric during storage at 2° C. to 8° C. for at least one month, or for at least six months, or for at least 12 months, as determined by SEC-HPLC.

The term "preservative" refers to a compound which can be included in a formulation to essentially reduce bacterial growth or contamination. Non-limiting examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

The term "excipient" refers to an inert substance in a formulation which imparts a beneficial physical property to a formulation such as increased protein stability and/or decreased viscosity. Examples of suitable excipients include, but are not limited to, proteins (e.g., serum albumin), amino acids (e.g., aspartic acid, glutamic acid, lysine arginine, glycine and histidine), saccharides (e.g., glucose, sucrose, maltose and trehalose), polyols (e.g., mannitol and sorbitol), fatty acids and phospholipids (e.g., alkyl sulfonates and caprylate).

The term "substantially free" means that either no substance is present or only minimal, trace amounts of the substance are present which do not have any substantial impact on the properties of the composition. If reference is made to no amount of a substance, it should be understood as "no detectable amount."

The term "viscosity" refers to the measure of the resistance of a fluid which is being deformed by either shear stress or tensile stress; it can be evaluated using a viscometer (e.g., a rolling ball viscometer) or rheometer. Unless otherwise indicated, the viscosity measurement (centipoise, cP) is that at about 25° C. with a shear rate in the range of 100,000 to 250,000 1/sec.

The term "parenteral administration" refers to a route of administration other than by way of the intestines and includes injection of a dosage form into the body by a syringe or other mechanical device such as an infusion pump. Parenteral routes can include intravenous, intramuscular, subcutaneous and intraperitoneal routes of administration. Subcutaneous injection is a preferred route of administration.

The term "treatment" refers to therapeutic treatment and/or prophylactic or preventative measures. Those in need of treatment include the subjects already having the disease as well as those in which the disease is to be prevented. Hence, the patient to be treated herein may have been diagnosed as having the disease or may be predisposed or susceptible to the disease.

The term "effective amount" refers to an amount of a substance that provides the desired effect. In the case of a pharmaceutical drug substance it is the amount of active ingredient effective to treat a disease in the patient. In the case of a formulation ingredient, for example, a hyaluronidase enzyme, an effective amount is the amount necessary to increase the dispersion and absorption of the co-administered MASP-2 inhibitory antibody in such a way that the MASP-2 inhibitory antibody can act in a therapeutically effective way as outlined above.

As used herein, the term "about" as used herein is meant to specify that the specific value provided may vary to a certain extent, such as a variation in the range of ±10%, preferably ±5%, most preferably ±2% are included in the given value. For example, the phrase "a pharmaceutical formulation having about 200 mg/mL MASP-2 inhibitory antibody" is understood to mean that the formulation can have from 180 mg/mL to 220 mg/mL MASP-2 inhibitory antibody (e.g., OMS646). Where ranges are stated, the endpoints are included within the range unless otherwise stated or otherwise evident from the context.

As used herein the singular forms "a", "an" and "the" include plural aspects unless the context clearly dictates otherwise. Thus, for example, reference to "an excipient" includes a plurality of such excipients and equivalents thereof known to those skilled in the art, reference to "an agent" includes one agent, as well as two or more agents; reference to "an antibody" includes a plurality of such antibodies and reference to "a framework region" includes reference to one or more framework regions and equivalents thereof known to those skilled in the art, and so forth.

Each embodiment in this specification is to be applied mutatis mutandis to every other embodiment unless expressly stated otherwise. It is contemplated that any embodiment discussed in this specification can be implemented with respect to any method, kit, reagent, or composition of the invention, and vice versa. Furthermore, compositions of the invention can be used to achieve methods of the invention.

II. Overview of the Invention

The present disclosure provides stable, high-concentration low-viscosity MASP-2 inhibitory antibody pharmaceutical formulations suitable for parenteral administration (e.g., subcutaneous administration) and also suitable for dilution prior to intravenous administration. Highly concentrated pharmaceutical formulations of therapeutic antibody are desirable because they allow lower volume administration and/or fewer administrations, which consequently mean less discomfort to the patient. Additionally, such lower volumes allow packaging of the therapeutic doses of MASP-2 inhibitory antibody in individual single-dose, pre-filled syringes or vials for self-administration. The high-concentration, low-viscosity formulations of the present disclosure comprise an aqueous solution comprising a buffer system having a pH of 4.0 to 8.0, more preferably having a pH of about 5.0 to about 7.0, and a MASP-2 inhibitory monoclonal antibody (e.g., OMS646) or antigen-binding fragment thereof at a concentration of about 50 mg/mL to about 250 mg/mL. In preferred embodiments, the MASP-2 inhibitory antibody (e.g., OMS646) is present in the high concentration formulations suitable for subcutaneous administration at a concentration of from about 100 mg/mL to about 250 mg/mL. In particular embodiments, the MASP-2 inhibitory antibody (e.g., OMS646) is present in the high concentration formulations at a concentration of from about 150 mg/mL to about 200 mg/mL, such as about 175 mg/mL to about 195 mg/mL, such as about 185 mg/mL.

In various embodiments, the pharmaceutical formulations further comprise, in addition to the highly concentration MASP-2 inhibitory antibody and buffer system, one or more excipients, such as a tonicity modifying agent (e.g., an amino acid with a charged side chain), and optionally a non-ionic surfactant. In some embodiments, the pharmaceutical formulations in accordance with this disclosure further comprise a hyaluronidase enzyme.

A significant advantage of the highly concentrated pharmaceutical formulations of MASP-2 inhibitory antibody of the present invention is their low viscosity at high protein concentrations. As known to those skilled in the art, high viscosity of monoclonal antibody pharmaceutical formulations at concentrations ≥100 mg/mL can impede their development as products suitable for subcutaneous and/or intravenous delivery. Therefore, pharmaceutical formulations having lower viscosity are highly desirable because of their ease of manufacturability, such as but not limited to processing, filtering, and filling. As described in Examples 2 and 3 herein, the formulations of the present disclosure comprising from 100 mg/mL to 200 mg/mL MASP-2 inhibitory antibody OMS646 have surprisingly low viscosity, such as a viscosity less than about 50 cP, such as between 2 cP and 50 cP, such as between 2 cP and 40 cP, such as between 2 cP and 30 cP, or between 2 cP and 25 cP, or between 2 cP and 20 cP, or between 2 cP and 18 cP.

Additionally, the low viscosity, highly concentrated MASP-2 inhibitory antibody pharmaceutical formulations of the present invention allow the pharmaceutical formulations to be administered via standard syringe and needles, auto-injector devices, and microinfusion devices known in the art. As described in Example 3, the high concentration low viscosity of the MASP-2 inhibitory antibody pharmaceutical formulations as disclosed herein were determined to have syringeability and injectability suitable for subcutaneous administration. Syringeability and injectability are key product performance parameters of a pharmaceutical formulation intended for any parenteral administration, e.g., intramuscular or subcutaneous and permit the administration of such formulations by intramuscular or subcutaneous injection via small-bore needles typically used for such injections, such as, for example, 29GA regular or thin-walled, 27GA (1.25") regular or thin-walled, or 25GA (1") regular or thin-walled needles. In some instances, the low viscosity of MASP-2 inhibitory antibody pharmaceutical formulations as disclosed herein permit the administration of an acceptable (for example, 1-3 cc) injected volume while delivering an effective amount of the MASP-2 inhibitory antibody OMS646 in a single injection at a single injection site.

A further significant advantage of the formulations of the present disclosure is that the high concentration low viscosity formulations of MASP-2 inhibitory antibody (i.e., ≥100 mg/mL to 200 mg/mL) are stable when stored at 2° C. to 8° C. for at least 30 days, up to at least 9 months, or up to at least 12 months or longer, as described in the stability studies in Examples 2 and 4.

The present disclosure also provides a process for the preparation of the high concentration low viscosity MASP-2 inhibitory antibody formulations, containers including said formulations, therapeutic kits comprising the formulations; and to therapeutic methods of using such formulation, containers and kits for the treatment of a subject suffering from, or at risk for developing a disease or condition associated with MASP-2-dependent complement activation.

MASP-2 Inhibitory Antibody

As detailed herein, the present invention is drawn to formulations comprising monoclonal antibodies that specifically bind to MASP-2 and inhibit MASP-2-dependent complement activation and antigen-binding fragments thereof. In certain embodiments, a MASP-2 inhibitory antibody or antigen-binding fragment thereof for use in the claimed formulations is a MASP-2 inhibitory antibody referred to as "OMS646" as described in WO2012/151481 (hereby incorporated herein by reference) which comprises a heavy chain polypeptide comprising the amino acid sequence of SEQ ID NO:2 and a light chain polypeptide comprising the amino acid sequence of SEQ ID NO:3. As described in WO2012/151481 and described in Example 1, OMS646 specifically binds to human MASP-2 with high affinity and has the ability to block lectin pathway complement activity. In certain embodiments, a MASP-2 inhibitory antibody or antigen-binding fragment thereof for use in the claimed formulations is a MASP-2 inhibitory antibody comprising a heavy-chain variable region comprising (i) CDR-H1 comprising the amino acid sequence from 31-35 of SEQ ID NO:2, (ii) CDR-H2 comprising the amino acid sequence from 50-65 of SEQ ID NO:2, and iii) CDR-H3 comprising the amino acid sequence from 95-107 of SEQ ID NO:2; and (b) a light-chain variable region comprising: i) CDR-L1 comprising the amino acid sequence from 24-34 of SEQ ID NO:3, ii) CDR-L2 comprising the amino acid sequence from 50-56 of SEQ ID NO:3, and iii) CDR-L3 comprising the amino acid sequence from 89-97 of SEQ ID NO:3. In some embodiments, the MASP-2 inhibitory antibody for use in the claimed formulations comprises a variant of OMS646 comprising a heavy chain variable region having at least 95% identity to SEQ ID NO:2 and comprising a light chain variable region having at least 95% identity to SEQ ID NO:3. In some embodiments, the MASP-2 inhibitory antibody for use in the claimed formulations comprises a variant of OMS646 comprising an amino acid sequence having at least 95% identity to SEQ ID NO:2, wherein residue 31 is an R, residue 32 is a G, residue 33 is a K, residue 34 is an M, residue 35 is a G, residue 36 is a V, residue 37 is an S, residue 50 is an L, residue 51 is an A, residue 52 is an H, residue 53 is an I, residue 54 is an F, residue 55 is an S, residue 56 is an S, residue 57 is a D, residue 58 is an E, residue 59 is a K, residue 60 is an S, residue 61 is a Y, residue 62 is an R, residue 63 is a T, residue 64 is an S, residue 65 is an L, residue 66 is a K, residue 67 is an S, residue 95 is a Y, residue 96 is a Y, residue 97 is a C, residue 98 is an A, residue 99 is an R, residue 100 is an I, residue 101 is an R, residue 102 is an R or A, residue 103 is a G, residue 104 is a G, residue 105 is an I, residue 106 is a D and residue 107 is a Y; and b) a light chain variable region comprising an amino acid sequence having at least 95% identity to SEQ ID NO:3, wherein residue 23 is an S, residue 24 is a G, residue 25 is an E or D, residue 26 is a K, residue 27 is an L, residue 28 is a G, residue 29 is a D, residue 30 is a K, residue 31 is a Y or F, residue 32 is an A, residue 33 is a Y, residue 49 is a Q, residue 50 is a D, residue 51 is a K or N, residue 52 is a Q or K, residue 53 is an R, residue 54 is a P, residue 55 is an S, residue 56 is a G, residue 88 is a Q, residue 89 is an A, residue 90 is a W, residue 91 is a D, residue 92 is an S, residue 93 is an S, residue 94 is a T, residue 95 is an A, residue 96 is a V and residue 97 is an F.

In some embodiments, the monoclonal MASP-2 inhibitory antibody (e.g., OMS646 or a variant thereof) for use in the claimed formulations is a full length monoclonal antibody. In some embodiments, the monoclonal MASP-2 inhibitory antibody is a human IgG4 full length antibody. In some embodiments, the IgG4 comprises a point mutation in the hinge region to enhance the stability of the antibody.

In some embodiments, the MASP-2 inhibitory antibody (e.g., OMS646 or a variant thereof) is comprised of variable regions of human origin fused to human IgG4 heavy chain and lambda light chain constant regions, wherein the heavy chain comprises a point mutation in the hinge region (e.g., wherein the IgG4 molecule comprises a S228P mutation) to enhance the stability of the antibody. In some embodiments, the MASP-2 inhibitory antibody is a tetramer consisting of two identical heavy chains having the amino acid sequence set forth in SEQ ID NO:4 and two identical light chains having the amino acid sequence set forth in SEQ ID NO:5.

In some embodiments, the concentration of the MASP-2 inhibitory antibody in the formulation is from about 100 mg/mL to about 250 mg/mL, such as about 150 mg/ml to about 220 mg/mL, such as about 175 mg/mL to about 200 mg/mL, or about 175 mg/mL to about 195 mg/mL. In certain embodiments, the MASP-2 inhibitory antibody is present in the formulation at a concentration of about 175 mg/ml to about 195 mg/ml, such as about 180 mg/mL to about 190 mg/mL, such as about 175 mg/mL, such as about 180 mg/mL, about 181 mg/mL, about 182 mg/mL, about 183 mg/mL, about 184 mg/mL, about 185 mg/mL, about 186 mg/mL, about 187 mg/mL, about 188 mg/mL, about 189 mg/mL or such as about 190 mg/mL.

In some embodiments, minor variations in the amino acid sequences of the MASP-2 inhibitory antibodies or fragments thereof are contemplated as being encompassed by the claimed formulations, provided that the variations in the amino acid sequence maintains at least 90%, at least 95%, at least 96%, at least 97%, at least 98%, or at least 99% sequence identity to the MASP-2 inhibitory antibodies or antigen-binding fragments thereof described herein (i.e., at least 90%, at least 95%, at least 96%, at least 97%, at least 98%, or at least 99% sequence identity to SEQ ID NO:2 and/or at least at least 90%, at least 95%, at least 96%, at least 97%, at least 98%, or at least 99% sequence identity to SEQ ID NO:3) and retain the ability to inhibit MASP-2-dependent complement activation.

As will be appreciated, MASP-2 inhibitory antibodies or antigen-binding fragments thereof that are formulated in the context of the present disclosure can be produced using techniques well known in the art (e.g., recombinant technologies, phage display technologies, synthetic technologies, or combinations of such technologies or other technologies readily known in the art). Methods for producing and purifying antibodies and antigen-binding fragments are well known in the art and can be found, for example, in Harlow and Lane (1988) Antibodies, A Laboratory Manual, Cold Spring Harbor Laboratory Press, Cold Spring Harbor, N.Y., Chapters 5-8 and 15.

For example, MASP-2 inhibitory antibodies, such as OMS646 can be expressed in a suitable mammalian cell line. Sequences encoding the heavy chain variable region and the light chain variable region of a particular antibody of interest such as OMS646 (e.g., SEQ ID NO:6 and SEQ ID NO:7) can be used to transform a suitable mammalian host cell. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BNK) cells, monkey kidney cells (COS), human hepatocellular carcinoma cells (e.g., HepG2), human epithelial kidney 293 cells (HEK293) and numerous other cell lines.

Following the protein production phase of the cell culture process, MASP-2 inhibitory antibodies are recovered from the cell culture medium using techniques understood by one skilled in the art. In particular, in some embodiments the MASP-2 inhibitory antibody heavy and light chain polypeptides are recovered from the culture medium as secreted polypeptides.

MSP-2 inhibitory antibodies can be purified using, for example, hydroxyapatite chromatography, gel electrophoresis, dialysis, and affinity chromatography, and any combination of known or yet to be discovered purification techniques, including but not limited to Protein A chromatography, fractionation on an ion-exchange column, ethanol precipitation, reverse phase HPLC, chromatography on silica, chromatography on heparin SEPHAROSET®, an anion or cation exchange resin chromatography (such as a polyaspartic acid column), chromatofocusing, SDS-PAGE, and ammonium sulfate precipitation. The purification method can further comprise additional steps that inactivate and/or remove viruses and/or retroviruses that might potentially be present in the cell culture medium of mammalian cell lines. A significant number of viral clearance steps are available, including but not limited to, treating with chaotropes such as urea or guanidine, detergents, additional ultrafiltration/diafiltration steps, conventional separation, such as ion-exchange or size exclusion chromatography, pH extremes, heat, proteases, organic solvents or any combination thereof.

The purified MASP-2 inhibitory antibodies typically require concentration and a buffer exchange prior to storage or further processing. As a non-limiting example, a tangential flow filtration (TFF) system may be used to concentrate and exchange the elution buffer from the previous purification column with the final buffer desired for the drug substance.

The monoclonal MASP-2 inhibitory antibody which is formulated herein is preferably essentially pure and desirably essentially homogeneous (i.e., free from contaminating proteins, etc.). "Essentially pure" antibody means a composition comprising at least 90% by weight of the antibody, based on the total weight of the composition, preferably at least 95% by weight. "Essentially homogenous" antibody means a composition comprising at least about 99% by weight of antibody, based on total weight of the composition.

Aqueous Solutions

The high-concentration, low-viscosity MASP-2 inhibitory antibody formulation of the present disclosure comprises an aqueous solution comprising a buffer system having a pH of 4.0 to 8.0 (e.g., having a pH from about 5.0 to about 7.0, or having a pH from about 5.5 to about 6.5) and a MASP-2 inhibitory antibody (e.g., OMS646 or a variant thereof) or antigen-binding fragment thereof at a concentration of about 50 mg/mL to about 250 mg/mL (e.g., from about 100 mg/mL to about 250 mg/mL). The aqueous solution for use in the formulations of the present disclosure is one which is pharmaceutically acceptable (safe and non-toxic for administration to a human) and is useful for the preparation of a liquid formulation. In some embodiments, the aqueous solution is water, such as sterile water for injection (WFI), which is a sterile, solute-free preparation of distilled water. Alternatively, other aqueous solutions that are suitable for therapeutic administration and which would not adversely affect the stability of the formulation may be used, such as deionized water. Other suitable aqueous solutions include bacteriostatic water for injection (BWFI), sterile saline solution, Ringer's solution, or other similar aqueous solutions used for pharmaceutical solutions.

Buffering Systems

The high-concentration, low-viscosity MASP-2 inhibitory antibody formulation of the present disclosure is adjusted to a pH from 4.0 to 8.0, preferably from pH 5.0 to 7.0. The desired pH is suitably maintained by use of a buffering system. In some embodiments, the buffer system comprises at least one pharmaceutically acceptable buffering agent with an acid dissociation constant within 2 pH units of the formulation pH. The buffer system used in the formulations in accordance with the present invention has a pH in the range from about 4.0 to about 8.0. Various buffering agents are known to the person skilled in the art. Examples of buffering agents that will control the pH in this range include acetate, succinate, gluconate, histidine, citrate, and other organic acid buffers. In some embodiments, the buffering agent is selected from the group consisting of succinate, histidine and citrate. In some embodiments, the pharmaceutical formulations comprise a buffering system with a buffering agent in a concentration of from 1 to 50 mM, such as from 10 to 40 mM, or such as from 10 to 30 mM, or from 20 to 30 mM, or about 20 mM.

In some embodiments, the buffering agent is a histidine buffer. A "histidine buffer" is a buffer comprising the amino acid histidine. Examples of histidine buffers include histidine or any histidine salts including histidine hydrochloride, histidine acetate, histidine phosphate, and histidine sulfate, including combinations of any of these salts with or without histidine. In one embodiment, the buffering system comprises histidine hydrochloride buffer (L-Histidine/HCL). Such histidine hydrochloride buffer may be prepared by titrating L-histidine (free base, solid) with diluted hydrochloric acid or by using the appropriate mixture of histidine and histidine hydrochloride. In some embodiments, the pH of the L-Histidine/HCl buffer is about 5.0 to about 7.0, such as about 5.5 to about 6.0, e.g., about 5.8 or about 5.9.

In some embodiments, the buffering agent is a citrate buffer. Such citrate buffer may be prepared by titrating citric acid, the mono-sodium salt of citric acid, and/or the di-sodium salt of citric acid with diluted sodium hydroxide solution to the appropriate pH or by using the appropriate mixture of citric acid and the salt(s) to achieve this same pH. In another embodiment, the citrate buffer may be prepared by titrating a tri-sodium citrate solution with diluted hydrochloric acid solution to the appropriate pH. In this case, the ionic strength may be slightly higher than starting with citric acid due to the generation of additional ions of sodium and chloride in the solution. In certain embodiments, the pH of the citrate buffer is about 5.0 to about 7.0, such as about 5.5 to about 6.0, e.g., about 5.8 or about 5.9. In some embodiments, the buffering agent is a succinate buffer. In certain embodiments, the pH of the succinate buffer is about 5.5 to about 6.0, e.g., about 5.8 or about 5.9.

In some embodiments, the buffering agent is a sodium citrate buffer, wherein sodium citrate is present in the formulation at a concentration of about 10 mM to about 50 mM, such as from about 10 mM to about 25 mM, such as about 20 mM. In some embodiments, the buffering agent is a L-histidine buffer, wherein L-histidine is present in the formulation at a concentration of about 10 mM to about 50 mM, such as from about 10 mM to about 25 mM, such as about 20 mM. In some embodiments, the formulation comprises about 20 mM sodium citrate and has a pH from about 5.0 to about 7.0. In some embodiments, the formulation comprises about 20 mM L-histidine and has a pH from about 5.0 to about 7.0.

Excipients

In some embodiments, the high-concentration, low-viscosity MASP-2 inhibitory antibody formulation of the present disclosure further comprises at least one excipient. Examples of suitable excipients include, but are not limited to, proteins (e.g., serum albumin), amino acids (e.g., aspartic acid, glutamic acid, lysine, arginine, glycine and histidine), saccharides (e.g., glucose, sucrose, maltose and trehalose), polyols (e.g., mannitol and sorbitol), fatty acids and phospholipids (e.g., alkyl sulfonates and caprylate).

In some embodiments, the formulation comprises an excipient selected from the group consisting of an amino acid with a charged side chain, a sugar or other polyol and a salt. In some embodiments, the formulation comprises a sugar or other polyol, such as, for example, sucrose, trehalose, mannitol or sorbitol. In some embodiments, the formulation comprises a salt, such as, for example NaCl or a salt of an amino acid.

In some embodiments, the formulation comprises an excipient that is a tonicity modifying agent. In some embodiments, the tonicity modifying agent is included in the formulation in a concentration suitable to provide an isotonic formulation. In some embodiments, the tonicity modifying agent is included in the formulation in a concentration suitable to provide a hypertonic formulation. In some embodiments, the tonicity modifying agent for use in the formulation is selected from the group consisting of an amino acid with a charged side chain, a sugar or other polyol and a salt. In some embodiments, the tonicity modifying agent is an amino acid with a charged side chain (i.e., a negatively charged side chain or a positively charged side chain) at a concentration of from about 50 mM to about 300 mM. In some embodiments, the tonicity modifying agent is an amino acid with a negatively charged side chain, such as glutamate. In some embodiments, the formulation comprises glutamate at a concentration of about 50 mM to about 300 mM. In some embodiments, the tonicity modifying agent is an amino acid with a positively charged side chain, such as arginine. In some embodiments, the formulation comprises arginine (e.g., arginine HCL), at a concentration of from about 50 mM to about 300 mM, such as from about 150 mM to about 225 mM.

Preferably, the pharmaceutical formulations as disclosed herein are hypertonic (i.e., have a higher osmotic pressure than human blood). As described herein, it was unexpectedly observed that hypertonicity led to reduced sample viscosity, which was achieved, for example, with modest increases in arginine concentration. As described in Example 2, it was unexpectedly observed that low viscosities were achieved (e.g., less than 25 cP) with the citrate/arginine and the histidine/arginine high concentration MASP-2 inhibitory antibody formulations comprising an arginine concentration of 200 mM or greater in the absence of $CaCl_2$. Accordingly, in some embodiments, the formulation comprises arginine (e.g., arginine HCL) at a hypertonic level of from about 200 mM to about 300 mM.

As further described in Example 2, it was also observed that formulations which included divalent cations ($CaCl_2$ or $MgCl_2$) had elevated high molecular weight material as compared to formulations that did not include $CaCl_2$ or $MgCl_2$ additives. Accordingly, in one embodiment, the high-concentration, low viscosity MASP-2 inhibitory antibody formulation of the present disclosure is substantially free of a $CaCl_2$ additive. In one embodiment, the high-concentration, low-viscosity MASP-2 inhibitory antibody formulation of the present disclosure is substantially free of a $MgCl_2$ additive.

As further described in Example 2, it was determined for the high concentration MASP-2 antibody formulations that the inclusion of sucrose was associated with elevated polydispersity in all buffering systems tested. Accordingly, in one embodiment, the high concentration low viscosity MASP-2 inhibitory antibody formulation of the present disclosure is substantially free of sucrose.

As described in Example 2, it was also determined for the high concentration MASP-2 antibody formulations that the inclusion of sorbitol was associated with elevated polydispersity in all buffering systems tested. Accordingly, in one embodiment, the high concentration low viscosity MASP-2 inhibitory antibody formulation of the present disclosure is substantially free of sorbitol.

Surfactants

Optionally, in some embodiments, the high-concentration, low-viscosity MASP-2 inhibitory antibody formulation of the present disclosure further comprises a pharmaceutically acceptable surfactant. Non-limiting examples of suitable pharmaceutically acceptable surfactants include polyoxyethylensorbitan fatty acid esters (e.g., Tween), polyethylene-polypropylene glycols, polyoxyethylene-stearates, polyoxyethylene alkyl ethers (e.g., polyoxyethylene monolauryl ether), alkylphenylpolyoxyethylene ethers (e.g., Triton-X), polyoxyethylene-polyoxypropylene copolymer (e.g., Poloxamer and Pluronic), and sodium dodecyl sulphate (SDS). In certain embodiments, the pharmaceutically acceptable surfactant is a polyoxyethylenesorbitan-fatty acid ester (polysorbate), such as polysorbate 20 (sold under the trademark Tween 20™) and polysorbate 80 (sold under the trademark Tween 80™). In some embodiments, the high-concentration, low-viscosity MASP-2 inhibitory antibody formulation of the present disclosure comprises a non-ionic surfactant. The nonionic surfactant can be a polysorbate, (e.g., selected from the group of polysorbate 20, polysorbate 80, and polyethylene-polypropylene copolymer). In some embodiments, the concentration of the surfactant is about 0.001 to 0.1% (w/v), or 0.005% to 0.1% (w/v), or 0.01 to 0.1% (w/v), or 0.01 to 0.08% (w/v), or 0.025 to 0.075% (w/v), or more particularly about 0.01% (w/v), about 0.02% (w/v), about 0.04% (w/v), or about 0.06% (w/v), or about 0.08% (w/v), or about 0.10% (w/v). In some embodiments, the formulation comprises a non-ionic surfactant (e.g., polysorbate 80) at a concentration of from about 0.001 to 0.1% (w/v), or 0.005% to 0.1% (w/v), or 0.01 to 0.1% (w/v), or 0.01 to 0.08% (w/v), or 0.025 to 0.075% (w/v), or more particularly about 0.01% (w/v), about 0.02% (w/v), about 0.04% (w/v), or about 0.06% (w/v), or about 0.08% (w/v), or about 0.10% (w/v). As described in Example 2, it was unexpectedly observed that the inclusion of the non-ionic surfactant polysorbate 80 (PS-80) led to a further reduction in viscosity while also preserving protein recovery, thereby allowing for a high concentration of OMS646 antibody while maintaining a low viscosity suitable for use in an injection device, such as an autoinjector.

Stabilizers

Optionally, in some embodiments, the high-concentration, low-viscosity MASP-2 inhibitory antibody formulation of the present disclosure further comprises a stabilizer. The stabilizer (used synonymously with the term "stabilizing agent" herein) may be a carbohydrate or saccharide or a sugar admitted by the regulatory authorities as a suitable additive or excipient in pharmaceutical formulations, e.g., trehalose or sucrose. The typical concentration of the stabilizer is 15 to 250 mM, or 150 to 250 mM, or about 210 mM. The formulations may contain a secondary stabilizer, such as methionine, e.g., in a concentration of 5 to 25 mM or in a concentration of 5 to 15 mM (e.g., methionine in a concentration of about 5 mM, about 10 mM or about 15 mM).

Preservatives

Optionally, in some embodiments, the high-concentration, low-viscosity MASP-2 inhibitory antibody formulation of the present disclosure further comprises a preservative (e.g., an antimicrobial agent). Antimicrobial agents are generally required for parenteral products that are intended for multiple dosing. Similarly, preservatives are added to pharmaceutical formulations aseptically packaged in single dose vials if the active ingredient(s) does not have bactericidal or bacteriostatic properties or is growth promoting. Some typical preservatives used are benzyl alcohol (0.9% to 1.5%), methylparaben (0.18% to 0.2%), propylparaben (0.02%), benzalkonium chloride (0.01% to 0.02%), and thimerosal (0.001% to 0.01%).

Syringeability

The subcutaneous route of administration requires injections using injection devices, such as syringes, auto-injectors, wearable pumps, or other devices, which restricts product formulation with regard to injection volume and solution viscosity. In addition, product formulation must be suitable for use in an injection device with regard to injection force and time required for injection delivery. "Syringeability," as used herein, refers to the ability of an injectable therapeutic to pass easily through a hypodermic needle on transfer from a vial prior to an injection. "Injectability," as used herein, refers to the performance of the formulation during injection (see, e.g., Cilurzo F, Selmin F, Minghetti P, et al. Injectability Evaluation: An Open Issue. *AAPS PharmSciTech*. 2011; 12(2):604-609). Syringeability includes such factors as ease of withdrawal, clogging and foaming tendencies, and accuracy of dose measurements. Injectability includes pressure or force required for injection, evenness of flow, and freedom from clogging (i.e., no blockage of the syringe needle). Syringeability and injectability can be affected by the needle geometry, i.e., inner diameter, length, shape of the opening, as well as the surface finish of the syringe, especially in self-injection devices such as pens and auto-injectors (e.g., equipped with 29-31 GA needles), and in pre-filled syringes for subcutaneous dosing (e.g., equipped with 24-27 GA needles). Injection force (or glide force) is a complex factor influenced by solution viscosity, the size of the needle (i.e., needle gauge), and surface tension of the container/closure. Smaller needles, e.g., ≥gauge, will pose less pain sensation to patients. Overcashier and co-workers established a viscosity-glide force relationship as a function of needle gauge based on Hagen-Poiseuille Equation (Overcashier et al., *Am Pharm Rev* 9(6):77-83 (2006). For example, with a 27-gauge thin walled needle, the liquid viscosity should be maintained at or below 20 cP in order to not exceed the glide force of 25 Newton (N).

In certain embodiments, the pharmaceutical formulations of the invention are characterized by having an injection glide force of about 25N or less when injected through a 27GA (1.25") needle at room temperature.

In certain embodiments, the pharmaceutical formulations of the invention are characterized by having an injection glide force of about 20N or less when injected through a 25GA (1") needle at room temperature.

As exemplified in Example 3, the high-concentration, low-viscosity MASP-2 inhibitory antibody (e.g., OMS646) formulations of the present disclosure have surprisingly good syringeability and injectability. The high-concentration, low-viscosity MASP-2 inhibitory antibody formulations as disclosed herein allow for the administration of such formulations by intramuscular or subcutaneous injection via small-bore needles typically used for such injections, for example, 27 G (1.25"), 27 G thin-walled, 25 G thin-walled (1"), or 25 G (1") needles. In some instances, the low viscosity of MASP-2 inhibitory antibody formulations as disclosed herein allows for the administration of a tolerable (for example, 1-3 cc) injected volume while delivering an effective amount of the MASP-2 inhibitory antibody in a single injection at a single injection site.

Stability

For any of the foregoing, it should be noted that the MASP-2 inhibitory antibody or antigen binding fragment thereof in the formulation retains the ability to inhibit MASP-2-dependent complement activation. For example, the MASP-2 inhibitory antibody retains the ability to bind MASP-2 and inhibit lectin pathway activity as described in Example 1 or other lectin pathway assay, for example as described in WO2012/151481. In addition to potency assays, various physical-chemical assays can be used to assess stability including isoelectric focusing, polyacrylamide gel electrophoresis, size exclusion chromatography, and visible and subvisible particle assessment.

In certain embodiments, the formulations of the present disclosure exhibit stability at a temperature range of −20° C.

to 8° C. for at least 30 days, up to at least 9 months or longer, or up to at least 12 months or longer, as described in the stability studies in Examples 2 and 4. Additionally or alternatively, in certain embodiments, the formulations are stable at the temperature of −20° C. to 8° C., such as from 2° C. to 8° C. for at least 6 months, at least 1 year, or at least 2 years or longer. In certain embodiments, stability may be assessed, for example, by maintenance of a level of purity over time. For example, in certain embodiments, formulations of the present disclosure have less than 5% decrease, such as less than 4% decrease, such as less than 3% decrease, such as less than 2%, such as less than 1% decrease in purity per month, 6 months, 9 months, or 1 year when stored at 2° C. to 8° C., as determined by size exclusion chromatography (SEC), which monitors the presence or absence of fragments (LMW) and/or aggregate species (HMW).

In certain embodiments, the formulations of the present disclosure promote low to undetectable levels of aggregation and/or fragmentation and maintain potency after storage for a defined period. Described another way, the formulations disclosed herein are capable of maintaining the structural integrity of the MASP-2 inhibitory antibody OMS646 present at high concentrations in a solution, e.g., at concentrations of greater than 150 mg/mL, or greater than 175 mg/mL, or of at least 185 mg/mL, such that the MASP-2 inhibitory antibody can remain predominately monomeric (i.e., at least 95% or greater) after storage of a defined period at approximately 2° C. to 8° C. Preferably, no more than 5%, no more than 4%, no more than 3%, no more than 2%, no more than 1%, and most preferably no more than 0.5% of the antibody forms fragment (LMW) or aggregate forms (HMW) as measured by SEC after storage of a defined period at approximately 2° C. to 8° C.

As exemplified in Example 4 described herein, the inventors provide formulations suitable for maintaining a MASP-2 inhibitory antibody, OMS646, at about 185 mg/mL in predominately monomeric form for at least 12 months at about 2° C. to 8° C.

Tissue Permeability Modifier

In another embodiment, the high-concentration, low-viscosity MASP-2 inhibitory antibody formulations of the present disclosure further comprise a tissue permeability modifier that increases the absorption or dispersion of the MASP-2 inhibitory antibody following parenteral administration (e.g., subcutaneous injection). In some embodiments, the tissue permeability modifier is a hyaluronidase enzyme which acts as a tissue permeability modifier and increases the dispersion and absorption of the injected MASP-2 inhibitory antibody. A particularly useful tissue permeability modifier is hyaluronidase (e.g., a recombinant human hyaluronidase). Hyaluronidases work as tissue permeability modifiers by temporarily breaking down the hyaluronan barrier to open access to the lymphatic and capillary vessels allowing injected drugs and fluids to be absorbed quickly into systemic circulation. The hyaluronan rebuilds naturally, and the barrier is completely restored, e.g., within 48 hours. Addition of hyaluronidase in the injectable pharmaceutical formulations increases bioavailability of the MASP-2 inhibitory antibody following parenteral administration, particularly subcutaneous administration. It also allows for greater injection site volumes (i.e., greater than 1 mL) with less pain and discomfort, and minimizes the incidence of injection site reactions (e.g., flattens the injection site bump).

In some embodiments, the high-concentration, low-viscosity MASP-2 inhibitory antibody (e.g., OMS646) formulation of the present disclosure comprise from about 100 U/mL to about 20,000 U/mL of a hyaluronidase enzyme. The actual concentration of the hyaluronidase enzyme depends on the type of hyaluronidase enzyme used in the preparation of the MASP-2 inhibitory antibody formulations of the present invention. An effective amount of the hyaluronidase can be determined by the person skilled in the art. It should be provided in sufficient amount so that an increase in the dispersion and absorption of the co-administered or sequentially administered MASP-2 inhibitory antibody is possible. The minimal amount of the hyaluronidase enzyme is greater than 100 U/mL. More particularly, the effective amount of the hyaluronidase enzyme is from about 150 U/mL to about 20,000 U/mL, whereby the said amount corresponds to about 0.01 mg to 0.16 mg protein based on an assumed specific activity of 100,000 U/mg. In some embodiments, the pharmaceutical formulations comprise hyaluronidase in concentration of about 1,000 to about 20,000 U/ml, such as about 1,000 to about 16,000 U/ml. Alternatively, the concentration of the hyaluronidase is about 1,500 to about 12,000 U/mL, or more particularly about 2,000 U/mL to about 12,000 U/mL. The amounts specified herein correspond to the amount of hyaluronidase initially added to the pharmaceutical formulation. In some embodiments, the ratio (w/w) of the hyaluronidase to the MASP-2 inhibitory antibody is in the range of 1:1,000 to 1:8,000, or in the range of 1:4,000 to 1:6,000 or in the range of about 1:4,000 to 1:5000.

The hyaluronidase may be present as a component of the high-concentration, low-viscosity MASP-2 inhibitory antibody formulation of the present disclosure, or it may be provided as a separate solution in a kit-of-parts. Thus, in one embodiment, the MASP-2 inhibitory antibody is co-formulated with a hyaluronidase. In another embodiment, the MASP-2 inhibitory antibody and hyaluronidase are formulated separately and mixed just prior to subcutaneous administration. In yet another embodiment, the MASP-2 inhibitory antibody and hyaluronidase are each formulated and administered separately, e.g., the hyaluronidase is administered as a separate injection directly before or after administration of the formulation comprising the MASP-2 inhibitory antibody. In some instances, the hyaluronidase is administered subcutaneously from about 5 seconds to about 30 minutes prior to the injection of the pharmaceutical formulation comprising the MASP-2 inhibitory antibody of the present disclosure into the same injection site area. In certain embodiments, the pharmaceutical formulation of MASP-2 inhibitory antibody and hyaluronidase solution are included in separate chambers of a pharmaceutical device which automates delivery, either simultaneously (e.g., using a dual barrel syringe) or sequentially.

Pre-Filled Containers

In a further aspect of the present disclosure, the high-concentration, low-viscosity MASP-2 inhibitory antibody formulation as disclosed herein is contained in a pre-filled sealed container in an amount sufficient for administration to a mammalian subject. Thus a sufficient quantity of drug composition formulated in accordance with the present disclosure, that is equal or just slightly more (i.e., not more than 25% excess, such as not more than 10% excess) than the amount of MASP-2 inhibitory antibody desired to be administered to a mammalian subject is contained within a pre-filled container that facilitates dispensing the antibody formulation for parenteral administration (i.e., injection or infusion). In some embodiments, the pre-filled container comprises at least one pharmaceutical unit dosage form of the MASP-2 inhibitory antibody.

For example, a desired single-use quantity of high-concentration, low-viscosity MASP-2 inhibitory antibody formulation may be packaged in pre-filled container, such as, for example, a glass vial closed with a stopper or other closure that includes a septum through which a hypodermic needle may be inserted to withdraw the formulation, or may be packaged in a pre-filled syringe or other pre-filled container suitable for injection (e.g., subcutaneous injection) or infusion. Examples of such containers include, without limitation, vials, syringes, ampoules, bottles, cartridges, and pouches. Preferably the containers are each single-use pre-filled syringes, which may suitably be formed of glass or a polymeric material such as a cyclic olefin polymers or acrylonitrile butadiene styrene (ABS), polycarbonate (PC), polyoxymethylene (POM), polystyrene (PS), polybutylene terephthalate (PBT), polypropylene (PP), polyethylene (PE), polyamide (PA), thermoplastic elastomer (TPE), and their combinations. The barrels of such syringes are operated with an elastomer plunger which can be urged along the barrel to eject liquid content via a needle connected thereto. In some embodiments of the invention, each syringe includes a needle affixed thereto.

In some embodiments, the high-concentration, low-viscosity MASP-2 inhibitory antibody formulation as disclosed herein is contained within a pre-filled container selected from the group consisting of: a syringe (e.g., a single or double barreled syringe), a pen injector, a sealed vial (e.g., a dual chamber vial), an auto-injector, a cassette, and a pump device (e.g., an on-body patch pump, a tethered pump or an osmotic pump). For subcutaneous delivery, the formulation may be contained within a pre-filled device suitable for subcutaneous delivery, such as, for example, a pre-filled syringe, autoinjector, injection device (e.g., the INJECT-EASE™, or GENJECT™ device), injector pen (such as the GENPEN™) or other device suitable for subcutaneous administration.

The formulations of the present disclosure can be prepared as unit dosage forms in a pre-filled container, which can be particularly suitable for self-administration. For example, a unit dosage per vial, cartridge or other pre-filled container (e.g., pre-filled syringe or disposable pen) may contain about 0.1 mL, 0.2 mL, 0.3 mL, 0.4 mL, 0.5 mL, 0.6 mL, 0.7 mL, 0.8 mL, 0.9 mL, 1 mL, 1.1 mL, 1.2 mL, 1.3 mL, 1.4 mL, 1.5 mL, 1.6 mL, 1.7 mL, 1.8 mL, 1.9 mL, 2.0 mL, 2.1 mL, 2.2 mL, 2.3 mL, 2.4 mL, 2.5 mL, 2.6 mL, 2.7 mL, 2.8 mL, 2.9 mL, 3.0 mL, 3.5 mL, 4.0 mL, 4.5 mL, 5.0 mL, 5.5 mL, 6.0 mL, 6.5 mL, 7.0 mL, 7.5 mL, 8.0 mL, 8.5 mL, 9.0 mL, 9.5 mL, or about 10.0 mL or greater volume of the high concentration formulation containing various concentrations of MASP-2 inhibitory antibody (e.g., OMS646) ranging from about 100 mg/mL to about 250 mg/mL, about 150 mg/mL to about 200 mg/mL, about 175 mg/mL to about 200 mg/mL, such as about 185 mg/mL, resulting in a total unit dosage of OMS646 per container ranging from about 20 mg to about 1000 mg or higher.

In some embodiments, the formulation of the present disclosure is prepared as a unit dosage form in a pre-filled container, such as a vial or syringe, at a unit dosage of about 350 mg to 400 mg, such as about 350 mg, about 360 mg, about 370 mg, about 380 mg, about 390 mg, or about 400 mg.

In some embodiments, the formulations of the present disclosure are prepared as unit dosage forms in a pre-filled syringe with a volume of from 0.1 mL to 3.0 mL, such as about 0.1 mL, 0.2 mL, 0.3 mL, 0.4 mL, 0.5 mL, 0.6 mL, 0.7 mL, 0.8 mL, 0.9 mL, 1 mL, 1.1 mL, 1.2 mL, 1.3 mL, 1.4 mL, 1.5 mL, 1.6 mL, 1.7 mL, 1.8 mL, 1.9 mL, 2.0 mL, 2.1 mL, 2.2 mL, 2.3 mL, 2.4 mL, 2.5 mL, 2.6 mL, 2.7 mL, 2.8 mL, 2.9 mL, or about 3.0 mL comprising from about 20 mg to 750 mg of the MASP-2 inhibitory antibody (e.g., OMS646). As described herein, the stable formulations prepared as unit dosages can be administered to a subject directly (e.g., via subcutaneous injection), or alternatively are prepared to be suitable for dilution prior to intravenous administration.

The formulations of the present disclosure may be sterilized by various sterilization methods suitable for antibody formulations, such as sterile filtration. In certain embodiments the antibody formulation is filter-sterilized, for example, with a presterilized 0.2 micron filter. Sterilized formulations of the present disclosure may be administered to a subject to prevent, treat or ameliorate a disease or disorder associated with MASP-2-dependent complement activation.

In a related aspect, the present disclosure provides a method of making an article of manufacture comprising filing a container with a high concentration MASP-2 inhibitory antibody formulation of the present disclosure.

In one embodiment, the present disclosure provides a pharmaceutical composition for use in treating a patient suffering from, or at risk for developing a MASP-2-dependent disease or condition, wherein the composition is a sterile, single-use dosage form comprising from about 350 mg to about 400 mg (i.e., 350 mg, 360 mg, 370 mg, 380 mg, 390 mg, or 400 mg) of MASP-2 inhibitory antibody, wherein the composition comprises about 1.8 mL to about 2.2 mL (i.e., 1.8 mL, 1.9 mL, 2.0 mL, 2.1 mL or 2.2 mL) of a 185 mg/mL antibody formulation, such as disclosed herein, wherein said antibody or fragment thereof comprises (i) a heavy chain variable region comprising the amino acid sequence set forth in SEQ ID NO:2 and (ii) a light chain variable region comprising the amino acid sequence set forth in SEQ ID NO:3; and wherein the formulation is stable when stored at between 2° C. and 8° C. for at least six months. In some embodiments, the MASP-2 dependent disease or condition is selected from the group consisting of aHUS, HSCT-TMA, IgAN and Lupus Nephritis (LN).

Kits Comprising High-Concentration, Low-Viscosity MASP-2 Inhibitory Antibody Formulations The present disclose also features therapeutic kits comprising at least one container including the high-concentration, low-viscosity MASP-2 inhibitory antibody formulation as disclosed herein.

In some embodiments, the present disclosure provides a kit comprising (i) a container comprising any of the formulations comprising MASP-2 inhibitory antibody described herein; and (ii) a suitable means for delivering the formulation to a patient in need thereof. In some embodiments of any of the kits described herein, the means is suitable for subcutaneous delivery of the formulation to the patient.

Various types of containers are suitable for containment of pharmaceutical formulations of MASP-2 inhibitory antibody included in the kits of the present invention. In certain embodiments of the kits of the present invention, the container is a prefilled syringe (e.g., a single barrel or double-barreled syringe) or a prefilled sealed vial.

In some embodiments, the container comprising a formulation comprising MASP-2 inhibitory antibody is a pre-filled container selected from the group consisting of: a syringe (e.g., a single or double barreled syringe), a pen injector, a sealed vial (e.g., dual chamber vials), an auto-injector, a cassette, and a pump device (e.g., an on-body patch pump or a tethered pump or an osmotic pump). For subcutaneous delivery, the formulation may be contained within a pre-filled device suitable for subcutaneous delivery, such as, for example, a pre-filled syringe, autoinjector, injection device (e.g., the INJECT-EASE™, and GENJECT™ device), injector pen (such as the GENPEN™) or other device suitable for subcutaneous administration.

In addition to a container pre-filled with a single-dose of the pharmaceutical formulation, the kit of the present invention may also include an outer container into which such pre-filled container is placed. For example, the outer container may include a plastic or paperboard tray into which recesses are formed that receive the pre-filled container and immobilize it during shipping and handling prior to use. In some embodiments, the outer container is suitably opaque and acts to shield the pre-filled container from light to prevent light induced degradation of the components of the pharmaceutical formulation. For example, the plastic or paperboard tray that receives pre-filled container may be further packaged within a paperboard carton that provides light shielding. The kit of the present invention may also include a set of instructions for administration and use of the MASP-2 inhibitory antibody formulations in accordance with the present invention, which may be printed on the outer container or printed on a sheet of paper that is contained within the outer container.

In some embodiments, the kits comprise a second container (e.g., a prefilled syringe) containing an effective dose of a hyaluronidase.

The kit may further include other materials desirable from a commercial and user standpoint, including needles, syringes, package inserts and the like.

Exemplary Formulations

As described above, the stable, high-concentration, low-viscosity MASP-2 inhibitory antibody formulations of the present disclosure include MASP-2 inhibitory antibody a concentration of from 50 mg/mL to 250 mg/mL in an aqueous solution comprising a buffering agent having a pH of 4.0 to 8.0.

The buffer system, such as histidine, citrate or succinate, is suitably included at a concentration of from about 10 mM to about 50 mM, and preferably at about 20 mM. In some preferred embodiments, the formulation further comprises an amino acid with a charged side chain at a concentration of from 50 mM to 300 mM. In some embodiments, the formulation comprises an amino acid with a positively charged side chain, such as arginine, at a concentration of from 50 mM to 300 mM. In some preferred embodiments, the formulation further comprises a non-ionic surfactant, such as polysorbate 80, in an amount from 0.001% (w/v) to 0.1% (w/v), such as about 0.05% (w/v) to about 0.1% (w/v). In some embodiments, the formulation further comprises a hyaluronidase enzyme in an amount effective to increase the dispersion and/or absorption of the MASP-2 inhibitory antibody following subcutaneous administration.

In some embodiments the stable high-concentration, low-viscosity MASP-2 inhibitory antibody formulations of the present disclosure comprise, consist of, or consist essentially of one of the following compositions:

a) 100 to 200 mg/mL MASP-2 inhibitory antibody; 10 to 50 mM of a histidine buffer at a pH of about 5.0 to about 7.0; 100 mM to 225 mM arginine; and optionally 100 to 20,000 U/mL of a hyaluronidase.

b) 100 to 200 mg/mL MASP-2 inhibitory antibody; 10 to 50 mM of a histidine buffer at a pH of about 5.0 to about 7.0; 100 mM to 225 mM arginine, about 0.01% to 0.08% (w/v) of a nonionic surfactant; and optionally 100 to 20,000 U/mL of a hyaluronidase.

c) 100 to 200 mg/mL MASP-2 inhibitory antibody; 10 to 50 mM of a citrate buffer at a pH of about 5.0 to about 7.0; 100 mM to 225 mM arginine, and optionally 100 to 20,000 U/mL of a hyaluronidase.

d) 100 to 200 mg/mL MASP-2 inhibitory antibody; 10 to 50 mM of a citrate buffer at a pH of about 5.0 to about 7.0; 100 mM to 225 mM arginine, about 0.01% to 0.08% (w/v) of a nonionic surfactant; and optionally 100 to 20,000 U/mL of a hyaluronidase.

e) 100 to 200 mg/mL MASP-2 inhibitory antibody; 10 to 50 mM of a succinate buffer at a pH of about 5.0 to about 7.0; 100 mM to 225 mM arginine, and optionally 100 to 20,000 U/mL of a hyaluronidase.

f) 100 to 200 mg/mL MASP-2 inhibitory antibody; 10 to 50 mM of a succinate buffer at a pH of about 5.0 to about 7.0; 100 mM to 225 mM arginine, about 0.01% to 0.08% (w/v) of a nonionic surfactant; and optionally 100 to 20,000 U/mL of a hyaluronidase.

In certain embodiments, the stable high-concentration, low-viscosity MASP-2 inhibitory antibody formulations of the present disclosure comprise, consist of, or consist essentially of one of the following compositions:

g) 185±18.5 mg/mL MASP-2 inhibitory antibody; 20±2 mM citrate buffer at a pH of about 5.8; 200±20 mM arginine, and optionally 100 to 20,000 U/mL of a hyaluronidase.

h) 185±18.5 mg/mL MASP-2 inhibitory antibody; 20±2 mM citrate buffer at a pH of about 5.8; 200±20 mM arginine, about 0.01% (w/v) polysorbate 80, and optionally 100 to 20,000 U/mL of a hyaluronidase.

i) 185±18.5 mg/mL MASP-2 inhibitory antibody; 20±2 mM histidine buffer at a pH of about 5.9, 200±20 mM arginine, and optionally 100 to 20,000 U/mL of a hyaluronidase.

j) 185±18.5 mg/mL MASP-2 inhibitory antibody; 20±2 mM histidine buffer at a pH of about 5.9, 200±20 mM arginine, about 0.01% polysorbate 80, and optionally 100 to 20,000 U/mL of a hyaluronidase.

Methods of Producing High-Concentration, Low-Viscosity MASP-2 Inhibitory Antibody Formulations In another aspect, the present disclosure provides a method for producing a formulation comprising 100 mg/mL or greater of a MASP-2 inhibitory antibody, the method comprising: (a) providing a first pharmaceutical formulation comprising purified OMS646, the first pharmaceutical formulation having a first formulation and comprising no more than 50 mg/mL of the OMS646 protein; (b) subjecting the first pharmaceutical formulation to filtration to thereby produce a second pharmaceutical formulation, wherein the second pharmaceutical formulation has a second formulation as a result of the filtration; and (c) concentrating the second pharmaceutical formulation to produce a concentrated antibody solution comprising 100 mg/mL or greater of OMS646. The formulated bulk solution is typically set at a fixed protein concentration so that the desired fill volume can be kept constant. The liquid drug product manufacturing process typically involves mixing the MASP-2 inhibitory antibody with the buffering system, excipients and optionally surfactant, followed by aseptic filtration and filling in vials (or other container, such as syringes) and sealing (e.g., stoppering, capping, or the like).

TABLE 1

Example Formulation 1

| Component (USP) added to water for injection | Concentration |
| --- | --- |
| OMS646 antibody | 185 mg/mL |
| Sodium Citrate | 20 mM |

TABLE 1-continued

Example Formulation 1

| Component (USP) added to water for injection | Concentration |
|---|---|
| L-Arginine HCL | 200 mM |
| Polysorbate 80 | 0.01% |

TABLE 2

Example Formulation 2

| Component (USP) added to water for injection | Concentration |
|---|---|
| OMS646 antibody | 185 mg/mL |
| L-Histidine | 20 mM |
| L-Arginine HCL | 200 mM |
| Polysorbate 80 | 0.01% |

Methods of Treatment

In another aspect, the present disclosure provides a method of treating a patient suffering from, or at risk for developing a MASP-2-dependent complement-associated disease or disorder comprising administering a high concentration low viscosity formulation comprising a MASP-2 inhibitory antibody (e.g., OMS646) as disclosed herein.

As described in U.S. Pat. Nos. 7,919,094; 8,840,893; 8,652,477; 8,951,522, 9,011,860, 9,644,035, U.S. Patent Application Publication Nos. US2013/0344073, US2013/0266560, US 2015/0166675, US2017/0137537, US2017/0189525 and co-pending U.S. patent application Ser. Nos. 15/476,154, 15/347,434, 15/470,647, 62/315,857, 62/275,025 and 62/527,926 (each of which is assigned to Omeros Corporation, the assignee of the instant application, each of which is hereby incorporated by reference), MASP-2-dependent complement activation has been implicated as contributing to the pathogenesis of numerous acute and chronic disease states. For example, as described in U.S. Pat. No. 8,951,522, the primary function of the complement system, a part of the innate immune system, is to protect the host against infectious agents, however, inappropriate or overactivation of the complement system can lead to serious disease, such as thrombotic microangiopathies (TMAs, including aHUS, TTP and HUS) in which endothelial damage as well as fibrin and platelet-rich thrombi in the microvasculature lead to organ damage. The lectin pathway plays a dominant role in activating complement in settings of endothelial cell stress or injury, and preventing the activation of MASP-2 and the lectin pathway halts the sequence of enzymatic reactions that lead to the formation of the membrane attack complex, platelet activation and leukocyte recruitment. As described in U.S. Pat. No. 8,652,477, in addition to initiation of the lectin pathway, MASP-2 can also activate the coagulation system and is capable of cleaving prothrombin to thrombin.

As described in Example 1 and U.S. Pat. No. 9,011,860, OMS646 is a potent inhibitor of lectin-dependent complement activation. This antibody shows no significant binding (at least 5000-fold lower affinity) to the other complement pathway serine proteases C1r, C1s, MASP-1 and MASP-3, and does not inhibit classical pathway dependent complement activation.

Accordingly, in some embodiments, the method comprises administering to a patient suffering from or a risk for developing a MASP-2-dependent complement-associated disease or disorder an amount of any of the high-concentration, low-viscosity MASP-2 inhibitory antibody formulations disclosed herein in an amount sufficient to inhibit MASP-2 dependent complement activation in said mammalian subject to thereby treat the disease or disorder. In some embodiments, the methods can be performed using any of the kits or pre-filled containers (e.g., pre-filled syringes or vials) described herein. In some embodiments, the method can further comprise, prior to administering the formulation to the patient, determining that the patient is afflicted with the lectin complement-associated disease or disorder. In some embodiments, the method further comprises administering a tissue permeability modifier (e.g., hyaluronidase) that increases the absorption or dispersion of the MASP-2 inhibitory antibody following parenteral administration. The tissue permeability modifier may be co-administered with the MASP-2 inhibitory antibody formulation or administered sequentially (e.g., within 5 minutes of administering the MASP-2 inhibitory antibody formulation at or near the same injection site).

In some embodiments, the method comprises injecting a subject in need thereof from a first prefilled syringe containing a high concentration low viscosity formulation comprising MASP-2 inhibitory antibody (e.g., OMS646) to inhibit MASP-2-dependent complement activation. In some embodiments, the method further comprises injecting the subject from a second pre-filled syringe containing a tissue permeability modifier, wherein the injection is at or near the site of the injection with the MASP-2 inhibitory antibody.

In some embodiments, the MASP-2-dependent complement-associated disease or disorder is a thrombotic microangiopathy (TMA) including thrombotic thrombocytopenic purpura (TTP), refractory TTP, Upshaw-Schulman Syndrome (USS), hemolytic uremic syndrome (HUS), atypical hemolytic syndrome (aHUS), non-Factor H-dependent atypical hemolytic syndrome, aHUS secondary to an infection, plasma therapy-resistant aHUS, a TMA secondary to cancer, a TMA secondary to chemotherapy, a TMA secondary to transplantation, or a TMA associated with hematopoietic stem cell transplant.

In some embodiments, the MASP-2-dependent complement-associated disease or disorder is a renal condition including, but not limited to, mesangioproliferative glomerulonephritis, membranous glomerulonephritis, membranoproliferative glomerulonephritis (mesangiocapillary glomerulonephritis), acute post infectious glomerulonephritis (poststreptococcal glomerulonephritis), C3 glomerulopathy, cryoglobulinemic glomerulonephritis, pauci-immune necrotizing crescentic glomerulonephritis, lupus nephritis, Henoch-Schonlein purpura nephritis and IgA nephropathy.

In some embodiments, the MASP-2-dependent complement-associated disease or disorder is renal fibrosis (e.g., tubulointerstitial fibrosis) and/or proteinuria in a subject suffering from or at risk for developing chronic kidney disease, chronic renal failure, glomerular disease (e.g., focal segmental glomerulosclerosis), an immune complex disorder (e.g., IgA nephropathy, membranous nephropathy), lupus nephritis, nephrotic syndrome, diabetic nephropathy, tubulointerstitial damage and glomerulonepthritis (e.g., C3 glomerulopathy), or a disease or condition associated with proteinuria, including, but not limited to nephrotic syndrome, pre-eclampsia, eclampsia, toxic lesions of kidneys, amyloidosis, collagen vascular diseases (e.g., systemic lupus erythematosus), dehydration, glomerular diseases (e.g., membranous glomerulonephritis, focal segmental glomerulonephritis, C3 glomerulopathy, minimal change disease, lipoid nephrosis), strenuous exercise, stress, benign orthostatis (postural) proteinuria, focal segmental glomerulosclerosis, IgA nephropathy (i.e., Berger's disease), IgM nephropathy, membranoproliferative glomerulonephritis, membranous nephropathy, minimal change disease, sarcoidosis, Alport's syndrome, diabetes mellitus (diabetic nephropathy), drug-induced toxicity (e.g., NSAIDS, nicotine, penicillamine, lithium carbonate, gold and other heavy metals, ACE inhibitors, antibiotics (e.g., adriamycin) or opiates (e.g., heroin) or other nephrotoxins); Fabry's disease, infections (e.g., HIV, syphilis, hepatitis A, B or C, poststreptococcal infection, urinary schistosomiasis); aminoaciduria, Fanconi syndrome, hypertensive nephrosclerosis, interstitial nephritis, sickle cell disease, hemoglobinuria, multiple myeloma, myoglobinuria, organ rejection (e.g., kidney transplant rejection), ebola hemorrhagic fever, Nail patella syndrome, familial mediterranean fever, HELLP syndrome, systemic lupus erythematosus, Wegener's granulomatosis, Rheumatoid arthritis, Glycogen storage disease type 1, Goodpasture's syndrome, Henoch-Schönlein purpura, urinary tract infection which has spread to the kidneys, Sjögren's syndrome and post-infections glomerulonepthritis.

In some embodiments, the MASP-2-dependent complement-associated disease or disorder is an inflammatory reaction resulting from tissue or solid organ transplantation including, but not limited to, allotransplantation or xenotransplantation of whole organs (e.g., kidney, heart, liver, pancreas, lung, cornea, and the like) or tissue grafts (e.g., valves, tendons, bone marrow, and the like).

In some embodiments, the MASP-2-dependent complement-associated disorder is an ischemia reperfusion injury (I/R), including but not limited to, myocardial FR, gastrointestinal I/R, renal I/R, and FR following an aortic aneurism repair, FR associated with cardiopulmonary bypass, cerebral I/R, stroke, organ transplant or reattachment of severed or traumatized limbs or digits; revascularization to transplants and/or replants, and hemodynamic resuscitation following shock and/or surgical procedures.

In some embodiments, the MASP-2-dependent complement-associated disease or disorder is a complication associated with non-obese diabetes (Type-1 diabetes or Insulin-dependent diabetes mellitus) and/or complications associated with Type-1 or Type-2 (adult onset) diabetes including, but not limited to diabetic angiopathy, diabetic neuropathy, diabetic retinopathy or diabetic macular edema.

In some embodiments, the MASP-2-dependent complement-associated disease or disorder is a cardiovascular disease or disorder, including but not limited to, Henoch-Schonlein purpura nephritis, systemic lupus erythematosus-associated vasculitis, vasculitis associated with rheumatoid arthritis (also called malignant rheumatoid arthritis), immune complex vasculitis, and Takayasu's disease; dilated cardiomyopathy; diabetic angiopathy; Kawasaki's disease (arteritis); venous gas embolus (VGE); and inhibition of restenosis following stent placement, rotational atherectomy and/or percutaneous transluminal coronary angioplasty (PTCA).

In some embodiments, the MASP-2-dependent complement-associated disease or disorder is an inflammatory gastrointestinal disorder, including but not limited to, pancreatitis, diverticulitis and bowel disorders including Crohn's disease, ulcerative colitis, irritable bowel syndrome and inflammatory bowel disease (IBD).

In some embodiments, the MASP-2-dependent complement-associated disease or disorder is a pulmonary disorder, including but not limited to, acute respiratory distress syndrome, transfusion-related acute lung injury, ischemia/reperfusion acute lung injury, chronic obstructive pulmonary disease, asthma, Wegener's granulomatosis, antiglomerular basement membrane disease (Goodpasture's disease), meconium aspiration syndrome, aspiration pneumonia, bronchiolitis obliterans syndrome, idiopathic pulmonary fibrosis, acute lung injury secondary to burn, non-cardiogenic pulmonary edema, transfusion-related respiratory depression and emphysema.

In some embodiments, the MASP-2-dependent complement-associated disease or disorder is a extracorporeal exposure-triggered inflammatory reaction and the method comprises treating a subject undergoing an extracorporeal circulation procedure including, but not limited to, hemodialysis, plasmapheresis, leukopheresis, extracorporeal membrane oxygenation (ECMO), heparin-induced extracorporeal membrane oxygenation LDL precipitation (HELP) and cardiopulmonary bypass (CPB).

In some embodiments, the MASP-2-dependent complement-associated disease or disorder is inflammatory or non-inflammatory arthritides and other musculoskeletal disorders, including but not limited to, osteoarthritis, rheumatoid arthritis, juvenile rheumatoid arthritis, gout, neuropathic arthropathy, psoriatic arthritis, ankylosing spondylitis or other spondyloarthropathies and crystalline arthropathies, muscular dystrophy and systemic lupus erythematosus (SLE).

In some embodiments, the MASP-2-dependent complement-associated disease or disorder is a skin disorder, including, but not limited to, psoriasis, autoimmune bullous dermatoses, eosinophilic spongiosis, bullous pemphigoid, epidermolysis bullosa acquisita, atopic dermatitis, herpes gestationis and other skin disorders, and for the treatment of thermal and chemical burns including capillary leakage caused thereby.

In some embodiments, the MASP-2-dependent complement-associated disease or disorder is a peripheral nervous system (PNS) and/or central nervous system (CNS) disorder or injury including, but not limited to, multiple sclerosis (MS), myasthenia gravis (MG), Huntington's disease (HD), amyotrophic lateral sclerosis (ALS), Guillain Barre syndrome, reperfusion following stroke, degenerative discs, cerebral trauma, Parkinson's disease (PD), Alzheimer's disease (AD), Miller-Fisher syndrome, cerebral trauma and/or hemorrhage, traumatic brain injury, demyelination and meningitis.

In some embodiments, the MASP-2-dependent complement-associated disease or disorder is sepsis or a condition resulting from sepsis including without limitation severe sepsis, septic shock, acute respiratory distress syndrome resulting from sepsis, hemolytic anemia, systemic inflammatory response syndrome, or hemorrhagic shock.

In some embodiments, the MASP-2-dependent complement-associated disease or disorder is a urogenital disorder including, but not limited to, painful bladder disease, sensory bladder disease, chronic abacterial cystitis and interstitial cystitis, male and female infertility, placental dysfunction and miscarriage and pre-eclampsia.

In some embodiments, the MASP-2-dependent complement-associated disease or disorder is an inflammatory reaction in a subject being treated with chemotherapeutics and/or radiation therapy, including without limitation for the treatment of cancerous conditions.

In some embodiments, the MASP-2-dependent complement-associated disease or disorder is an angiogenesis-dependent cancer, including but not limited to, a solid tumor(s), blood borne tumor(s), high-risk carcinoid tumors and tumor metastases.

In some embodiments, the MASP-2-dependent complement-associated disease or disorder is an angiogenesis-dependent benign tumor, including but not limited to hemangiomas, acoustic neuromas, neurofibromas, trachomas, carcinoid tumors and pyogenic granulomas.

In some embodiments, the MASP-2-dependent complement-associated disease or disorder is an endocrine disorder including, but not limited to, Hashimoto's thyroiditis, stress, anxiety and other potential hormonal disorders involving regulated release of prolactin, growth or insulin-like growth factor, and adrenocorticotropin from the pituitary.

In some embodiments, the MASP-2-dependent complement-associated disease or disorder is an ophthalmic disease or disorder including, but not limited to age-related macular degeneration, glaucoma and endophthalmitis.

In some embodiments, the MASP-2-dependent complement-associated disease or disorder is an ocular angiogenic disease or condition including, but not limited to age-related macular degeneration, uveitis, ocular melanoma, corneal neovascularization, primary pterygium, HSV stromal keratitis, HSV-1-induced corneal lymphangiogenesis, proliferative diabetic retinopathy, diabetic macular edema, retinopathy of prematurity, retinal vein occlusion, corneal graft rejection, neovascular glaucoma, vitreous hemorrhage secondary to proliferative diabetic retinopathy, neuromyelitis optica and rubeosis.

In some embodiments, the MASP-2-dependent complement-associated disease or disorder is disseminated intravascular coagulation (DIC) or other complement mediated coagulation disorder, including DIC secondary to sepsis, severe trauma, including neurological trauma (e.g., acute head injury, see Kumura et al., *Acta Neurochirurgica* 85:23-28 (1987), infection (bacterial, viral, fungal, parasitic), cancer, obstetrical complications, liver disease, severe toxic reaction (e.g., snake bite, insect bite, transfusion reaction), shock, heat stroke, transplant rejection, vascular aneurysm, hepatic failure, cancer treatment by chemotherapy or radiation therapy, burn, or accidental radiation exposure.

In some embodiments, the MASP-2-dependent complement-associated disease or disorder is selected from the group consisting of acute radiation syndrome, dense deposit disease, Degos Disease, Catastrophic Antiphospholipid Syndrome (CAPS), Behcet's disease, cryoglobulinemia; paroxysmal nocturnal hemoglobinuria ("PNH") and cold agglutinin disease.

In some embodiments, the MASP-2-dependent complement-associated disease or disorder is selected from the group consisting of aHUS, HSCT-TMA, IgAN, and Lupus Nepthritis (LN).

Atypical Hemolytic Uremic Syndrome (aHUS)

Atypical hemolytic uremic syndrome (aHUS) is part of a group of conditions termed "Thrombotic microangiopathies." In the atypical form of HUS (aHUS), the disease is associated with defective complement regulation and can be either sporadic or familial. Familial cases of aHUS are associated with mutations in genes coding for complement activation or complement regulatory proteins, including complement factor H, factor I, factor B, membrane cofactor CD46 as well as complement factor H-related protein 1 (CFHR1) and complement factor H-related protein 3 (CFHR3). (Zipfel, P. F., et al., *PloS Genetics* 3(3):e41 (2007)). The unifying feature of this diverse array of genetic mutations associated with aHUS is a predisposition to enhanced complement activation on cellular or tissue surfaces. A subject is a risk for developing aHUS upon the onset of at least one or more symptoms indicative of aHUS (e.g., the presence of anemia, thrombocytopenia and/or renal insufficiency) and/or the presence of thrombotic microangiopathy in a biopsy obtained from the subject. The determination of whether a subject is at risk for developing aHUS comprises determining whether the subject has a genetic predisposition to developing aHUS, which may be carried out by assessing genetic information (e.g. from a database containing the genotype of the subject), or performing at least one genetic screening test on the subject to determine the presence or absence of a genetic marker associated with aHUS (i.e., determining the presence or absence of a genetic mutation associated with aHUS in the genes encoding complement factor H (CFH), factor I (CFI), factor B (CFB), membrane cofactor CD46, C3, complement factor H-related protein 1 (CFHR1), or THBD (encoding the anticoagulant protein thrombodulin) or complement factor H-related protein 3 (CFHR3), or complement factor H-related protein 4 (CFHR4)) either via genome sequencing or gene-specific analysis (e.g., PCR analysis), and/or determining whether the subject has a family history of aHUS. Methods of genetic screening for the presence or absence of a genetic mutation associated with aHUS are well established, for example, see Noris M et al. "Atypical Hemolytic-Uremic Syndrome," 2007 Nov. 16 [Updated 2011 Mar. 10]. In: Pagon R A, Bird T D, Dolan C R, et al., editors. GeneReviews™, Seattle (Wash.): University of Washington, Seattle.

As described in US2015/0166675, in a human ex vivo experimental model of thrombotic microangiopathy (TMA), OMS646 inhibited complement activation and thrombus formation on microvascular endothelial cells exposed to serum samples from aHUS patients in both the acute phase and in remission. As further described in US2017/0137537, data obtained in an open-label Phase 2 clinical trial (i.v. administration of 2-4 mg/kg MASP-2 inhibitory antibody OMS646 once per week for 4 consecutive weeks), treatment with OMS646 showed efficacy in patients with aHUS. Platelet counts in all three aHUS patients in the mid- and high-dose cohorts (two in the mid-dose and one in the high-dose cohort) returned to normal, with a statistically significant mean increase from baseline of approximately 68,000 platelets/mL (p=0.0055).

Hematopoietic Stem Cell Transplant-Associated TMA (HSCT-TMA)

Hematopoietic stem cell transplant-associated TMA (HSCT-TMA) is a life-threatening complication that is triggered by endothelial injury. The kidney is the most commonly affected organ, though HSCT-TMA can be a multisystem disease that also involves the lung, bowel, heart and brain. The occurrence of even mild TMA is associated with long-term renal impairment. Development of post-allogeneic HSCT-associated TMA differs in frequency based on varying diagnostic criteria and conditioning and graft-versus-host disease prophylaxis regimens, with calcineurin inhibitors being the most frequent drugs implicated (Ho V T et al., *Biol Blood Marrow Transplant,* 11(8):571-5, 2005).

As described in US2017/0137537, in an Phase 2 clinical trial (i.v. administration of 4 mg/kg MASP-2 inhibitory antibody OMS646 once per week for 4 to 8 consecutive weeks), treatment with OMS646 improved TMA markers in patients suffering from HSCT-TMA, including a statistically significant improvement in LDH and haptoglobin levels. The HSCT-TMA patients treated with OMS646 represent some of the most difficult to treat, thereby demonstrating clinical evidence of a therapeutic effect of OMS646 in patients with HSCT-TMA.

Immunoglobulin A Nephropathy (IgAN)

Immunoglobulin A nephropathy (IgAN) is an autoimmune kidney disease resulting in intrarenal inflammation and kidney injury. IgAN is the most common primary glomerular disease globally. With an annual incidence of approximately 2.5 per 100,000, it is estimated that 1 in 1400 persons in the U.S. will develop IgAN. As many as 40% of patients with IgAN will develop end-stage renal disease (ESRD). Patients typically present with microscopic hematuria with mild to moderate proteinuria and variable levels of renal insufficiency (Wyatt R. J., et al., *N Engl J Med* 368(25):2402-14, 2013). Clinical markers such as impaired kidney function, sustained hypertension, and heavy proteinuria (over 1 g per day) are associated with poor prognosis (Goto M et al., *Nephrol Dial Transplant* 24(10):3068-74, 2009; Berthoux F. et al., *J Am Soc Nephrol* 22(4):752-61, 2011). Proteinuria is the strongest prognostic factor independent of other risk factors in multiple large observational studies and prospective trials (Coppo R. et al., *J Nephrol* 18(5):503-12, 2005; Reich H. N., et al., *J Am Soc Nephrol* 18(12):3177-83, 2007). It is estimated that 15-20% of patients reach ESRD within 10 years of disease onset if left untreated (D'Amico G., *Am J Kidney Dis* 36(2):227-37, 2000). The diagnostic hallmark of IgAN is the predominance of IgA deposits, alone or with IgG, IgM, or both, in the glomerular mesangium.

As described in US2017/0189525, in a Phase 2 open-label renal trial (i.v. administration of 4 mg/kg MASP-2 inhibitory antibody OMS646 once per week for 12 consecutive weeks), patients with IgA nephropathy that were treated with OMS646 demonstrated a clinically meaningful and statistically significant decrease in urine albumin-to-creatinine ratios (uACRs) throughout the trial and reduction in 24-hour urine protein levels from baseline to the end of treatment.

Lupus Nephritis (LN)

A main complication of systemic lupus erythematosus (SLE) is nephritis, also known as lupus nephritis, which is classified as a secondary form of glomerulonephritis. Up to 60% of adults with SLE have some form of kidney involvement later in the course of the disease (Koda-Kimble et al., Koda-Kimble and Young's Applied Therapeutics: the clinical use of drugs, $10^{th}$ Ed, Lippincott Williams & Wilkins: pages 792-9, 2012) with a prevalence of 20-70 per 100,000 people in the US. Lupus nephritis often presents in patients with other symptoms of active SLE, including fatigue, fever, rash, arthritis, serositis, or central nervous system disease (Pisetsky D. S. et al., *Med Clin North Am* 81(1):113-28, 1997). Some patients have asymptomatic lupus nephritis; however, during regular follow-up, laboratory abnormalities such as elevated serum creatinine levels, low albumin levels, or urinary protein or sediment suggest active lupus nephritis.

As described in U.S. patent application Ser. No. 15/470, 647, in a Phase 2 open-label renal trial (i.v. administration of 4 mg/kg MASP-2 inhibitory antibody OMS646 once per week for 12 consecutive weeks), 4 out of 5 patients with Lupus Nephritis (LN) that were treated with an anti-MASP-2 antibody demonstrated a clinically meaningful decrease in 24-hour urine protein levels from baseline to the end of treatment.

Administration

The high concentration low viscosity MASP-2 inhibitory antibody formulations described herein can be administered to a subject in need of treatment using methods known in the art, such as by single or multiple injections or infusions over a period of time in a suitable manner, e.g., injection or infusion by subcutaneous, intravenous, intraperitoneal, intramuscular. As described herein, parenteral formulations can be prepared in dosage unit form for ease of administration and uniformity of dosage. As used herein the term "unit dosage form" refers to physically discrete units suited as unitary dosages for the subject to be treated; each unit containing a predetermined quantity of active compound calculated to produce the desired therapeutic effect in association with the selected pharmaceutical aqueous solution.

For the prevention or treatment of disease, the appropriate dosage of the MASP-2 inhibitory antibody will depend on the type of disease to be treated, the severity and course of the disease. The antibody is suitably administered to the patient at one time or over a series of treatments. Depending on the type and severity of the disease, the MASP-2 inhibitory antibody can be administered at a fixed dose, or in a milligram per kilogram (mg/kg) dose. Exemplary dosages of the MASP-2 inhibitory antibody contained in the formulations described herein include, e.g., about 0.05 mg/kg to about 20 mg/kg, such as about 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg or 20 mg/kg which can be administered daily, twice weekly, once weekly, bi-weekly, or monthly.

Exemplary fixed dosages of the MASP-2 inhibitory antibody, such as the formulations described herein include, e.g., about 10 mg to about 1000 mg, such as about 50 mg to about 750 mg, such as about 100 mg to about 500 mg, such as about 200 mg to about 400 mg, such as about 200 mg, about 225 mg, about 250 mg, about 275 mg, about 300 mg, about 325 mg, about 350 mg, about 375 mg, or about 400 mg which can be administered daily, twice weekly, once weekly, bi-weekly, or monthly.

With regard to delivery volume of the formulations, the concentration of the antibody in a formulation used for a therapeutic application is determined based on providing the antibody in a dosage and volume that is tolerated by, and of therapeutic value to, the patient. For a therapeutic antibody formulation to be administered by injection, the antibody concentration will be dependent on the injection volume (usually from 0.5 mL to 3 mL). Antibody based therapies can require several mg/kg of dosing per day, per week, per month, or per several months. Accordingly, if a MASP-2 inhibitory antibody is to be provided at 1 mg/kg to 5 mg/kg (e.g., 1 mg/kg, 2 mg/kg, 3 mg/kg, 4 mg/kg or 5 mg/kg) of body weight of the patient, and an average patient weighs 75 kg, then 75 mg to 375 mg of the antibody will need to be delivered in a 0.5 mL to 3.0 mL injection volume. Alternatively, the formulation is provided in a concentration suitable for delivery at more than one injection site per treatment.

In a preferred embodiment in which the concentration of the OMS646 antibody in the formulation is about 185 mg/mL, for a dosage of 1 mg/kg to 5 mg/kg of body weight of the patient (assuming 75 kg), the formulation would be delivered subcutaneously in about 0.40 mL to about 2.0 mL injection volume.

As described herein, the formulations of the present disclosure are suitable for both intravenous (i.v.) dosage and subcutaneous (s.c.) administration.

Depending on the type and severity of the disease, the MASP-2 inhibitory antibody can be administered intravenously at a fixed dose, or in a milligram per kilogram (mg/kg) dose. Exemplary dosages of the MASP-2 inhibitory antibody contained in the formulations described herein can be delivered intravenously by diluting an appropriate amount of the high concentration formulation described herein with a pharmaceutically acceptable diluent prior to administration such that the MASP-2 inhibitory antibody is administered to a human subject at a dosage of e.g., about 0.05 mg/kg to about 20 mg/kg, such as about 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg or 20 mg/kg which can be administered daily, twice weekly, once weekly, bi-weekly, or monthly.

The MASP-2 inhibitory antibody can also be delivered intravenously at a fixed dosage by diluting an appropriate amount of the high concentration formulation described herein with a pharmaceutically acceptable diluent prior to administration such that the MASP-2 inhibitory antibody is administered to a human subject at a dosage of about 10 mg to about 1000 mg, such as about 50 mg to about 750 mg, such as about 100 mg to about 500 mg, such as about 200 mg to about 400 mg, such as about 200 mg, about 225 mg, about 250 mg, about 275 mg, about 300 mg, such as about 300 mg to about 400 mg, such as about 310 mg, about 320 mg, about 325 mg, about 330 mg, about 340 mg, about 350 mg, about 360 mg, about 370 mg, about 375 mg, about 380 mg, about 390 mg or about 400 mg which can be administered daily, twice weekly, once weekly, bi-weekly, or monthly.

In some embodiments, the formulation comprising the MASP-2 inhibitory antibody is diluted into a pharmaceutically-acceptable diluent prior to systemic (e.g., intravenous) delivery. Exemplary diluents which can be used include water for injection, 5% dextrose, 0.9% saline, Ringers solution and other pharmaceutically-acceptable diluents suitable for intravenous delivery. While in no way intended to be limiting, exemplary dosages of a MASP-2 inhibitory antibody to be administered intravenously to treat a subject suffering from a MASP-2-dependent complement disease or disorder include, e.g., about 0.05 mg/kg to about 20 mg/kg, such as about 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg or 20 mg/kg which can be administered daily, twice weekly, once weekly, bi-weekly, or monthly. Exemplary fixed dosages of the MASP-2 inhibitory antibody to be delivered intravenously to treat a subject suffering from a MASP-2-dependent complement disease or disorder include, e.g., about 10 mg to about 1000 mg, such as about 50 mg to about 750 mg, such as about 100 mg to about 500 mg, such as about 200 mg to about 400 mg, such as about 200 mg, about 225 mg, about 250 mg, about 275 mg, about 300 mg, about 325 mg, about 350 mg, about 375 mg, or about 400 mg which can be administered daily, twice weekly, once weekly, bi-weekly, or monthly.

In some embodiments, the formulation is diluted into a pharmaceutically acceptable diluent and administered to a subject in need thereof with an initial i.v. loading dose (e.g., about 300 mg to about 750 mg, such as about 400 mg to about 750 mg, such as about 300 mg to about 500 mg, such as about 300 mg to about 400 mg, such as about 300 mg, about 310 mg, about 320 mg, about 330 mg, about 340 mg, about 350 mg, about 360 mg, about 370 mg, about 380 mg, about 390 mg, or about 400 mg), followed by one or more subcutaneous injections of the formulation with a dosage of 1 mg/kg to 5 mg/kg of body weight, or a fixed dosage of about 100 mg to about 400 mg, such as about 100 mg, about 150 mg, about 200 mg, about 250 mg, about 300 mg, about 350 mg, or about 400 mg. For example, an initial i.v. loading dose may be the preferred administration route in particular instances, such as when a patient is in the hospital or in a clinic and suffering from an acute condition (e.g., aHUS) that requires an initial loading dose followed by maintenance dosing with subcutaneous injection of the formulation.

EXAMPLES

The invention is further illustrated in the following examples, which should not be construed as further limiting. All literature citations herein are expressly incorporated by reference.

Example 1

This Example demonstrates that OMS646, a monoclonal antibody targeting human MASP-2, binds to human MASP-2 with high affinity and blocks the lectin pathway complement activity.

BACKGROUND

A fully human monoclonal antibody targeting human MASP-2 (set forth as SEQ ID NO:1), referred to as "OMS646" was generated as described in WO2012/151481, which is hereby incorporated herein by reference. The OMS646 monoclonal antibody comprises a heavy chain variable region (VH) set forth as SEQ ID NO:2 and a light chain variable region (VL) set forth as SEQ ID NO:3. OMS646 is comprised of variable regions of human origin fused to human IgG4 heavy chain and lambda light chain constant regions and is secreted as a disulfide-linked glycosylated tetramer consisting of two identical heavy chains (having the amino acid sequence set forth as 4) and two identical lambda light chains (having the amino acid sequence set forth as SEQ ID NO:5). The Asparagine residue (N) at position 295 of the heavy chain (SEQ ID NO:4) is glycosylated and is indicated in bold and underlined text.

Heavy Chain Variable Region
Presented below is the heavy-chain variable region (VH) sequence for OMS646. The Kabat CDRs (31-35 (H1), 50-65 (H2) and 95-107 (H3)) are bolded; and the Chothia CDRs (26-32 (H1), 52-56 (H2) and 95-101 (H3)) are underlined.

```
OMS646 heavy chain variable region (VH)
                                         (SEQ ID NO: 2)
QVTLKESGPVLVKPTETLTLTCTVSGFSLSRGKMGVSWIRQPPGKALEWL
AHIFSSDEKSYRTSLKSRLTISKDTSKNQVVLTMTNMDPVDTATYYCARI
RRGGIDYWGQGTLVTVSS
```

Light Chain Variable Region
Presented below is the light-chain variable region (VL) sequence for OMS646. The Kabat CDRs (24-34 (L1); 50-56 (L2) and 89-97 (L3) are underlined. These regions are the same whether numbered by the Kabat or Chothia system.

```
OMS646 light chain variable region (VL)
                                         (SEQ ID NO: 3)
QPVLTQPPSLSVSPGQTASITCSGEKLGDKYAYWYQQKPGQSPVLVMYQD
KQRPSGIPERFSGSNSGNTATLTISGTQAMDEADYYCQAWDSSTAVFGGG
TKLTVL OMS646 heavy chain IgG4 mutated heavy chain full
length polypeptide (445 aa)
                                         (SEQ ID NO: 4)
QVTLKESGPVLVKPTETLTLTCTVSGESLSRGKMGVSWIRQPPGKALEWL

AHIFSSDEKSYRTSLKSRLTISKDTSKNQVVLTMTNMDPVDTATYYCARI

RRGGIDYWGQGTLVTVSSASTKGPSVFPLAPCSRSTSESTAALGCLVKDY

FPEPVTVSWNSGALTSGVHTFPAVLQSSGLYSLSSVVTVPSSSLGTKTYT

CNVDHKPSNTKVDKRVESKYGPPCPPCPAPEFLGGPSVFLEPPKPKDTLM
```

-continued

ISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK

OMS646 light chain full length polypeptide (212 aa)
(SEQ ID NO: 5)

QPVLTQPPSLSVSPGQTASITCSGEKLGDKYAYWYQQKPGQSPVLVMYQD

KQRPSGIPERFSGSNSGNTATLTISGTQAMDEADYYCQAWDSSTAVEGGG

TKLTVLGQPKAAPSVTLEPPSSEELQANKATLVCLISDFYPGAVTVAWKA

DSSPVKAGVETTTPSKQSNNKYAASSYLSLTPEQWKSHRSYSCQVTHEGS

TVEKTVAPTECS

As described in WO2012/151481, OMS646 binds to MASP-2 and selectively inhibits the lectin pathway and does not substantially inhibit the classical pathway (i.e., inhibits the lectin pathway while leaving the classical complement pathway intact) and also exhibits at least one or more of the following characteristics: said antibody binds human MASP-2 with a $K_D$ of 10 nM or less, said antibody binds an epitope in the CCP1 domain of MASP-2, said antibody inhibits C3b deposition in an in vitro assay in 1% human serum at an $IC_{50}$ of 10 nM or less, said antibody inhibits C3b deposition in 90% human serum with an $IC_{50}$ of 30 nM or less, wherein the antibody is an antibody fragment selected from the group consisting of Fv, Fab, Fab', F(ab)$_2$ and F(ab')$_2$ wherein the antibody is a single-chain molecule, wherein said antibody is an IgG2 molecule, wherein said antibody is an IgG1 molecule, wherein said antibody is an IgG4 molecule, wherein the IgG4 molecule comprises a S228P mutation.

As described in WO2012/151481, OMS646 was determined to avidly bind to human MASP-2 (SEQ ID NO:1) with >5000 fold selectivity when compared to C1s, C1r, MASP-1 or MASP-3. As shown in this example, OMS646 specifically binds to human MASP-2 with high affinity and has the ability to block lectin pathway complement activity.

As shown above, OMS646 comprises (a) a heavy-chain variable region comprising (i) CDR-H1 comprising the amino acid sequence from 31-35 of SEQ ID NO:2, ii) CDR-H2 comprising the amino acid sequence from 50-65 of SEQ ID NO:2, and iii) CDR-H3 comprising the amino acid sequence from 95-107 of SEQ ID NO:2; and (b) a light-chain variable region comprising: i) CDR-L1 comprising the amino acid sequence from 24-34 of SEQ ID NO:3, ii) CDR-L2 comprising the amino acid sequence from 50-56 of SEQ ID NO:3, and iii) CDR-L3 comprising the amino acid sequence from 89-97 of SEQ ID NO:3.

As further described in WO2012/151481, a variant of OMS646, having a heavy chain variable region with at least 95% identity to SEQ ID NO:2 and a light chain variable region with at least 95% identity to SEQ ID NO:3 was demonstrated to have functional activity similar to OMS646. The OMS646 variant described in WO2012/151481 comprises a) a heavy chain variable region comprising: SEQ ID NO:2, or a variant thereof comprising an amino acid sequence having at least 95% identity to SEQ ID NO:2, wherein residue 31 is an R, residue 32 is a G, residue 33 is a K, residue 34 is an M, residue 35 is a G, residue 36 is a V, residue 37 is an S, residue 50 is an L, residue 51 is an A, residue 52 is an H, residue 53 is an I, residue 54 is an F, residue 55 is an S, residue 56 is an S, residue 57 is a D, residue 58 is an E, residue 59 is a K, residue 60 is an S, residue 61 is a Y, residue 62 is an R, residue 63 is a T, residue 64 is an S, residue 65 is an L, residue 66 is a K, residue 67 is an S, residue 95 is a Y, residue 96 is a Y, residue 97 is a C, residue 98 is an A, residue 99 is an R, residue 100 is an I, residue 101 is an R, residue 102 is an R or A, residue 103 is a G, residue 104 is a G, residue 105 is an I, residue 106 is a D and residue 107 is a Y; and b) a light chain variable region comprising: SEQ ID NO:3 or a variant thereof comprising an amino acid sequence having at least 95% identity to SEQ ID NO:3, wherein residue 23 is an S, residue 24 is a G, residue 25 is an E or D, residue 26 is a K, residue 27 is an L, residue 28 is a G, residue 29 is a D, residue 30 is a K, residue 31 is a Y or F, residue 32 is an A, residue 33 is a Y, residue 49 is a Q, residue 50 is a D, residue 51 is a K or N, residue 52 is a Q or K, residue 53 is an R, residue 54 is a P, residue 55 is an S, residue 56 is a G, residue 88 is a Q, residue 89 is an A, residue 90 is a W, residue 91 is a D, residue 92 is an S, residue 93 is an S, residue 94 is a T, residue 95 is an A, residue 96 is a V and residue 97 is an F.

1. OMS646 Specifically Blocks Lectin-Dependent Activation of Terminal Complement Components Methods:

The effect of OMS646 on membrane attack complex (MAC) deposition was analyzed using pathway-specific conditions for the lectin pathway, the classical pathway and the alternative pathway. For this purpose, the Wieslab Comp300 complement screening kit (Wieslab, Lund, Sweden) was used following the manufacturer's instructions.

Figure 1B:
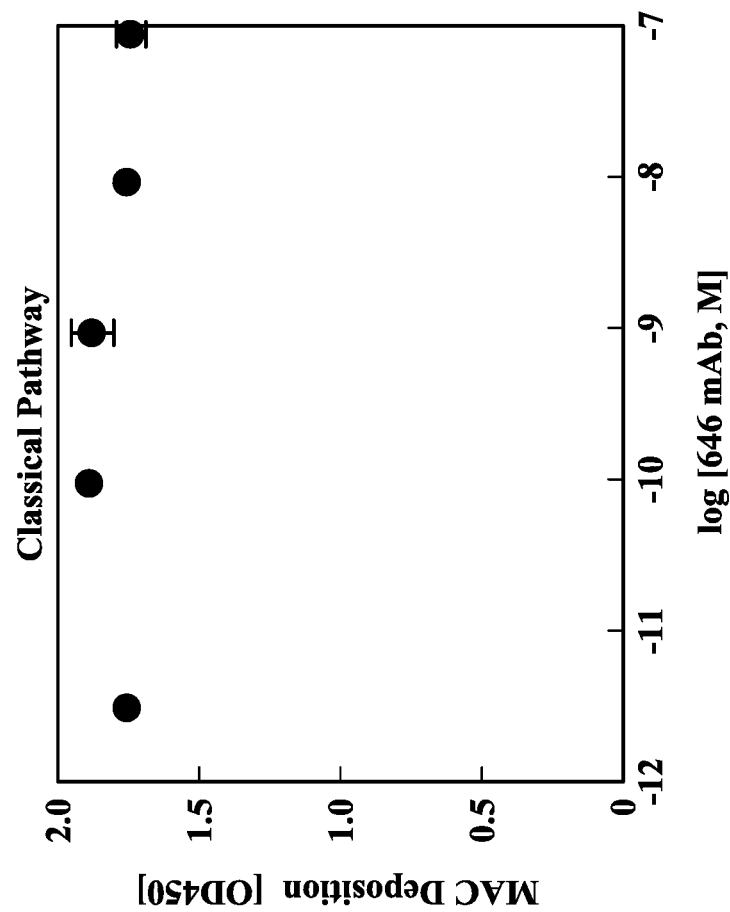
FIG. 1B graphically illustrates the amount of classical pathway-dependent MAC deposition in the presence of different amounts of human MASP-2 monoclonal antibody (OMS646), demonstrating that OMS646 does not inhibit classical pathway-mediated MAC deposition, as described in Example 1.
Figure 1C:
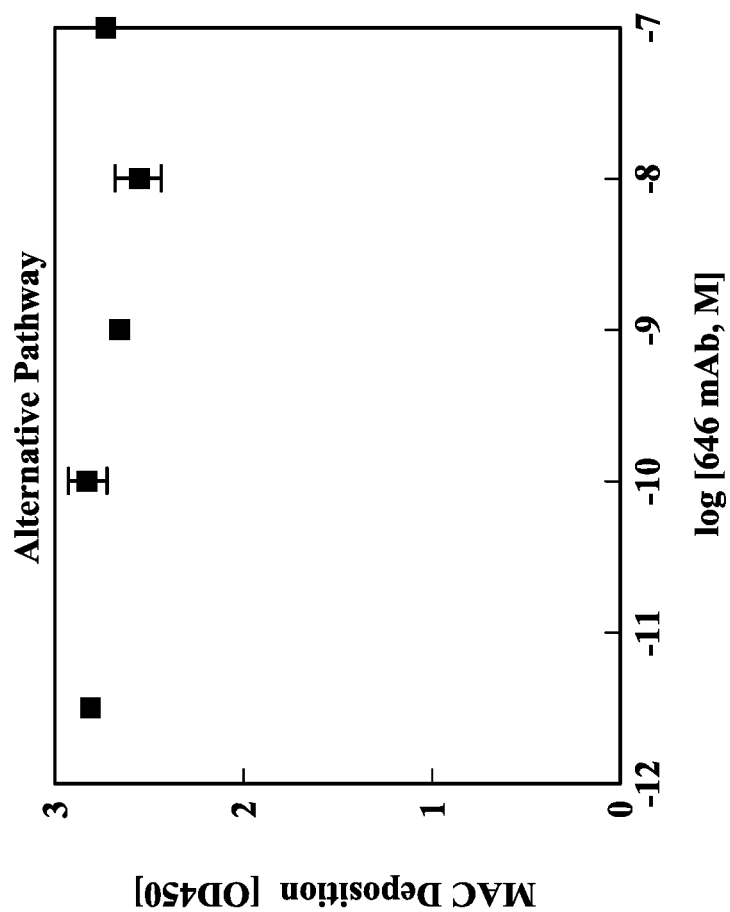
FIG. 1C graphically illustrates the amount of alternative pathway-dependent MAC deposition in the presence of human MASP-2 monoclonal antibody (OMS646), demonstrating that OMS646 does not inhibit alternative pathway-mediated MAC deposition, as described in Example 1.

Results:

FIG. 1A graphically illustrates the amount of lectin pathway-dependent MAC deposition in the presence of different amounts of human MASP-2 inhibitory antibody (OMS646). FIG. 1B graphically illustrates the amount of classical pathway-dependent MAC deposition in the presence of human MASP-2 inhibitory antibody (OMS646). FIG. 1C graphically illustrates the amount of alternative pathway-dependent MAC deposition in the presence of different amounts of human MASP-2 inhibitory antibody (OMS646). As shown in FIG. 1A, OMS646 blocks lectin pathway-mediated activation of MAC deposition with an $IC_{50}$ value of approximately 1 nM. However, OMS646 had no effect on MAC deposition generated from classical pathway-mediated activation (FIG. 1B) or from alternative pathway-mediated activation (FIG. 1C).

Example 2

OMS646 Pre-Formulation Studies

Background/Rationale:

The composition of a reduced viscosity protein formulation is determined by consideration of several factors including, but not limited to: the nature of the protein, the concentration of the protein, the desired pH range, the temperature at which the protein formulation is to be stored, the period of time over which the protein formulation is to be stored, and how the formulation is to be administered to a patient. For a reduced viscosity formulation to be administered by injection, the protein concentration is dependent upon the injection volume (usually 1.0 mL to 2.25 mL). If a protein is to be provided at 2 to 4 mg/kg of body weight of a patient, and an average patient weighs 75 kg, then 150 mg-300 mg of the protein will need to be delivered in a 1.0 mL to 1.62 mL injection volume. Viscosity is ideally maintained below about 25 cP to ensure a realistically syringeable subcutaneous therapeutic product. In some embodiments, viscosity is maintained below about 20 cP to allow for delivery of the therapeutic product with an injection device, and also to allow for various types of bioprocessing, such as tangential flow filtration.

The primary aim of these studies was to identify formulation components that would result in optimal chemical, physical, and structural stability of OMS646 antibody in liquid formulation resulting in a stable formulation with a viscosity of less than 25 cP, such as less than 20 cP, with a high concentration of OMS646 (100 mg/mL or greater) suitable for subcutaneous injection into a human subject.

Analytic Methods:

To test various buffer and excipient combinations, a purified preparation of OMS646 antibody (102 mg/mL in 20 mM sodium acetate, 50 mg/mL sorbitol, pH 5.0) was diluted to ~1 mg/mL in the selected formulation solutions and 4 mL volumes were placed in concentrators pre-rinsed with the appropriate buffer. Each unit was spun down to ~1 mL at 3200×g. This process was repeated for a total of three rounds of buffer-exchange.

Formulation appearance was evaluated using an Eisai Machinery Observation Lamp, Model MIH-DX against water using white and black backgrounds. Each formulation sample was tested for color, clarity (opalescence), and the presence of particulate matter.

The protein content of OMS646 formulations was determined using an extinction coefficient of 1.49 mL/mg*cm. Measurement of absorbance at 280 nm with correction for absorbance at 320 nm was performed using disposable UVettes and a path length of 0.2 cm. Samples were prepared in duplicate by dilution with 1× Dulbecco's Phosphate-Buffered Saline (DPBS) to a final concentration of ~2 mg/mL. For high concentration samples, the neat solutions were first diluted 1:1 in formulation buffer, and then diluted to ~2 mg/mL in 1×DPBS. Duplicate measurements for each sample were averaged, and the percent relative standard deviation (RSD) was calculated. For any duplicate samples displaying >5% RSD, an additional dilution set was prepared and measured.

The protein concentration was calculated as follows:

Corrected $A280 = A280 - A320$

Protein Concentration(mg/mL) = (Corrected $A280$ * Dilution Factor)/1.49 mL/mg*cm To assess sample turbidity/light scattering, 100 µL of undiluted sample was measured at 320 nm in a disposable UVette using a 1 cm path length. For each sample, the spectrophotometer was blanked with the appropriate buffer-exchange solution without the protein present. Following measurement, samples were recovered and used for pH analysis. In order to normalize turbidity measurements for sample concentration, A320 was also divided by the concentration in mg/mL and the resulting value in mAU*mL/mg was reported.

pH measurements of all formulations and solutions were performed at room temperature using a calibrated Seven-Multi Meter (Mettler Toledo) with an automatic temperature compensation electrode.

The thermal stability of the OMS646 formulations was monitored by differential scanning calorimetry (DSC). Melting temperature ($T_m$) data for the mAb were collected using a MicroCal Capillary DSC. The protein samples were diluted to a final concentration of ~2 mg/ml in the appropriate buffer-exchange solution. Evaluation of the samples by DSC was performed by scanning from 20-110° C. at 1° C./minute or 2° C./minute. The pre-scan thermostat was set to 10 minutes, post-scan thermostat to 0 minutes, and the post-cycle thermostat set to 25° C. For $T_m$ data analysis, a buffer-buffer scan was subtracted from the buffer-sample scan and the thermogram was then normalized to protein concentration (molar) using a molecular weight estimate of 150 kDa. A progressive baseline was generated and subtracted from the data to facilitate Tm determination. Melting temperatures were determined using the pick peaks function of the associated Origin® scientific software.

Dynamic light scattering (DLS) measures time-dependent fluctuations in the intensity of scattered light from particles in a sample, where the Stokes Einstein equation is used to calculate the hydrodynamic radius of the particle(s) in solution. The DLS experiments for OMS646 formulations were performed with duplicate undiluted samples (30-40 µL) using a DynaPro™ Plate Reader II instrument (Wyatt). A total of 10 individual scans were performed at 25° C., with an acquisition time of 5 seconds. Viscosity was set to that of phosphate buffered saline, 1.019 cP. The resultant intensity distribution plots were compared to evaluate the effects of various formulation components on mean particle size by intensity (overall diameter), a global size distribution width parameter (overall percent polydispersity, or % Pd), the average peak diameter of the OMS646 monomer (Peak 2 diameter), and that peak's width parameter (Peak 2% Pd). Percent polydispersity (overall or Peak 2) is a width parameter that reflects the heterogeneity detected in the intensity distribution plot, where % Pd<20% is indicative of a near monodisperse solution and/or species conformation.

Stability against chemical denaturation was evaluated using the AVIA Isothermal Chemical Denaturation System (Model 2304), which tests chemical stability under ambient conditions in an automated fashion by generating a denaturant gradient by mixing constant volumes of formulated protein with formulation buffer and formulation buffer containing urea. Briefly, formulated protein was diluted to 0.33 mg/mL in formulation buffer. For a given formulation, a second formulation buffer containing 10M urea was also prepared. Due to solubility issues, 9M urea solutions were prepared for sucrose- and sorbitol-containing formulations. After a uniform incubation time (~30 minutes), intrinsic protein fluorescence (i.e., tryptophan fluorescence) is measured for each data point, where chemical unfolding of the protein results in exposure of buried tryptophans to solvent with an associated red-shift in the fluorescence signal. For each formulation, data was obtained for a total of 24 urea concentrations (0-9.0M for 10 M urea stocks and 0-8.1M for 9M urea stocks), and the ratio of Abs350/Abs330 was used for baseline subtraction of background fluorescence changes, and a non-linear least squares fit to the unfolding transition data was employed using either a 2-state or 3-state model.

Viscosity of the formulations was determined using either a rolling ball viscometer or a rheometer. All viscosity measurements were performed at 25° C. with a shear rate in the range of 0.5 s$^{-1}$ to 1000 s$^{-1}$. Rolling ball measurements were performed using an Anton Paar AMVn viscometer. For rolling ball viscosity measurements, the time a gold ball takes to pass a distance in a capillary filled with the sample is measured after tilting the capillary to a predefined angle (80 degrees). Capillaries were tilted a total of three times and the results were averaged to determine the final dynamic viscosity, a value which is not dependent on sample density. For rolling ball measurements, the capillary was first cleaned using DI water and methanol. Calibration of the instrument/capillary was confirmed by measurement of 10 cP, 50 cP and/or 100 cP Brookfield viscosity standards. The capillary was re-cleaned with DI water and methanol prior to and between every sample measurement.

Rheometer-based viscosity measurements were performed using a DV-III Ultra Programmable Rheometer which was calibrated with Brookfield Viscosity Standard Fluid #10 and #50. 0.5 mL of each sample was measured at various spindle speeds (shear rates). Samples displaying viscosity (cP) readings with <10% RSD for all shear rates were considered Newtonian over this range, while samples were shear rate-dependent viscosity were considered non-Newtonian.

Density measurements were carried out using an Anton Paar DMA 4500M Densitometer. Briefly, the instrument was flushed with DI water several times followed by methanol. The instrument was calibrated for air and water prior to measuring the density of water as a sample. The instrument was again washed with water and methanol and a single sample measurement was performed on ~175 mg/mL material pooled from several formulations. The reported value was used as a reasonable density approximation for high-concentration OMS646 formulations to be used in gravimetric content measurements.

Osmolality measurements were performed using a freezing point depression osmometer (Multi-Osmette Osmometer, Precision Systems model 2430), which measures the decrease in a solution's freezing point as solute concentration increases.

A liquid particle-counting system (Hach Model 9703, Sensor Model: HRLD-150) was used for determining particle size and abundance in OMS646 formulation samples. Sample data was obtained using a single 500 µL draw of sample (200 µL tare volume). Briefly, the instrument was allowed to warm up for ~30 minutes and both the syringe (1 mL) and system were flushed with deionized water for at least 10 cycles before use. Environment suitability was tested by showing that 25 mL of deionized water contained no more than 25 particles ≥10 µm in size. System suitability was confirmed by analyzing a single 500 µL draw of 2, 5, 10 and 15 standards using appropriate channel sizes. If cumulative counts/mL detected fell within the specification given for the standard, then the system was deemed suitable for sample testing. Before the first sample measurement, the system was flushed once with 1× Phosphate Buffered Saline (PBS) to ensure that samples did not precipitate upon contact with deionized water. Samples were analyzed using a single 500 µL draw, and cumulative counts/mL for 2 µm, 5 µm, 10 µm and 25 µm channels were determined to the nearest whole number.

Size exclusion chromatography (SEC) was used to evaluate the quantity of aggregates and degradation products present in the OMS646 formulations. Briefly, an Agilent 1100 HPLC system was fitted with a G3000SWx1 SEC column (Tosoh, 7.8×300 mm, 5 µm particle size). OMS646 formulation samples were diluted to 2.5 mg/mL in SEC mobile phase (140 mM potassium phosphate, 75 mM potassium chloride, pH 7.0) and 20 µL of sample was injected into the HPLC column. The system was run using a flow rate of 0.4 mL/min, and eluted protein was detected by absorption at 280 nm (bandwidth 4 nm) with no reference correction. To assess system suitability, all samples were bracketed by mobile phase blank and gel filtration standard injections, and reference material was injected in duplicate at the beginning of the sequence. Percent abundances for individual and total high molecular weight (HMW) species and low molecular weight (LMW) species, in addition to percent monomer and total integrated peak area were determined.

Analysis by reduced SDS capillary gel (SDS-CE) electrophoresis was performed with a Beckman Coulter PA 800 Plus capillary electrophoresis system and PDA detection module, using an SDS-MW Analysis Kit. Samples and reference were first diluted to 1.0 mg/mL in SDS-MW Sample Buffer. To 95 µL of this working solution 5 µL of β-mercaptoethanol and 2 µL of Internal Standard (10 kDa) were added. All samples were centrifuged at 300×g for 1 minute, heated at 70±2° C. for ~10 minutes, and transferred to a PCR vial and kept at 25° C. until analysis. Separations were conducted by applying 15 kV (reverse polarity) across the capillary for 30 minutes and applying a 20.0 psi pressure at both inlet and outlet. Data was acquired at 220 nm with a collection rate of 4 Hz. Reference (unprocessed OMS646) was injected twice at the beginning of each sequence. Percent LC, HC and IgG were reported.

Non-reduced SDS capillary gel electrophoresis analyses were carried out as described for reduced CE-SDS, with the exception that freshly prepared 250 mM iodoacetamide was used in place of reducing agent, and separations were performed for 35 minutes. Total electropherogram area and % IgG were reported.

A purified preparation of OMS646 antibody (102 mg/mL) was generated using recombinant methods as described in WO2012/151481, which is hereby incorporated herein by reference. Briefly described, OMS646 antibody was generated in CHO cells containing expression constructs encoding the heavy chain and light chain polypeptides of OMS646 and purified using standard techniques.

1. Comparison of Candidate Buffering Systems:
Methods:

In the pre-formulation studies, the stability of MASP-2 inhibitory antibody OMS646 was initially evaluated against a panel of candidate buffers including those commonly used in therapeutic antibody formulation (citrate, histidine, phosphate), as well as more unconventional buffers (acetate, succinate) in order to cover a wide pH range (pH 4.0-pH 8.0). For this study, the protein was exchanged into 20 mM succinate (pH 4.0, 5.0 and 5.5), acetate (pH 4.0, 5.0 and 5.5), citrate (pH 5.0, 6.0 and 7.0), histidine (pH 6.0 and 7.0) and phosphate (pH 6.0, 7.0 and 8.0) buffers using Amicon Ultra-4 (10 kDa MWCO) concentrators. A purified preparation of OMS646 antibody (102 mg/mL in 20 mM sodium acetate, 50 mg/mL sorbitol, pH 5.0) was diluted to ~1 mg/mL in each of the 14 formulation solutions, and 4.0 mL volumes were placed in concentrators pre-rinsed with the appropriate buffer. Each unit was spun down to ~1 mL at 3200×g. This process was repeated for a total of three rounds of buffer-exchange. During the final round of concentration, the protein was over-concentrated to <1 mL. The approximate volume and centrifuge time of each solution was recorded after each cycle.

Results:

Overall, the data generated for the five buffer types were comparable with regard to buffer-exchange rate, protein content recovery, differential scanning colorimetry (DSC), dynamic light scattering (DLS) and chemical stability (data not shown). Acetate, citrate and histidine were selected for further evaluation based on the apparent overall optimal thermal and conformational OMS646 properties in the pH range 5.5-6.0. Acetate was selected over succinate at pH 5.5 due primarily to superior thermal stability, while histidine and citrate were selected over phosphate at pH 6.0 based upon DLS data.

2. Excipient Screening

The stability of OMS646 was evaluated in the presence of various excipients with reported antibody-stabilizing properties, using buffering systems identified during baseline buffer screening (20 mM acetate, pH 5.5; citrate, pH 6.0, and histidine, pH 6.0). For this study, OMS646 was buffer-exchanged into each candidate buffer containing either 150 mM NaCl, 250 mM sorbitol, 250 mM sucrose, 150 mM L-arginine, 150 mM L-glutamate or 250 mM L-proline using Amicon Ultra-4 (10 kDa MWCO) concentrators. Sample preparation was carried out as described in the buffer system comparison wherein the target protein concentration was 2.0 mg/mL.

Results:

With regard to protein recoveries, the estimated protein recoveries ranged from ~72-106%, which represented a modest improvement over recoveries in the absence of excipient. Histidine buffer appeared to be preferred for the majority of excipients, and acetate and citrate showed mixed results.

Figure 2A:
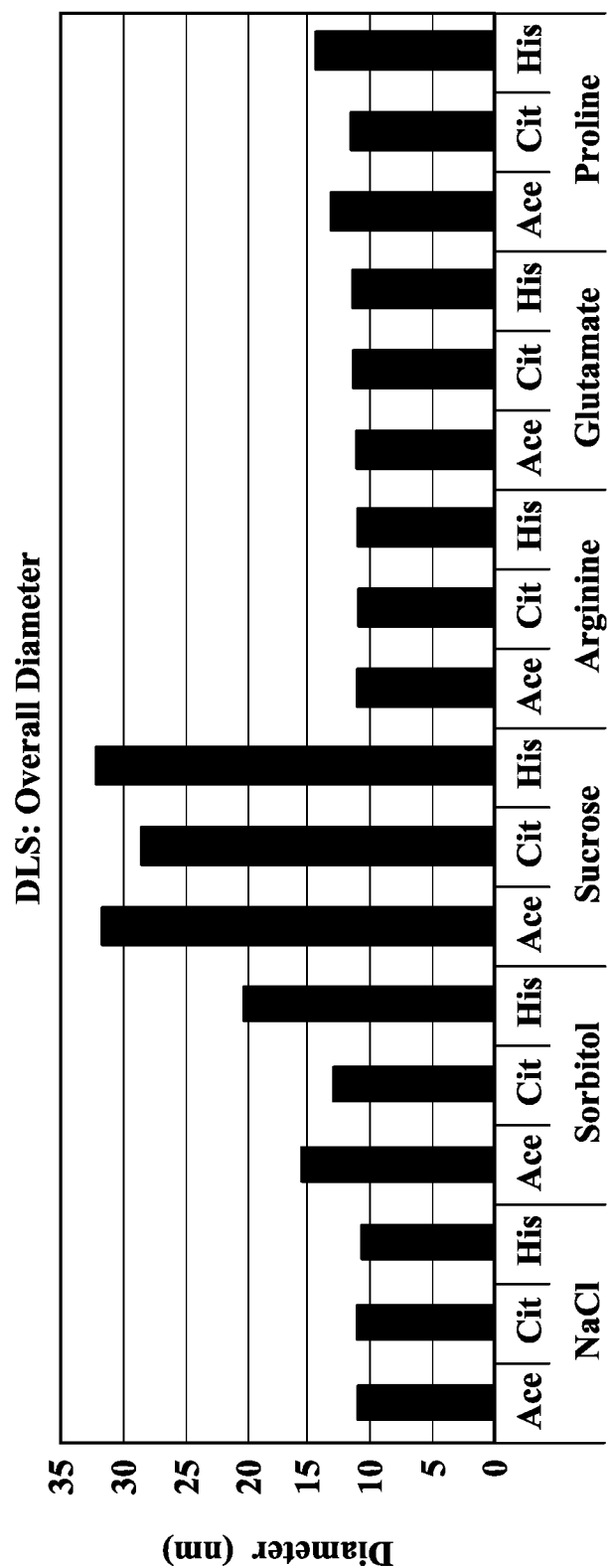
FIG. 2A graphically illustrates the results for Dynamic Light Scattering (DLS) analysis for OMS646 formulation excipient screening, showing the overall particle diameter observed for formulations containing various candidate excipients, as described in Example 2.
Figure 2B:
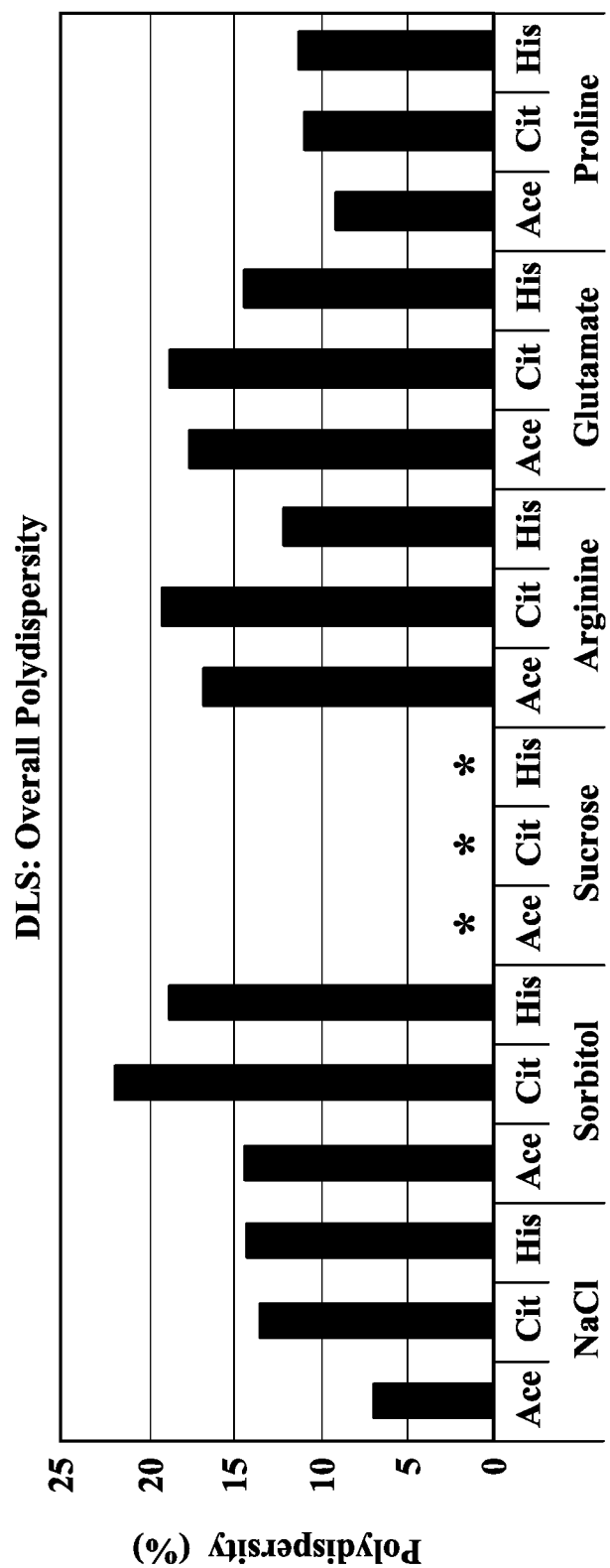
FIG. 2B graphically illustrates the results for DLS analysis for OMS646 formulation excipient screening, showing the overall polydispersity observed for formulations containing various candidate excipients, as described in Example 2.

With regard to DSC, it was observed that citrate buffer resulted in OMS646 thermal stabilization for all excipients tested. FIG. 2A graphically illustrates the results for Dynamic Light Scattering (DLS) analysis for OMS646 formulation excipient screening, showing the overall particle diameter observed for formulations containing various candidate excipients. FIG. 2B graphically illustrates the results for DLS analysis for OMS646 formulation excipient screening, showing the overall polydispersity observed for formulations containing various candidate excipients. As shown in FIGS. 2A and 2B, with regard to DLS, most formulations yielded comparable results. However, for all buffering systems, sucrose was associated with elevated polydispersity and the largest overall and monomeric diameters. Following sucrose, sorbitol was the least preferred by DLS, showing larger mean sizes and increased polydispersity. The remaining formulations were generally comparable by DLS with monomer diameters of 10-12 nm (see FIG. 2A) and polydispersity <20% indicating monodisperse populations (see FIG. 2B). With regard to stability against chemical denaturation, as evaluated using the AVIA Isothermal Chemical Denaturation System, a buffer/pH trend was clearly observed where acetate pH 5.5 formulations denatured at urea concentrations ~0.5 M lower than citrate and histidine pH 6.0 formulations for all excipients tested. Citrate and histidine were comparable for all excipients.

In summary, the data supported citrate at approximately a pH of 6.0 as the optimal buffer/pH combination, which was carried forward into solubility screening studies. Given the poor DLS data observed with all buffer types, sucrose was excluded from further consideration.

3. Solubility/Viscosity Screening

First Viscosity Study:

Methods:

In order to establish conditions for maximum OMS646 solubility, 20 mM citrate (pH 5.0 and 6.0) and 20 mM succinate (pH 4.0) were used in the presence of several isotonic combinations of NaCl, sorbitol, arginine, glutamate and proline. OMS646 was buffer-exchanged using Amicon 15 concentrator units in multiple cycles and on the final cycle the volume of each solution was reduced to ~1 mL. Buffer exchange rates for all formulations and exchange cycles were recorded and analyzed. Following buffer exchange, protein contents were measured, percent recovery was calculated and the samples were stored overnight at 5° C. During storage, the succinate/glutamate formulation was observed to precipitate and was not evaluated further. Remaining formulations were added to Amicon 4 concentrator units and concentrated until a target concentration of ~200 mg/mL was reached, or until centrifugation no longer resulted in volume reduction and/or sample viscosity (via sample manipulation) was deemed to be unmanageable.

Results:

With regard to buffer-exchange rates, the highest exchange rates were clearly observed in pH 4.0 samples, with succinate/sorbitol showing the fastest exchange rates overall. Exchange rates at pH 5.0 and 6.0 were comparable, where formations containing only charged amino acid excipients showed higher rates than other formulations. The slowest exchange rate was observed for the citrate/sorbitol formulation at pH 6.0. This formulation was the lone sample with pH≥5.0 and an uncharged excipient component. Under the assumption that exchange rate is a surrogate indicator for OMS646 self-association, it appears that charged species are important for mitigating this behavior at a more neutral pH. With regard to DLS, all high-concentration formulations showed comparable overall diameters of ~12 nm, with the exception of succinate/arginine pH 4.0 which showed an elevated global size distribution at >18 nM.

Figure 3:
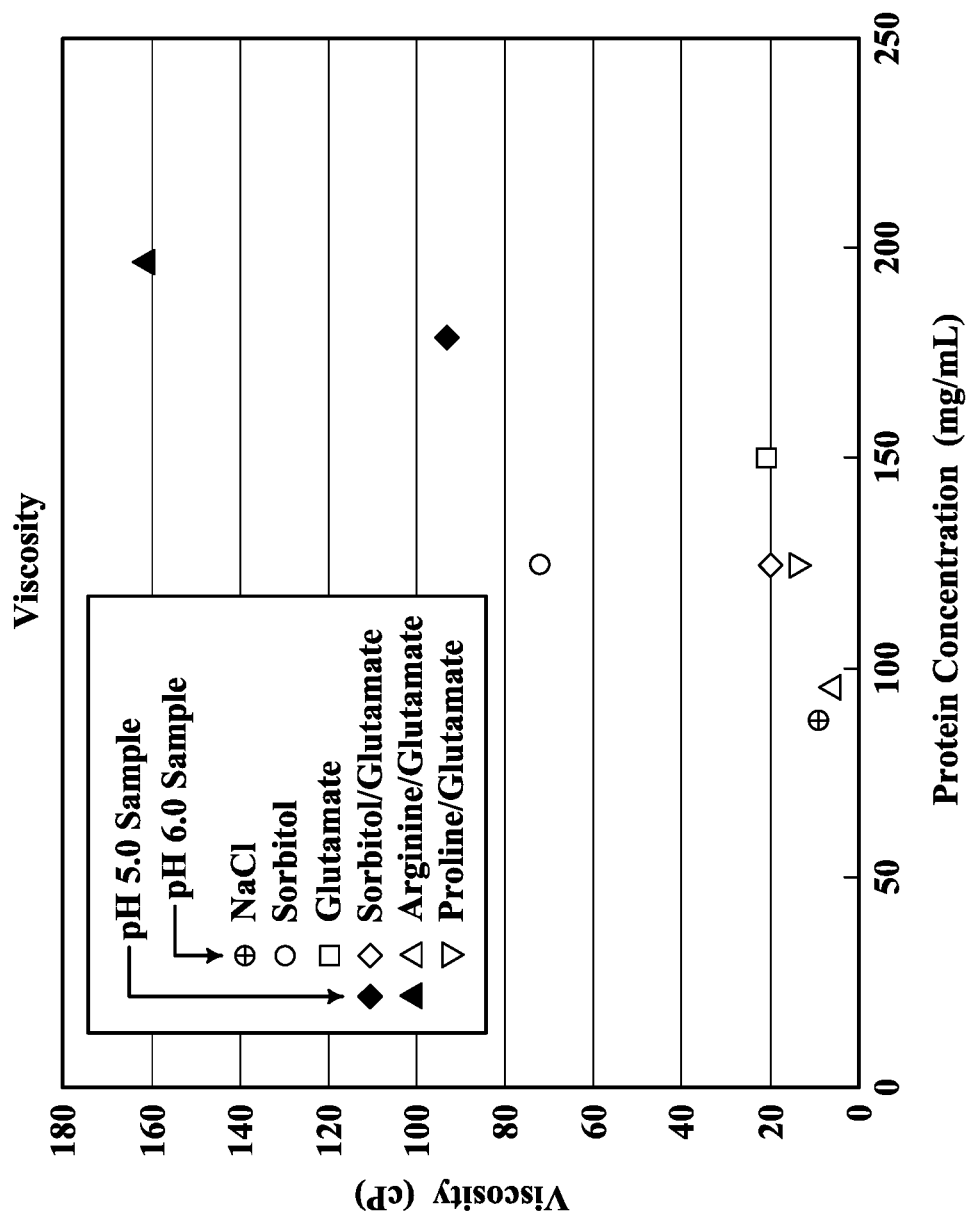
FIG. 3 graphically illustrates the results of viscosity analysis of a range of OMS646 concentrations in various formulations as measured at pH 5.0 and pH 6.0, as described in Example 2.

The buffer-exchanged samples were concentrated until solutions became physically unworkable due to high viscosity. Maximum concentrations in excess of 225 mg/mL were achieved for both pH 4.0 formulations. For formulations at higher pH values, maximal OMS646 protein concentrations ranged from 160.5 to 207.6 mg/mL. Viscosity for the majority of formulations was evaluated using a rolling ball viscometer with a shear rate between 0.5 $s^{-1}$ to 1000 $s^{-1}$ as described above. FIG. 3 graphically illustrates the results of viscosity analysis for OMS646 solubility screening over a range of protein concentrations in various formulations as measured at pH 5.0 and pH 6.0. As shown in FIG. 3, when plotted against protein concentration, an exponential increase in viscosity was observed over the formulations, with the highest viscosity recorded for citrate/arginine/glutamate pH 5.0 (161.1 cP for a 196.6 mg/mL solution). At pH 6.0 and a comparable OMS646 protein concentration, the citrate/sorbitol formulation showed considerably higher viscosity than either the sorbitol/glutamate or proline/glutamate formulation. The citrate/arginine/glutamate pH 6.0 formulation (95.3 mg/mL) displayed approximately half the viscosity (5.8 vs. 9.3 cP) of the citrate/NaCl pH 6.0 sample (87.5 mg/mL) at a higher protein content suggesting an importance of charged amino acids over ionic excipients.

It is important to note that at a given concentration (i.e., 125 mg/mL), viscosity varies dramatically as a function of the formulation. Viscosity is ideally maintained below ~25 cP to ensure a realistically syringeable subcutaneous therapeutic product. In some embodiments of the OMS646 formulation, viscosity is maintained below about 20 cP to allow for delivery of the therapeutic product with an injection device, and also to allow for various types of bioprocessing, such as tangential flow filtration.

Second Viscosity Study

In an effort to reduce OMS646 formulation viscosity and, thus, maximize OMS646 concentration in a given formulation, an additional study was performed. Based on the initial results, the formulations most likely to produce a reduced viscosity formulation at high concentration were selected, namely: succinate/sorbitol pH 4.0 and glutamate- and arginine-containing citrate formulations at pH 6.0. Based on previous studies, charged amino acids were associated with several beneficial properties at neutral pH including increased buffer-exchange rate, increased sample processing recovery, and reduced viscosity. The impact of amino acids with a positively charged side chain (e.g., arginine) or amino acids with a negatively charged side chain (e.g., glutamate) were evaluated over a range of concentrations (50 mM to 150 mM) to gauge both excipient charge and concentration on viscosity. Finally, CaCl$_2$ was used as an additive in both isotonic and hypertonic citrate/glutamate solutions due to its potential viscosity reducing properties as described in U.S. Pat. No. 7,390,786.

Samples were buffer-exchanged and concentrated as described above. Following buffer-exchange, the protein content of all formulations was calculated. The exception was the formulation containing 50 mM glutamate and 50 mM CaCl$_2$, which precipitated following buffer-exchange and was not evaluated further. This is likely due in part to the limited solubility of citrate and divalent cations such as Ca'.

Figure 4:
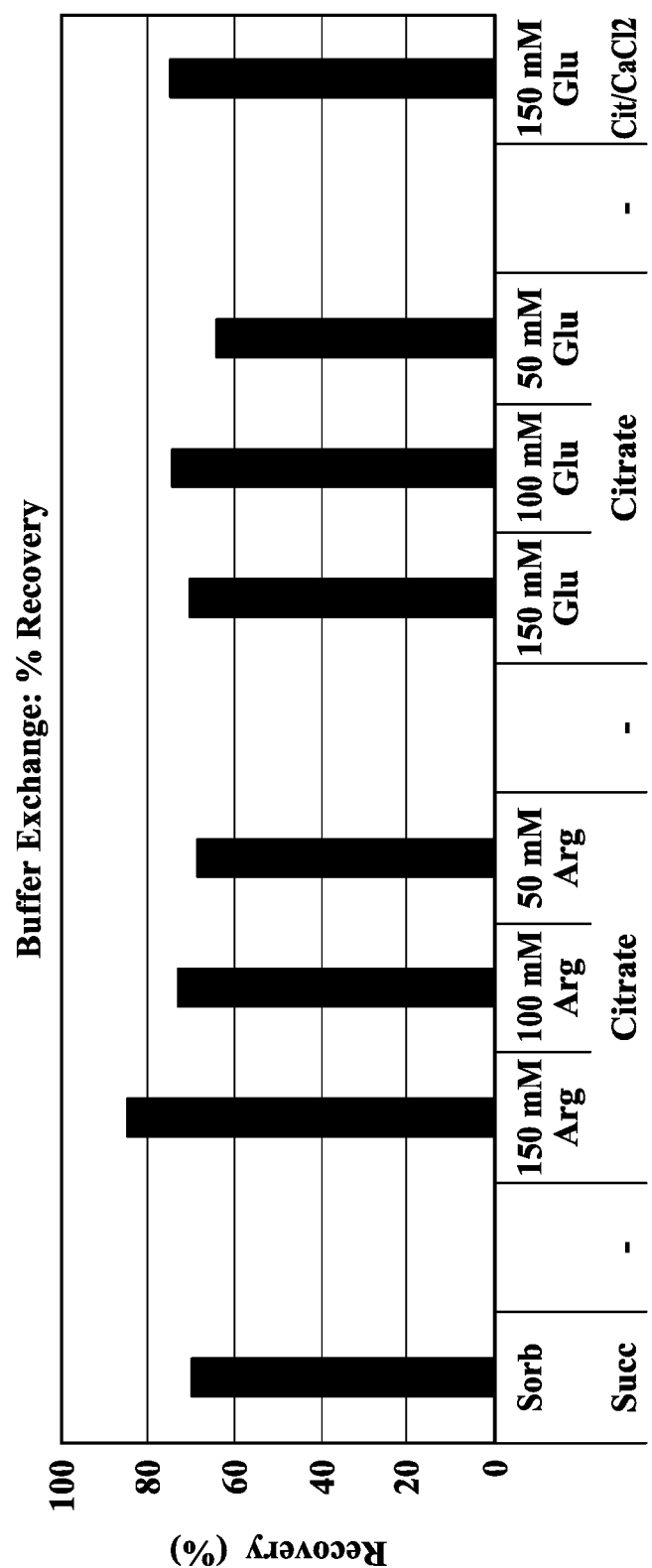
FIG. 4 graphically illustrates the percent protein recovery following buffer-exchange for the OMS646 solubility/viscosity study with various candidate formulations, as described in Example 2.
Figure 5:
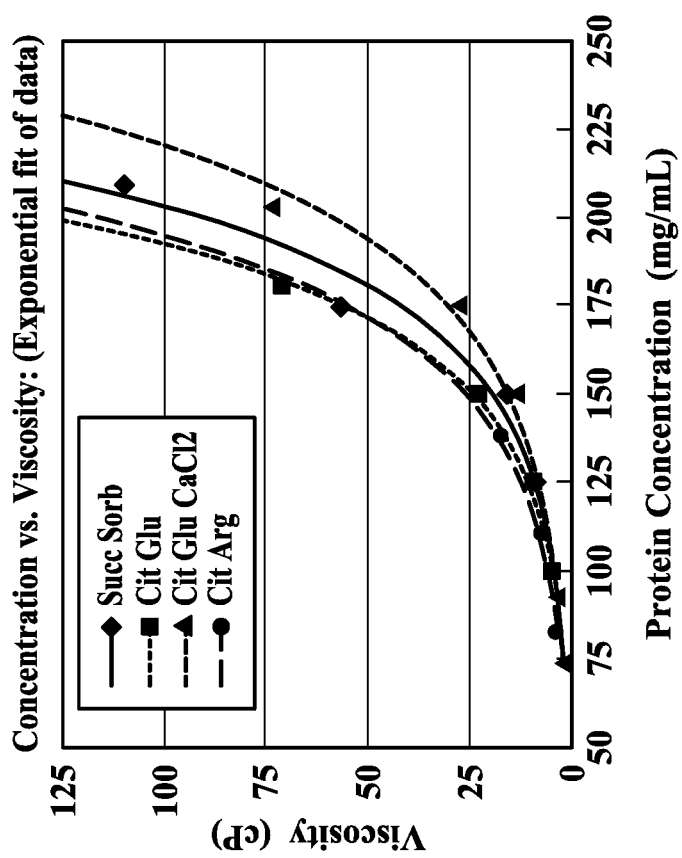
FIG. 5 graphically illustrates the viscosity (as determined by exponential fit of the viscosity data) versus protein concentration for the OMS646 solubility/viscosity study with various candidate formulations, as described in Example 2.

Results:

FIG. 4 graphically illustrates the percent protein recovery following buffer-exchange for the OMS646 solubility/viscosity study with various candidate formulations. As shown in FIG. 4, a trend towards increasing recovery with increasing arginine concentration was observed, where the 150 mM arginine formulation showed the highest protein recovery at 85%. Recoveries for the remaining formulations were comparable and ranged from 64-75%. Samples were then concentrated as described above until they became manually unworkable. All formulations were evaluated for viscosity as described above and the results are shown below in TABLE 3.

shown in FIG. 5, the 150 mM glutamate and arginine formulations showed almost identical curves that displayed the highest viscosity per unit concentration—a viscosity of 25 cP equating to ~150 mg/mL OMS646. The succinate sorbitol formulation performed somewhat better, with 25 cP corresponding to an estimated OMS646 content of ~160 mg/mL. The lowest overall viscosity was observed in the CaCl$_2$-containing formulation where the estimated content at 25 cP was ~175 mg/mL. The most intriguing result of this analysis was that the hypertonic formulation including 150 mM glutamate and 50 mM CaCl$_2$ dramatically reduced sample viscosity. Given the desire for the highest concentration liquid formulation possible, the application of divalent cations and hypertonicity towards viscosity reduction was carried forward into an additional viscosity study.

Third Viscosity Study

Based on the results from the initial viscosity studies described above, an additional study was carried out to determine whether the apparent viscosity reducing properties of CaCl$_2$ were related to the divalent Ca' or hypertonicity. A change in predominate excipient from glutamate to arginine was performed due to the improved buffer-exchange rates observed for arginine-containing formations. The incorporation of histidine was performed due to the

TABLE 3

Summary of the viscosity data from the pre-formulation studies

| Sample | Buffer | Excipient | Additive | pH | Conc (mg/mL) | Viscosity (cP) |
|---|---|---|---|---|---|---|
| | 100 cP Standard (97.2 cP Claim) | | | | — | 97.1 |
| | 50 cP Standard (49.2 Claim) | | | | — | 49.1 |
| S1 | 20 mM Succinate | 250 mM sorbitol | — | 4.0 | 209.3 | 109.6 |
| S2 | 20 mM Citrate | 150 mM Arginine | — | 6.0 | 181.2 | 70.5 |
| S3 | 20 mM Citrate | 100 mM Arginine | — | 6.0 | 170.8 | 102.8 |
| S4 | 20 mM Citrate | 50 mM Arginine | — | 6.0 | 158.3 | 140.1 |
| S5 | 20 mM Citrate | 150 mM Glutamate | — | 6.0 | 180.3 | 71.2 |
| S6 | 20 mM Citrate | 100 mM Glutamate | — | 6.0 | 170.7 | 74.6 |
| S7 | 20 mM Citrate | 50 mM Glutamate | — | 6.0 | 152.7 | 137.0 |
| S8 | 20 mM Citrate | 150 mM Glutamate | 50 mM CaCl$_2$ | 6.0 | 202.8 | 73.4 |

As shown above in TABLE 3, viscosities for all formulations were >70 cP, and despite the broad range of final concentrations, clear trends were observed. From this preliminary data, it was evident that increased arginine or glutamate concentration led to reduced viscosity. The viscosity of the succinate/sorbitol formulation appeared comparable to the 150 mM amino acid formulations. Inclusion of CaCl$_2$ showed a reduction in viscosity, where viscosity for this formulation was comparable to samples of 10% lower protein content.

Four formulations (S1, S2, S5 and S8 shown in TABLE 3) were selected for a more detailed viscosity analysis, where recovered neat samples were incrementally diluted in formulation buffer of 25 mg/mL. FIG. 5 graphically illustrates the viscosity (as determined by exponential fit of the viscosity data) versus protein concentration for the OMS646 solubility/viscosity study with various candidate formulations. The exponential fit of the viscosity data was determined in accordance with the methods described in Connolly B. et al., *Biophysical Journal* vol 103:69-78, 2012. As potential for chelation of Ca' by citrate which could lead to precipitation. A subset of samples also evaluated the impact of pH and surfactant on sample viscosity, as well as the impact of CaCl$_2$ and hypertonicity on the succinate/sorbitol pH 4.0 formulation. Samples were buffer-exchanged and concentrated as described for the previous viscosity studies. Viscosity for all formulations was measured using a rolling ball instrument as described above. Viscosity data was normalized to a sample protein concentration of 170 mg/mL. This was performed by first calculating a theoretical viscosity from the measured protein content using the exponential regression to previously calculated Viscosity/Solubility viscosity data from the citrate/arginine pH 6.0 formulation ($y=0.0917e^{0.0361x}$). The normalized viscosity was calculated by multiplying the theoretical viscosity for citrate/arginine pH 6.0 at 170 mg/mL (42.4 cP) by measured viscosity/theoretical viscosity (see Table 4, footnote b). The resulting normalized viscosities reveal much clearer trends by smoothing concentration-associated variability (see TABLE 4 and FIG. 6).

TABLE 4

Summary of Viscosity Data for OMS646 (170 mg/mL) formulations

| Form # | Buffer/pH | Excipient | Additive | PS-80 | Viscosity (cP) | Means Norm Conc (mg/mL) | Theor Viscosity (cP)[a] | Approx Norm Viscosity at 170 mg/mL (cP)[b] |
|---|---|---|---|---|---|---|---|---|
| | | 100 cP Standard (97.2 cP Claim) | | | 96.9 | | | — |
| 1A | 20 mM | 112.5 mM Arginine | 25 mM CaCl$_2$ | — | 38.8 | 165.5 | 36.0 | 45.7 |
| 1B | Citrate | 112.5 mM Arginine | 25 mM CaCl$_2$ | 0.05% | 41.7 | 168.5 | 40.2 | 44.0 |
| 2 | pH 6.0 | 150 mM Arginine | — | — | 20.8 | 155.7 | 25.3 | 34.9 |
| 3 | | 150 mM Arginine | 25 mM CaCl$_2$ | — | 20.1 | 157.0 | 26.5 | 32.2 |
| 4 | | 200 mM Arginine | — | — | 22.3 | 169.1 | 41.0 | 23.1 |
| 5 | | 225 mM Arginine | — | — | 20.2 | 169.0 | 40.9 | 20.9 |
| 6A | 20 mM | 112.5 mM Arginine | 25 mM CaCl$_2$ | — | 34.1 | 165.4 | 35.9 | 40.4 |
| 6B | Citrate | 112.5 mM Arginine | 25 mM CaCl$_2$ | 0.05% | 31.0 | 170.0 | 42.4 | 31.1 |
| 7 | pH 5.0 | 150 mM Arginine | — | — | 22.1 | 158.9 | 28.4 | 33.0 |
| 8 | | 150 mM Arginine | 25 mM CaCl$_2$ | — | 17.4 | 153.9 | 23.7 | 31.1 |
| 9 | 20 mM | 75 mM Arginine | 50 mM CaCl$_2$ | — | 19.9 | 174.5 | 49.9 | 16.9 |
| 10A | Histidine | 112.5 mM Arginine | 25 mM CaCl$_2$ | — | 27.9 | 169.6 | 41.8 | 28.4 |
| 10B | pH 6.0 | 112.5 mM Arginine | 25 mM CaCl$_2$ | 0.05% | 28.1 | 184.6 | 71.8 | 16.6 |
| 11 | | 135 mM Arginine | 10 mM CaCl$_2$ | — | 34.1 | 167.1 | 38.2 | 37.9 |
| 12 | | 150 mM Arginine | — | — | 35.5 | 156.6 | 26.1 | 57.7 |
| 13 | | 200 mM Arginine | — | — | 20.2 | 167.2 | 38.3 | 22.3 |
| 14 | | 225 mM Arginine | — | — | 16.4 | 161.9 | 31.6 | 22.0 |
| 15 | | 150 mM Arginine | 50 mM CaCl$_2$ | — | 15.9 | 164.9 | 35.2 | 19.1 |
| 16A | 20 mM | 125 mM Sorbitol | 50 mM CaCl$_2$ | — | 19.5 | 172.7 | 46.7 | 17.7 |
| 16B | Succinate | 125 mM Sorbitol | 50 mM CaCl$_2$ | 0.05% | 18.1 | 168.7 | 40.4 | 19.0 |
| 17 | pH 4.0 | 250 mM Sorbitol | 50 mM CaCl$_2$ | — | 15.5 | 157.2 | 26.8 | 24.6 |
| 18 | | 250 mM Sorbitol | | — | 16.8 | 161.3 | 31.0 | 23.0 |

[a] Theoretical viscosity was calculated using the regression to the measured content citrate/arginine pH 6.0 viscosity curve (y = 0.0917$e^{0.0361x}$)
[b] Theoretical viscosity of 170 mg/mL citrate/arginine pH 6.0 (42.4 cP)* (Measured Viscosity/Theor Viscosity)

Figure 6:
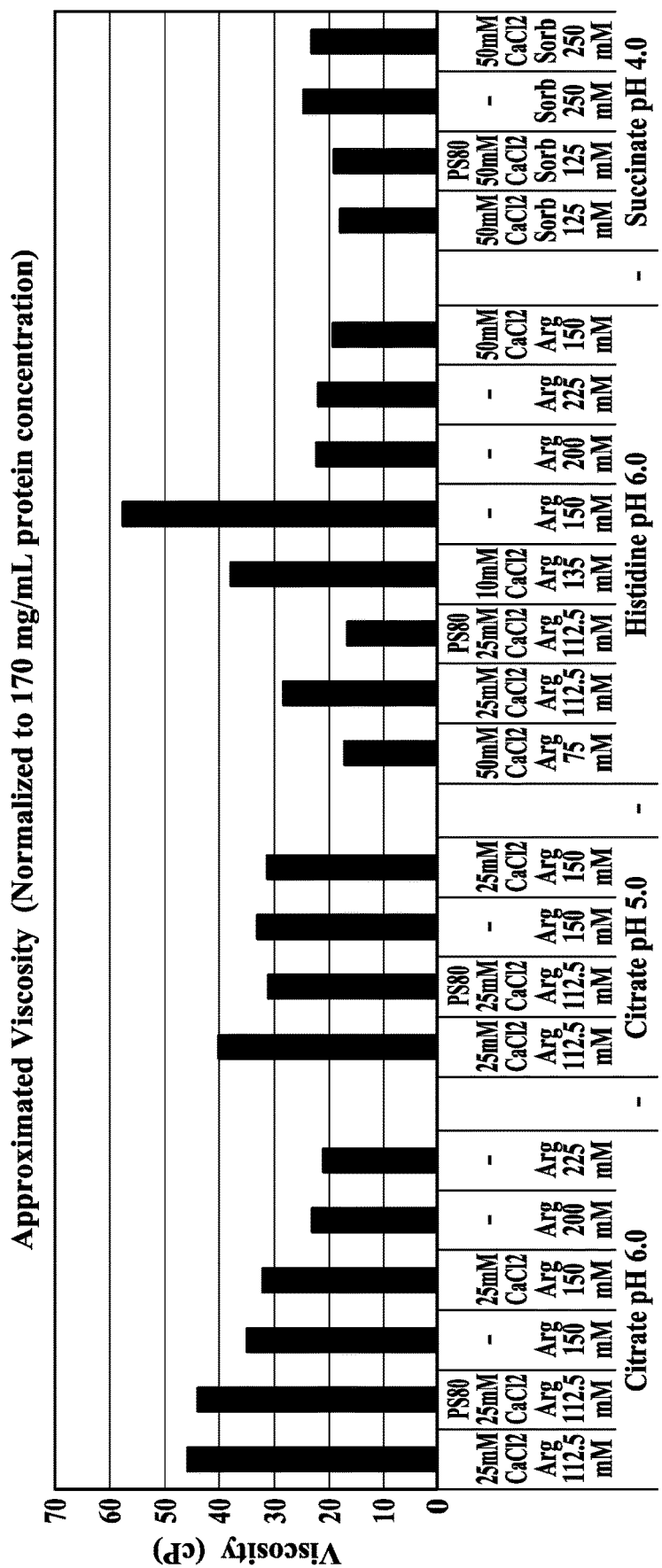
FIG. 6 graphically illustrates the protein concentration-normalized viscosity data for the viscosity study with various candidate OMS646 formulations, as described in Example 2.

FIG. 6 graphically illustrates the concentration-normalized viscosity data for the viscosity study with various candidate OMS646 formulations based on the data from TABLE 4. As shown in FIG. 6 and TABLE 4, for citrate and histidine formulations, examination of the normalized data set clearly shows that hypertonicity leads to reduced sample viscosity, wherein the majority of the impact is observed with only modest increases in arginine concentration. For example, the normalized viscosity of formulation 12 (20 mM histidine with 150 mM arginine) is 57.7 cP, compared with viscosities of 22.3 and 22.0 cP for histidine formulations containing 200 and 225 mM arginine, respectively. A similar trend was observed for citrate/arginine formulations. There was no obvious benefit of CaCl$_2$ inclusion. Rather, it was surprising to find that in the absence of CaCl$_2$, low viscosities (e.g., less than 25 cP) were achieved with the citrate/arginine and the histidine/arginine formulations with an arginine concentration of 200 mM or greater. Inclusion of 0.05% PS-80 resulted in substantial viscosity reduction in two of the three formulations evaluated at pH≥5.0. Finally, viscosities at pH 5.0 appeared somewhat lower than those for comparable formulations at pH 6.0.

In view of the results obtained from the viscosity studies, hypertonic arginine, the presence or absence of divalent cations and the succinate/sorbitol pH 4.0 formulations were carried forward into surfactant screening studies to further evaluate the impact on OMS646 physical, conformation, and chemical stability.

4. Surfactant Screening

The impact of surfactant on OMS646 stability was evaluated using candidate formulations identified in prior studies described herein. For surfactant screening studies, six formulations were analyzed as follows:

20 mM citrate, 200 mM arginine at pH 5.0

20 mM citrate, 200 mM arginine at pH 6.0;

20 mM succinate, 250 mM sorbitol at pH 4.0;

20 mM histidine, 200 mM arginine at pH 6.0;

20 mM histidine, 75 mM arginine/50 mM CaCl$_2$ at pH 6.0;

20 mM histidine, 75 mM arginine/50 mM MgCl$_2$ at pH 6.0

Each of the six formulations shown above was evaluated either without surfactant or in the presence of 0.01% PS-80 for a total of twelve unique formulation conditions. For each formulation, OMS646 was exchanged into buffer-exchange solutions (no PS-80), concentrated, the content was measured and the samples were normalized to 175 mg/mL protein. Each formulation was then split and PS-80 was added into the appropriate samples to a final concentration of 0.01% (w/v).

The formulated samples were each subjected to mechanical stress by agitation, and freeze/thaw cycling. For both types of stress, 0.5 mL of sample was transferred into four type 1 borosilicate glass vials (2.0 mL) and sealed using FluroTec® stoppers. For agitation stress, the samples were placed in a microplate shaker at 600 rpm for ~60 hours at room temperature. Agitation control samples were kept next to the shaker for the duration of the agitation stress. For freeze/thaw cycling, the samples were frozen at −80° C. for ≥60 minutes and then allowed to thaw at room temperature, for a total of 5 freeze-thaw cycles. Following stressing, samples were stored at 2-8° C. until analysis. The remaining sample was maintained at 2-8° C. as an unstressed control. Appearance, A280 measurements, DLS and SEC were performed to evaluate the impact of surfactant on OMS646 aggregation and stability.

Results:

Following stressing of the six OMS646 formulations, no sample showed evidence of product-related particulate matter. Protein content was essentially constant for all samples of a given formulation. Analysis of DLS data for freeze/thaw and agitation samples revealed only subtle differences between formulations and stress-types, with no clear global trends observed with regard to PS-80 inclusion. The one exception was the succinate/sorbitol pH 4.0 formulation in which inclusion of PS-80 led to high overall polydispersity (i.e., multimodal) for freeze/thaw and 5° C. control samples. This acidic formulation also showed evidence of aggregation/self-association by DLS in the absence of PS-80 upon agitation.

Analysis of SEC data was performed to evaluate any aggregation and/or degradation products arising during sample stressing. The results are summarized in TABLES 5A-5D.

TABLE 5A

Summary of SEC data for OMS646 formulation surfactant screening (2-8° C.)

| Form. | Buffer | Excipient | Additive | pH | PS-80 (%) | Ave Total HMW (%) | Ave Monomer (%) | Ave Total LMW (%) |
|---|---|---|---|---|---|---|---|---|
| | Average Unprocessed Reference Sample | | | | | 3.7 | 96.3 | — |
| 1 | 20 mM citrate | 200 mM Arginine | — | 5.0 | — | 3.0 | 96.3 | — |
| 2 | | | | | 0.01 | 3.1 | 96.9 | — |
| 3 | 20 mM citrate | 200 mM Arginine | — | 6.0 | — | 3.2 | 96.8 | — |
| 4 | | | | | 0.01 | 3.3 | 96.7 | — |
| 5 | 20 mM histidine | 200 mM Arginine | — | 6.0 | — | 3.3 | 96.7 | — |
| 6 | | | | | 0.01 | 3.4 | 96.6 | — |
| 7 | 20 mM Succinate | 250 mM Sorbitol | — | 4.0 | — | 3.2 | 96.6 | 0.2 |
| 8 | | | | | 0.01 | 3.2 | 96.5 | 0.2 |
| 9 | 20 mM histidine | 75 mM Arginine | 50 mM CaCl$_2$ | 6.0 | — | 3.3 | 96.7 | — |
| 10 | | | | | 0.01 | 3.4 | 96.6 | — |
| 11 | 20 mM histidine | 75 mM Arginine | 50 mM MgCl$_2$ | 6.0 | — | 3.4 | 96.6 | — |
| 12 | | | | | 0.01 | 3.5 | 96.5 | — |

TABLE 5B

Summary of SEC data for OMS646 formulation surfactant screening (Freeze/Thaw)

| Form. | Buffer | Excipient | Additive | pH | PS-80 (%) | Ave Total HMW (%) | Ave Monomer (%) | Ave Total LMW (%) |
|---|---|---|---|---|---|---|---|---|
| | Average Unprocessed Reference Sample | | | | | 3.7 | 96.3 | — |
| 1 | 20 mM citrate | 200 mM Arginine | — | 5.0 | — | 3.1 | 96.9 | — |
| 2 | | | | | 0.01 | 3.2 | 96.8 | — |
| 3 | 20 mM citrate | 200 mM Arginine | — | 6.0 | — | 3.3 | 96.7 | — |
| 4 | | | | | 0.01 | 3.3 | 96.7 | — |
| 5 | 20 mM histidine | 200 mM Arginine | — | 6.0 | — | 3.3 | 96.7 | — |
| 6 | | | | | 0.01 | 3.4 | 96.6 | — |
| 7 | 20 mM Succinate | 250 mM Sorbitol | — | 4.0 | — | 3.2 | 96.6 | 0.2 |
| 8 | | | | | 0.01 | 3.2 | 96.6 | 0.2 |
| 9 | 20 mM histidine | 75 mM Arginine | 50 mM CaCl$_2$ | 6.0 | — | 3.4 | 96.6 | — |
| 10 | | | | | 0.01 | 3.4 | 96.6 | — |
| 11 | 20 mM histidine | 75 mM Arginine | 50 mM MgCl$_2$ | 6.0 | — | 3.5 | 96.6 | — |
| 12 | | | | | 0.01 | 3.5 | 96.6 | — |

TABLE 5C

Summary of SEC data for OMS646 formulation surfactant screening (25° C.)

| Form. | Buffer | Excipient | Additive | pH | PS-80 (%) | Ave Total HMW (%) | Ave Monomer (%) | Ave Total LMW (%) |
|---|---|---|---|---|---|---|---|---|
| | Average Unprocessed Reference Sample | | | | | 3.7 | 96.3 | — |
| 1 | 20 mM citrate | 200 mM Arginine | — | 5.0 | — | 3.1 | 96.9 | — |
| 2 | | | | | 0.01 | 3.2 | 96.8 | — |
| 3 | 20 mM citrate | 200 mM Arginine | — | 6.0 | — | 3.3 | 96.7 | — |
| 4 | | | | | 0.01 | 3.4 | 96.6 | — |
| 5 | 20 mM histidine | 200 mM Arginine | — | 6.0 | — | 3.3 | 96.7 | — |
| 6 | | | | | 0.01 | 3.4 | 96.6 | — |
| 7 | 20 mM Succinate | 250 mM Sorbitol | — | 4.0 | — | 3.3 | 96.5 | 0.2 |
| 8 | | | | | 0.01 | 3.3 | 96.5 | 0.2 |
| 9 | 20 mM histidine | 75 mM Arginine | 50 mM CaCl$_2$ | 6.0 | — | 3.4 | 96.6 | — |
| 10 | | | | | 0.01 | 3.5 | 96.5 | — |
| 11 | 20 mM histidine | 75 mM Arginine | 50 mM MgCl$_2$ | 6.0 | — | 3.5 | 96.5 | — |
| 12 | | | | | 0.01 | 3.5 | 96.5 | — |

TABLE 5D

Summary of SEC data for OMS646 formulation surfactant screening (Agitation)

| Form. | Buffer | Excipient | Additive | pH | PS-80 (%) | Ave Total HMW (%) | Ave Monomer (%) | Ave Total LMW (%) |
|---|---|---|---|---|---|---|---|---|
| | Average Unprocessed Reference Sample | | | | | 3.7 | 96.3 | — |
| 1 | 20 mM citrate | 200 mM Arginine | — | 5.0 | — | 3.0 | 97.0 | — |
| 2 | 20 mM citrate | 200 mM Arginine | — | | 0.01 | 3.2 | 96.8 | — |
| 3 | 20 mM citrate | 200 mM Arginine | — | 6.0 | — | 3.3 | 96.7 | — |
| 4 | 20 mM citrate | 200 mM Arginine | — | | 0.01 | 3.4 | 96.6 | — |
| 5 | 20 mM histidine | 200 mM Arginine | — | 6.0 | — | 3.3 | 96.7 | — |
| 6 | 20 mM histidine | 200 mM Arginine | — | | 0.01 | 3.4 | 96.6 | — |
| 7 | 20 mM Succinate | 250 mM Sorbitol | — | 4.0 | — | 2.8 | 97.0 | 0.2 |
| 8 | 20 mM Succinate | 250 mM Sorbitol | — | | 0.01 | 3.3 | 96.5 | 0.2 |
| 9 | 20 mM histidine | 75 mM Arginine | 50 mM CaCl$_2$ | 6.0 | — | 3.4 | 96.3 | 0.3 |
| 10 | 20 mM histidine | 75 mM Arginine | 50 mM CaCl$_2$ | | 0.01 | 3.5 | 96.5 | — |
| 11 | 20 mM histidine | 75 mM Arginine | 50 mM MgCl$_2$ | 6.0 | — | 3.4 | 96.6 | — |
| 12 | 20 mM histidine | 75 mM Arginine | 50 mM MgCl$_2$ | | 0.01 | 3.6 | 96.5 | — |

As shown above in TABLES 5A-5D, overall, the SEC data indicate that the OMS646 molecule is generally insensitive to inclusion of PS-80 and both freeze/thaw (TABLE 5B) and agitation stress (TABLE 5D), regardless of surfactant. It was observed that the worst performing OMS646 formulations were those containing divalent cation additives (CaCl$_2$ and MgCl$_2$) where high molecular weight (HMW) material for these samples was clearly elevated relative to other samples and the lowest levels of monomer were observed.

5. Stability Analysis Under Stressed and Unstressed Conditions for 28 Days

After narrowing the potential buffer, excipient, and surfactant combinations through the pre-formulation studies described above, citrate and histidine buffers were formulated using 200 mM arginine over the pH range 5.5-6.5 at high concentrations of 175 mg/mL and 200 mg/mL OMS646 to identify the most suitable formulation under both stressed (40° C.) and unstressed (5° C.) conditions. Arginine was included at a hypertonic level (200 mM) due to the viscosity-reducing properties at this elevated concentration. Based on statistical numerical optimization of the pre-formulation data, the most suitable OMS646 formulation was determined to be 20 mM citrate and 200 mM arginine. A panel of samples was also prepared to evaluate the impact of 0.01% PS-80 on citrate and histidine formulations.

Buffer-exchange was carried out as described above, samples were concentrated and diluted to achieve the target concentrations of 175 or 200 mg/mL OMS646. During this final normalization, PS-80 was added to 0.01% for the appropriate formulations. The formulations were sterile filtered using Millipore Ultrafree-CL GV 0.22 µM sterile concentrators. One vial of each formulation was placed at 5° C. and one at 40° C. for a 28 day incubation period. The samples were analyzed at To and 28 days with regard to concentration, appearance, turbidity, osmolality, pH, DLS, DSC and viscosity. Following the 28 day incubation, it was observed that both the 175 and 200 mg/mL OMS646 succinate/sorbitol formulation stored at 40° C. developed a gel-like consistency, and thus were not analyzed.

Results:

With regard to the stability analysis, pH values remained stable over the duration of the study, regardless of formulation and storage condition. After 28 days, both SEC and SDS-CE analysis indicated substantial increases in LMW content for the acidic pH 5.0 and pH 4.0 formulations, eliminating these formulations from further consideration. For the pH 6.0 citrate/arginine and histidine/arginine formulated with 0.01% PS-80, most responses were nearly indistinguishable from associated surfactant-free samples. SEC, however, showed reductions in HMW content of 0.2%-0.6% relative to surfactant-free counterpart formulations. Coupled with the apparent viscosity-reducing properties of the surfactant, polysorbate-80 (PS-80) was chosen to be included in further formulation studies.

The concentration and viscosities of a total of 10 formulations were tested after 28 days at 5° C. Representative results are shown in TABLE 6.

TABLE 6

Viscosity of Formulations after 28 days at 5° C.

| Sample | Formulation | Concentration 28 days at 5° C. (mg/mL) | Viscosity (cP) |
|---|---|---|---|
| 1 | 20 mM Citrate, 200 mM Arginine, pH 6.0, 175 mg/mL OMS646 | 153.4 | 10.6 |
| 2 | 20 mM Histidine, 200 mM Arginine, pH 6.0, 175 mg/mL OMS646 | 151.3 | 12.7 |
| 3 | 20 mM Citrate, 200 mM Arginine, pH 6.0, 200 mg/mL OMS646 | 170.5 | 27.4 |
| 4 | 20 mM Histidine, 200 mM Arginine, pH 6.0, 200 mg/mL OMS646 | 184.2 | 18.1 |
| 5 | 20 mM Citrate, 200 mM Arginine, 0.01% PS-80, pH 6.0, 175 mg/mL OMS646 | 159.2 | 9.0 |
| 6 | 20 mM Histidine, 200 mM Arginine, 0.01% PS-80, pH 6.0, 175 mg/mL OMS646 | 156.0 | 7.8 |
| 7 | 20 mM Citrate, 200 mM Arginine, pH 5.0, 175 mg/mL OMS646 | 143.2 | 9.8 |
| 8 | 20 mM Histidine, 200 mM Arginine, pH 5.0, 200 mg/mL OMS646 | 182.4 | 15.9 |
| 9 | 20 mM Succinate, 250 mM Sorbitol, pH 4.0, 175 mg/mL OMS646 | 150.6 | 14.5 |
| 10 | 20 mM Succinate, 250 mM Sorbitol, pH 4.0, 200 mg/mL | 184.3 | 18.0 |

As shown above in TABLE 6, higher concentration formulations displayed higher viscosities. Of considerable interest was the observation that inclusion of PS-80 led to reduction in viscosity for both citrate (10.6 vs 9.0 cP) and histidine (12.7 vs. 7.8 cP) formulations, while also preserving protein recovery. Such reductions in viscosity upon inclusion of PS-80 are beneficial, allowing for a higher concentration of OMS646 while maintaining a low viscosity that is considered to be syringeable in a clinical setting and also suitable for use in an autoinjector and other injection devices.

Summary of the Results

The primary aim of these studies was to identify formulation components that would result in optimal chemical, physical, and structural stability of high concentration OMS646 antibody in liquid formulations. In addition, several viscosity-specific studies were carried with the goal of obtaining a final formulation with maximal OMS646 antibody concentration that could be feasibly delivered by subcutaneous administration.

Several buffer types, pH conditions, excipients, and surfactant concentrations were evaluated in an iterative fashion over the course of the studies directed at evaluation of buffer systems, excipients, solubility, viscosity, and surfactant screening studies. The initial Baseline Buffer Evaluation Study tested five different buffer types (acetate, citrate, succinate, histidine, and phosphate) over the pH range 4.0-8.0. Analysis by DSC, DLS, and the AVIA chemical denaturation system indicated that more acidic and basic conditions were least suitable for OMS646 antibody stability. Based on the results, acetate, citrate, and histidine buffer systems were selected for further evaluation.

Excipient screening evaluated the effect of NaCl, L-arginine, L-glutamate, L-proline, sucrose, and sorbitol on OMS646 antibody stability in each of the three chosen buffer systems. Citrate (pH 6.0) was carried forward alone into further studies to maximize design space for additional excipient evaluation. Only sucrose was eliminated as a potential excipient due to poor light scattering data. Solubility screening evaluated the ability of citrate (pH 5.0 and pH 6.0) formulations containing isotonic combinations of NaCl, sorbitol, arginine, glutamate, and proline to support high solution concentrations of OMS646 antibody. All formulations were concentrated in excess of 150 mg/mL OMS646 without evidence of aggregation. Succinate/arginine and succinate/glutamate formulations, however, showed evidence of precipitation/aggregation following short-term storage and were not evaluated further. Biophysical analysis of the citrate formulations showed only minor differences between excipients at pH 6.0 and only a modest reduction of HMW content in counterpart pH 5.0 formulations.

Interesting data came from viscosity measurements of this subset of samples, which suggested that citrate/glutamate and succinate/sorbitol imparted the lowest viscosities. Given the similar biophysical stabilities observed between excipients and the importance of obtaining a formulation with maximum OMS646 content, additional viscosity studies were performed. These viscosity studies identified divalent cations and/or modest hypertonicity as a significant factor in reducing OMS646 antibody formulation viscosity at more neutral pH. Both citrate (pH 5.0 and 6.0) and histidine (pH 6.0) were evaluated in the presence of 200 mM arginine. Histidine pH 6.0 was also evaluated in the presence of 75 mM arginine and either 50 mM $CaCl_2$ or 50 mM $MgCl_2$. Finally, succinate/sorbitol pH 4.0 was tested. All buffer/excipient combinations were tested either in the absence or presence of 0.01% PS-80 to determine if surfactant promoted OMS646 antibody stability under agitation and freeze/thaw stress conditions. All formulations appeared stable against the environmental stresses applied, regardless of surfactant. One striking observation was the increase in OMS646 HMW content observed by SEC for formulations containing divalent cations. Therefore, $CaCl_2$ and $MgCl_2$ were eliminated form further consideration as excipients. Succinate/sorbitol also showed reduced OMS646 antibody purity, which was mainly attributable to an apparent increase in LMW impurities. While the differences between formulation containing and lacking 0.01% PS-80 were minor, samples containing surfactant did appear to show modestly increased HMW content (~0.1%) relative to their surfactant-free counterparts.

Example 3

This Example describes a study in which three candidate highly concentrated, low viscosity OMS646 formulations, identified based on the pre-formulation studies described in Example 2, were compared with respect to syringeability.

Background/Rationale:

The time and force required for a manual injection (or time required for an injection using an auto-injector) are important and may impact the ease of use of the product by the end-user and thus compliance. The force required for the injection of a solution at a given injection rate via a needle of predetermined gauge and length is referred to as 'syringeability' (see e.g., Burckbuchler, V.; et al., *Eur. J. Pharm. Biopharm.* 76 (3), 351-356, 2010). With regard to syringeability for administration to a human subject, one generally does not want to exceed a 25N force (although there are marketed formulations more viscous than this). A 27GA needle or a 27GA thin wall needle are generally considered standard needles for subcutaneous injection of monoclonal antibodies. The 27GA thin wall needle has an ID roughly equal to a 25GA needle (smaller G numbers are bigger diameters).

The following study was carried out to determine the syringeability of three candidate highly concentration low viscosity OMS646 formulations.

Methods:

Based on the pre-formulation studies described in Example 2, the following three candidate high concentration OMS646 formulations were selected and further studied, as shown in TABLE 7. In this example, the formulations were prepared using arginine hydrochloride, polysorbate 80 if indicated, and either trisodium citrate or histidine, with the pH being adjusted to about 5.8 to 6.0 using hydrochloric acid.

TABLE 7

Candidate high concentration OMS646 formulations

| Formulation | Buffer/Excipients/Surfactant/pH | Concentration of OMS646 | Protein content |
|---|---|---|---|
| 1 | 20 mM Citrate, 200 mM Arginine, 0.01% PS-80, pH 5.8 | 185 mg/mL | 187.1 |
| 2 | 20 mM Histidine, 200 mM Arginine, 0.01% PS-80, pH 5.9 | 185 mg/mL | 188.2 |
| 3 | 20 mM Citrate, 200 mM Arginine, pH 5.8 | 185 mg/mL | 193.3 |

1. Osmolality and Viscosity of OMS646 Candidate Formulations

Osmolality and viscosity of the three candidate formulations generated as shown in TABLE 7 were determined using methods described in Example 2. Fluid behavior of the formulation was considered to be non-Newtonian if the % RSD>10 over shear rates tested. The results are shown in TABLE 8.

TABLE 8

Osmolality and Viscosity

| Formulation | Buffer/Excipients/Surfactant/pH | Conc. | Osmolality (mOsm/kg) | Viscosity (cP) | Fluid Behavior |
|---|---|---|---|---|---|
| 1 | 20 mM Citrate, 200 mM Arginine, 0.01% PS-80, pH 5.8 | 185 mg/mL | 473 | 16.1 | Newtonian |
| 2 | 20 mM Histidine, 200 mM Arginine, 0.01% PS-80, pH 5.9 | 185 mg/mL | 440 | 15.9 | Newtonian |
| 3 | 20 mM Citrate, 200 mM Arginine, pH 5.8 | 185 mg/mL | 468 | 21.3 | Newtonian |

2. Syringeability of OMS646 Candidate Formulations

Methods:

Syringeability analysis of the three OMS646 formulations was carried out with respect to average load and max load using 27 GA (1.25"), 25GA (1") and 25GA thin-walled (1") needles. Triplicate replicates of each formulation were each injected once. Results for the syringeability samples are averages of the triple replicates.

Figure 7A:
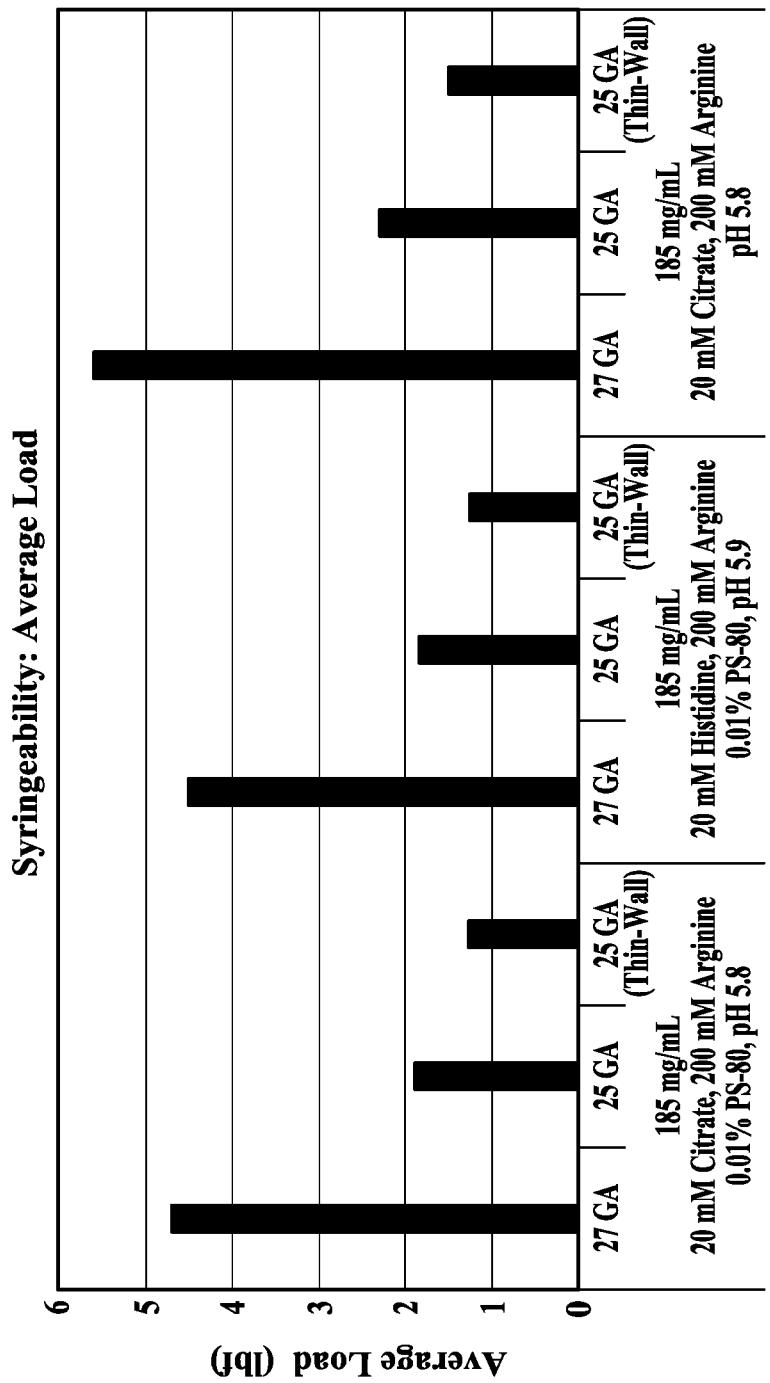
FIG. 7A graphically illustrates the average load (lbf) of three candidate OMS646 formulations in a syringeability study using 27 GA (1.25"), 25GA (1") and 25GA thin-walled (1") needles as described in Example 3.
Figure 7B:
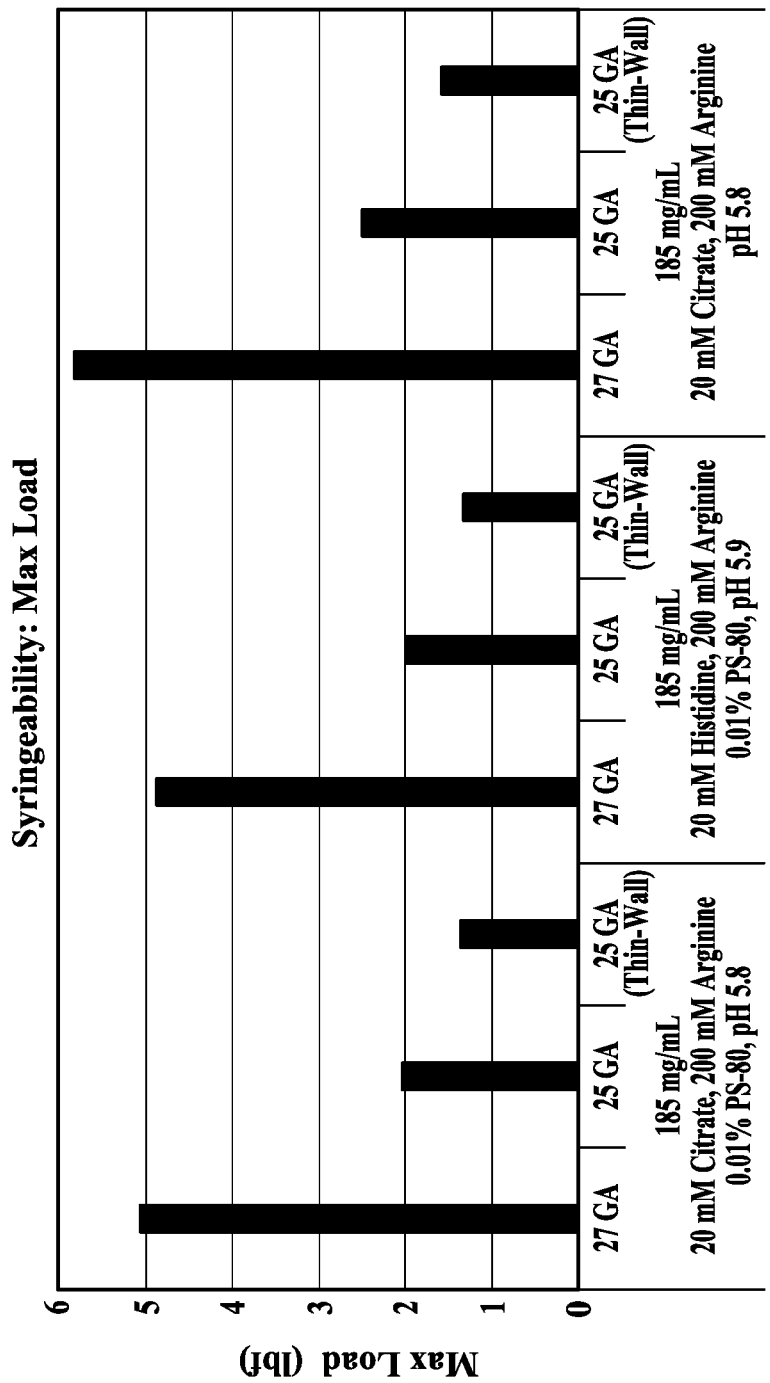
FIG. 7B graphically illustrates the maximum load (lbf) of three candidate OMS646 formulations in a syringeability study using 27 GA (1.25"), 25GA (1") and 25GA thin-walled (1") needles as described in Example 3.

Results:

The three formulations shown in TABLE 7 (containing OMS646 at 185 mg/mL) were evaluated for their syringeability using 27GA (1.25"), 25GA thin-walled (1"), and 25GA (1") needles. Reported results are the average of triplicate replicates. The results are shown in TABLE 9 and are graphically illustrated in FIGS. 7A and 7B. FIG. 7A graphically illustrates the average load (lbf) of three candidate OMS646 formulations using 27GA, 25GA and 25GA thin-walled needles. FIG. 7B graphically illustrates the maximum load (lbf) of three candidate OMS646 formulations using 27GA, 25GA and 25GA thin-walled needles.

TABLE 9

Syringeability of the candidate high-concentration OMS646 formulations

| Formulation | Condition | Average Load (lbf) | Max Load (lbf) | Average Load (N) | Max Load (N) |
|---|---|---|---|---|---|
| 1 | 27 GA | 4.72 | 5.07 | 20.99 | 22.55 |
|   | 25 GA | 1.88 | 2.03 | 8.36 | 9.03 |
|   | 25 GA (thin-wall) | 1.27 | 1.36 | 5.65 | 6.05 |
| 2 | 27 GA | 4.51 | 4.85 | 20.06 | 21.57 |
|   | 25 GA | 1.84 | 1.99 | 8.18 | 8.85 |
|   | 25 GA (thin-wall) | 1.26 | 1.32 | 5.60 | 5.80 |
| 3 | 27 GA | 5.58 | 5.83 | 24.82 | 25.93 |
|   | 25 GA | 2.29 | 2.51 | 10.18 | 11.16 |
|   | 25 GA (thin-wall) | 1.50 | 1.60 | 6.67 | 7.11 |

As described above, with regard to syringeability for administration to a human subject, one generally does not want to exceed a 25N force. As shown above in TABLE 9, all three candidate high concentration OMS646 formulations have acceptable syringeability (i.e., a force not exceeding 25N) when injected through a 25GA or 25GA thin-walled syringe. Formulation #2 also has acceptable syringeability when injected through a 27 G needle. The addition of PS-80 0.01% caused an unexpected improvement in syringeability.

3. SEC Analysis of OMS646 Candidate Formulations Post-Injection

Size exclusion chromatography (SEC) was used to evaluate the quantity of aggregates and degradation products present in the three OMS646 candidate formulations post-injection. Briefly, an Agilent 1100 HPLC system was fitted with a G3000SWx1 SEC column (Tosoh, 7.8×300 mm, 5 µm particle size). OMS646 samples were diluted to 2.5 mg/mL in SEC mobile phase (140 mM potassium phosphate, 75 mM potassium chloride, pH 7.0) and 20 µL of sample was injected into the HPLC column. The system was run using a flow rate of 0.4 mL/min, and eluted protein was detected by absorption at 280 nm (bandwidth 4 nm) with no reference correction. To assess system suitability, all samples were bracketed by mobile phase blank and gel filtration standard injections, and reference material was injected in duplicate at the beginning of the sequence. Percent abundances for individual and total high molecular weight (HMW) species and low molecular weight (LMW) species, in addition to percent monomer and total integrated peak area were reported.

Results:

The results of the SEC analysis of the high concentration OMS646 candidate formulations post-injection are shown in TABLE 10.

TABLE 10

SEC Analysis of the high-concentration OMS646 formulations post-injection

| Formulation | Condition | % Purity | % HMW | % LMW |
|---|---|---|---|---|
| 1 | Control | 96.5 | 3.3 | 0.1 |
|   | 27 GA | 96.4 | 3.5 | 0.2 |
|   | 25 GA | 96.4 | 3.4 | 0.2 |
|   | 25 GA (thin-wall) | 96.4 | 3.4 | 0.2 |
| 2 | Control | 96.6 | 3.4 | Not detected |
|   | 27 GA | 96.5 | 3.5 | Not detected |
|   | 25 GA | 96.5 | 3.5 | Not detected |
|   | 25 GA (thin-wall) | 96.5 | 3.5 | Not detected |
| 3 | Control | 96.5 | 3.4 | 0.2 |
|   | 27 GA | 96.3 | 3.5 | 0.2 |
|   | 25 GA | 96.4 | 3.5 | 0.2 |
|   | 25 GA (thin-wall) | 96.3 | 3.5 | 0.2 |

These results show little or no change in purity by SEC following expulsion through the needle.

Summary of Results:

The results of the syringeability analysis demonstrate that all three candidate high concentration OMS646 formulations have acceptable syringeability when tested using needles suitable for subcutaneous administration and there is little or no change in purity of the OMS646 following expulsion through the needle. The addition of PS-80 0.01% provided an unexpected improvement in the syringeability of the citrate arginine-containing formulation.

Example 4

This Example describes a study that was carried out to evaluate the stability of candidate high-concentration low viscosity OMS646 antibody formulations during long-term storage.

Methods:
This study was carried out to evaluate the stability of high-concentration OMS646 antibody formulations for subcutaneous injection after long-term storage.

points and conditions, and the samples were characterized by the following methods: Appearance by Visual Inspection, Protein Content by A280, Osmolality, SEC-HPLC, pH, and MASP-2 ELISA. The exemplary SEC-HPLC data is summarized in TABLE 11 and shows that the OMS646 antibody maintained its integrity after storage at 5° C. for 6, 9 and 12 months. The ELISA data confirmed that the antibody preserved its functionality after storage at 5° C. for 6, 9 and 12 months.

Results:

The results of this study are summarized in TABLE 11 below.

TABLE 11

Stability of Formulations as analyzed by SEC

| Formulation | Time Point | Condition | Total HMW (oligomer) (%) | Main Peak (monomer) (%) | Total LMW (%) |
|---|---|---|---|---|---|
| 185 mg/mL OMS646 | T0 | NA | 3.9 | 96.1 | — |
| 20 mM Citrate | 1 month | −20° C. | 2.5 | 97.5 | — |
| 200 mM Arginine | | 5° C. | 2.6 | 97.4 | — |
| 0.01% Polysorbate 80 | | 25° C./60% RH | 2.7 | 97.3 | — |
| pH 5.8 | 2 months | −20° C. | 2.9 | 97.1 | — |
| | | 5° C. | 3.1 | 96.9 | — |
| | | 25° C./60% RH | 3.4 | 96.6 | — |
| | 3 months | −20° C. | 2.8 | 97.2 | — |
| | | 5° C. | 2.9 | 97.1 | — |
| | | 25° C./60% RH | 3.3 | 96.0 | 0.7 |
| | 6 months | −20° C. | 1.7 | 98.3 | — |
| | | 5° C. | 1.9 | 98.1 | — |
| | | 25° C./60% RH | 2.0 | 98.0 | — |
| | 9 months | 5° C. | 3.4 | 96.6 | — |
| | | 25° C./60% RH | 4.0 | 95.7 | 0.2 |
| | 12 months | 5° C. | 3.4 | 96.6 | — |
| 185 mg/mL OMS646 | T0 | NA | 3.8 | 96.2 | — |
| 20 mM Histidine | 1 month | −20° C. | 2.7 | 97.3 | — |
| 200 mM Arginine | | 5° C. | 2.7 | 97.3 | — |
| 0.01% Polysorbate 80 | | 25° C./60% RH | 2.9 | 97.1 | — |
| pH 5.9 | 2 months | −20° C. | 2.9 | 97.1 | — |
| | | 5° C. | 3.3 | 96.7 | — |
| | | 25° C./60% RH | 3.3 | 96.7 | — |
| | 3 months | −20° C. | 2.8 | 97.1 | 0.1 |
| | | 5° C. | 3.0 | 96.9 | 0.1 |
| | | 25° C./60% RH | 3.1 | 96.1 | 0.8 |
| | 6 months | −20° C. | 1.8 | 98.2 | — |
| | | 5° C. | 1.9 | 98.1 | — |
| | | 25° C./60% RH | 2.0 | 98.0 | — |

Two candidate formulations were evaluated as follows:
A) 20 mM citrate, 200 mM arginine, 0.01% PS-80, pH 5.8 (185 mg/mL OMS646)
B) 20 mM histidine, 200 mM arginine, 0.01% PS-80, pH 5.9 (185 mg/mL OMS646)

Samples were filled into 13 mm, 2 mL size USP Type I Schott Glass Tubing Vials (West Pharmaceuticals), with a 1.0 mL sample fill, sealed with 13 mm Fluorotec stoppers (West Pharmaceuticals), and capped with 13FO aluminum caps with buttons (West Pharmaceuticals or equivalent). The sample vials were stored in controlled temperature reach-in stability chambers at −75±10° C., −20±5° C., 5±3° C., 25±2° C./60±5% RH, and 40±2° C./75±5% RH. A target of at least 40 sample vials per formulation were stored for the present study. Samples stored as liquid were stored in an inverted orientation, while frozen samples were stored upright. The required number of vials was pulled at the associated time As shown in TABLE 11, little or no change in purity was observed in the samples stored up to 9 months at −20° C. or stored at 5° C. up to 12 months, the intended storage temperature. The purity of the samples stored at 25° C. was also maintained over 2 months, however, slight changes in purity at 25° C. were observed over 9 months of storage.

Example 5

An exemplary formulation containing the MASP-2 inhibitory antibody OMS646 at pH 5.8 was prepared by combining OMS646 (185 mg/mL) with citrate (20 mM), arginine (200 mM) and polysorbate 80 (0.01%). Sodium citrate dihydrate (4.89 mg/mL) and citric acid monohydrate (0.71 mg/mL) were used to prepare the citrate buffer, with hydrochloric acid and/or sodium hydroxide used to adjust the pH as needed.

The viscosity of this formulation was measured with a capillary viscometer, and the results are shown in TABLE 12. There is a slight decrease in viscosity at higher shear rates, with all values being below 13 cP.

TABLE 12

Viscosity of an exemplary OMS646 formulation measured at different shear rates

| Formulation | Temperature (° C.) | Shear Rate (1/s) | Viscosity (cP) |
|---|---|---|---|
| 185 mg/mL OMS646 | 25.0 | 103000 | 12.2 |
| 20 mM Citrate | 25.0 | 156000 | 11.5 |
| 200 mM Arginine | 25.0 | 211000 | 11.0 |
| 0.01% Polysorbate 80 | | | |
| pH 5.8 | | | |

It was determined that dosing human subjects with the exemplary 185 mg/mL OMS646 formulation described in this example (both by subcutaneous injection and intravenous administration after dilution) resulted in sustained and high degrees of lectin pathway inhibition.

While the preferred embodiment of the invention has been illustrated and described, it will be appreciated that various changes to the disclosed formulations and methods can be made therein without departing from the spirit and scope of the invention. It is therefore intended that the scope of letters patent granted hereon be limited only by the definitions of the appended claims.

In accordance with the foregoing, the invention features the following embodiments.

1. A stable pharmaceutical formulation suitable for parenteral administration to a mammalian subject, comprising:
   (a) an aqueous solution comprising a buffer system having a pH of 5.0 to 7.0; and
   (b) a monoclonal antibody or fragment thereof that specifically binds to human MASP-2 at a concentration of about 50 mg/mL to about 250 mg/mL, wherein said antibody or fragment thereof comprises (i) a heavy chain variable region comprising CDR-H1, CDR-H2 and CDR-H3 of SEQ ID NO:2 and (ii) a light chain variable region comprising CDR-L1, CDR-L2 and CDR-L3 of SEQ ID NO:3, or a variant thereof comprising a heavy chain variable region having at least 95% identity to SEQ ID NO:2 and a light chain variable region having at least 95% identity to SEQ ID NO:3;
   wherein the formulation has a viscosity of between 2 and 50 centipoise (cP), and wherein the formulation is stable when stored at between 2° C. and 8° C. for at least one month.

2. The pharmaceutical formulation of paragraph 1, wherein the concentration of the antibody in the formulation is from about 100 mg/mL to about 225 mg/mL.

3. The pharmaceutical formulation of paragraph 1, wherein the concentration of the antibody in the formulation is from about 150 mg/mL to about 200 mg/mL.

4. The pharmaceutical formulation of paragraph 1, wherein the concentration of the antibody in the formulation is from about or about 175 mg/mL to about 195 mg/mL.

5. The pharmaceutical formulation of paragraph 1 or paragraph 2, wherein the viscosity of the formulation is from about 2 cP to about 40 cP.

6. The pharmaceutical formulation of paragraph 1 or paragraph 2, wherein the viscosity of the formulation is from about 2 cP to about 30 cP.

7. The pharmaceutical formulation of paragraph 1 or paragraph 2, wherein the viscosity of the formulation is from about 2 cP to about 25 cP.

8. The pharmaceutical formulation of paragraph 1 or paragraph 2, wherein the viscosity of the formulation is from about 2 cP to about 20 cP.

9. The pharmaceutical formulation of paragraph 1 or paragraph 2, wherein the viscosity of the formulation is from about 2 cP to about 18 cP.

10. The pharmaceutical formulation of any one of paragraphs 1-9, wherein the buffer system comprises at least one pharmaceutically acceptable buffering agent having an acid dissociation constant within 2 pH units of the formulation pH.

11. The pharmaceutical formulation of any one of paragraphs 1-10, wherein the buffer system comprises at least one buffering agent selected from the group consisting of succinate, histidine and citrate.

12. The pharmaceutical formulation of paragraph 11, wherein the at least one buffering agent is histidine or citrate.

13. The pharmaceutical formulation of any one of paragraphs 1-12, wherein the at least one buffering agent is citrate.

14. The pharmaceutical formulation of paragraph 13, wherein the at least one buffering agent is sodium citrate.

15. The pharmaceutical formulation of any one of paragraphs 1-12, wherein the at least one buffering agent is histidine.

16. The pharmaceutical formulation of paragraph 15, wherein the at least one buffering agent is L-histidine.

17. The pharmaceutical formulation of paragraph 13, wherein citrate is present in the solution at a concentration of 10 mM to 50 mM.

18. The pharmaceutical formulation of paragraph 15, wherein histidine is present in the solution at a concentration of 10 mM to 50 mM.

19. The pharmaceutical formulation of any one of paragraphs 1-18, wherein the pharmaceutical formulation further comprises at least one excipient selected from the group consisting of a protein, an amino acid, a sugar, a polyol, a salt, a fatty acid and a phospholipid.

20. The pharmaceutical formulation of paragraph 19, wherein the at least one excipient is a tonicity modifying agent in a sufficient amount for the formulation to be hypertonic.

21. The pharmaceutical formulation of paragraph 20, wherein the tonicity modifying agent selected from the group consisting of an amino acid with a charged side chain, a sugar or other polyol and a salt.

22. The pharmaceutical formulation of paragraph 21, wherein the tonicity modifying agent is a sugar or other polyol and is selected from the group consisting of sucrose, trehalose, mannitol and sorbitol.

23. The pharmaceutical formulation of paragraph 21, wherein the tonicity modifying agent is a salt selected from the group consisting of NaCl or a salt of an amino acid.

24. The pharmaceutical formulation of paragraph 21, wherein the tonicity modifying agent is an amino acid with a charged side chain.

25. The pharmaceutical formulation of paragraph 24, wherein the amino acid with a charged side chain is present in the formulation at a concentration of from about 150 mM to about 300 mM.

26. The pharmaceutical formulation of paragraph 24 or 25, wherein the tonicity modifying agent is an amino acid with a negatively charged side chain.

27. The pharmaceutical formulation of paragraph 24 or 25, wherein the tonicity modifying agent excipient is an amino acid with a positively charged side chain.

28. The pharmaceutical formulation of paragraph 26, wherein the tonicity modifying agent is glutamate.

29. The pharmaceutical formulation of paragraph 27, wherein the tonicity modifying agent is arginine.

30. The pharmaceutical formulation of paragraph 29, wherein the tonicity agent is L-arginine HCl.

31. The pharmaceutical formulation of paragraph 29, wherein arginine is present in the solution at a hypertonic level of from 200 mM to 300 mM.

32. The pharmaceutical formulation of paragraph 17, wherein the solution comprises about 20 mM citrate and has a pH from about 5.5 to about 6.5.

33. The pharmaceutical formulation of paragraph 32, wherein the solution further comprises arginine at a concentration of about 200 mM.

34. The pharmaceutical formulation of paragraph 18, wherein the solution comprises about 20 mM histidine and has a pH from about 5.5 to about 6.5.

35. The pharmaceutical formulation of paragraph 34, wherein the solution further comprises arginine at a concentration of about 200 mM.

36. The pharmaceutical formulation of any one of paragraphs 1-35 wherein the solution further comprises a surfactant at a concentration from about 0.001% (w/v) and about 0.1% (w/v).

37. The pharmaceutical formulation of paragraph 36, wherein the surfactant is a nonionic surfactant.

38. The pharmaceutical formulation of paragraph 37, wherein the surfactant is a polysorbate or a poloxamer.

39. The pharmaceutical formulation of paragraph 38, wherein the surfactant is polysorbate 80.

40. The pharmaceutical formulation of any one of paragraphs 1-39, wherein the formulation is stable when stored at between 2° C. and 8° C. for at least 6 months.

41. The pharmaceutical formulation of any one of paragraphs 1-39, wherein the formulation is stable when stored at between 2° C. and 8° C. for at least 12 months.

42. The pharmaceutical formulation of any one of paragraphs 1-39, wherein the viscosity is less than about 25 cP.

43. The pharmaceutical formulation of any one of paragraphs 1-39, wherein the viscosity is less than about 20 cP.

44. The pharmaceutical formulation of any one of paragraphs 1-39, wherein the viscosity is less than about 18 cP.

45. The pharmaceutical formulation of any one of paragraphs 1-39, wherein the injection glide force of the formulation is about 25 Newton or less when injected through a 27GA 1.25" needle at room temperature.

46. The pharmaceutical formulation of any one of paragraphs 1-39, wherein the injection glide force of the formulation is about 20 Newton or less when injected through a 25GA 1" needle at room temperature.

47. The pharmaceutical formulation of paragraph 1, wherein the formulation comprises:
about 20 mM sodium citrate, about 200 mM L-arginine HCl, wherein the concentration of the antibody in the formulation is from about 175 mg/mL to about 195 mg/mL, and wherein the viscosity is less than about 25 cP.

48. The pharmaceutical formulation of paragraph 47, wherein the formulation further comprises from 0.001% w/v to 0.05% w/v polysorbate 80.

49. The pharmaceutical formulation of paragraph 1, wherein the formulation comprises:
about 20 mM L-histidine, about 200 mM L-arginine HCl, wherein the concentration of the antibody in the formulation is from about 175 mg/mL to about 195 mg/mL, and wherein the viscosity is less than about 25 cP.

50. The pharmaceutical formulation of paragraph 49, wherein the formulation further comprises from 0.001% w/v to 0.05% w/v polysorbate 80.

51. The pharmaceutical formulation of any one of paragraphs 1-50, wherein the formulation is sterile.

52. The pharmaceutical formulation of any one of paragraphs 1-50, wherein the monoclonal antibody is a full length monoclonal antibody.

53. The pharmaceutical formulation of paragraph 52, wherein the antibody is a human IgG4 full length antibody.

54. The pharmaceutical formulation of paragraph 53, wherein the IgG4 comprises a mutation in the hinge region.

55. The pharmaceutical formulation of any one of paragraphs 1-54, wherein the formulation does not include sucrose or sorbitol.

56. The pharmaceutical formulation of any one of paragraphs 1-54, wherein the formulation does not include $CaCl_2$.

57. The pharmaceutical formulation of any one of paragraphs 1-54, wherein the formulation does not include $MgCl_2$.

58. The pharmaceutical formulation of any one of paragraphs 1-54, wherein the formulation does not include $CaCl_2$ and wherein the formulation does not include $MgCl_2$.

59. The pharmaceutical formulation of any of paragraphs 1-54, wherein the formulation does not include a divalent cation additive.

60. The pharmaceutical formulation of any one of paragraphs 1-59, wherein the concentration of the antibody is about 185 mg/mL.

61. The pharmaceutical formulation of any one of paragraphs 1-60, wherein the formulation further comprises a hyaluronidase enzyme in an amount effective to increase the dispersion and/or absorption of the antibody following subcutaneous administration.

62. The pharmaceutical formulation of paragraph 61, wherein the formulation comprises from about 100 U/mL to about 20,000 U/mL of said hyaluronidase enzyme.

63. The pharmaceutical formulation of paragraph 1, wherein the formulation comprises:
(a) polysorbate 80 at a concentration from about 0.01 to about 0.08% w/v;
(b) L-arginine HCl at a concentration from about 150 mM to about 200 mM;
(c) sodium citrate at a concentration from about 10 mM to about 50 mM; and
(d) about 150 mg/mL to about 200 mg/mL of the antibody.

The pharmaceutical formulation of paragraph 1, wherein the formulation comprises:
(a) polysorbate 80 at a concentration from about 0.01 to about 0.08% w/v;
(b) L-arginine HCl at a concentration from about 150 mM to about 200 mM;
(c) L-histidine at a concentration from about 10 mM to about 50 mM; and
(d) about 150 mg/mL to about 200 mg/mL of the antibody.

65. The pharmaceutical formulation of paragraph 1, wherein the formulation comprises:
(a) polysorbate 80 at a concentration of about 0.01 w/v;
(b) L-arginine HCl at a concentration of about 200 mM;
(c) sodium citrate at a concentration of about 20 mM; and
(d) about 175 mg/mL to about 195 mg/mL of the antibody.

66. The pharmaceutical formulation of paragraph 1, wherein the formulation comprises:
(a) polysorbate 80 at a concentration of about 0.01% w/v;
(b) L-arginine HCl at a concentration of about 200 mM;
(c) L-histidine at a concentration of about 20 mM; and
(d) about 175 mg/mL to about 195 mg/mL of the antibody.

67. The pharmaceutical formulation of paragraph 1, wherein the formulation comprises:
(a) polysorbate 80 at a concentration of about 0.01% w/v;
(b) L-arginine HCl at a concentration of about 200 mM;
(c) sodium citrate at a concentration of about 20 mM; and
(d) about 175 mg/mL to about 195 mg/mL of the antibody.

68. The pharmaceutical formulation of paragraph 1, wherein the formulation comprises:
(a) polysorbate 80 at a concentration of about 0.01% w/v;
(b) L-arginine HCl at a concentration of about 200 mM;
(c) L-histidine at a concentration of about 20 mM; and
(d) about 175 mg/mL to about 195 mg/mL of the antibody.

69. The pharmaceutical formulation of any of paragraphs 63 to 68 wherein the formulation further comprises from about 100 U/mL to about 20,000 U/mL of a hyaluronidase enzyme effective to increase the dispersion and/or absorption of the antibody following subcutaneous administration.

70. A stable aqueous pharmaceutical formulation suitable for parenteral administration to a mammalian subject, the formulation consisting essentially of:
(a) polysorbate 80 at a concentration from about 0.01 to about 0.08% w/v;
(b) L-arginine HCl at a concentration from about 150 mM to about 200 mM;
(c) sodium citrate at a concentration from about 10 mM to about 50 mM; and
(d) a monoclonal antibody or fragment thereof that specifically binds to human MASP-2 at a concentration of about 150 mg/mL to about 200 mg/mL, wherein said antibody or fragment thereof comprises (i) a heavy chain variable region comprising CDR-H1, CDR-H2 and CDR-H3 of SEQ ID NO:2 and (ii) a light chain variable region comprising CDR-L1, CDR-L2 and CDR-L3 of SEQ ID NO:3, or a variant thereof comprising a heavy chain variable region having at least 95% identity to SEQ ID NO:2 and a light chain variable region having at least 95% identity to SEQ ID NO:3;
wherein the formulation has a pH from about 5.0 to about 7.0, a viscosity of between 2 and 50 centipoise (cP), and wherein the formulation is stable when stored at between 2° C. and 8° C. for at least one month.

71. A stable aqueous pharmaceutical formulation suitable for parenteral administration to a mammalian subject, the formulation consisting essentially of:
(a) polysorbate 80 at a concentration from about 0.01 to about 0.08% w/v;
(b) L-arginine HCl at a concentration from about 150 mM to about 200 mM;
(c) L-histidine at a concentration from about 10 mM to about 50 mM; and
(d) a monoclonal antibody or fragment thereof that specifically binds to human MASP-2 at a concentration of about 150 mg/mL to about 200 mg/mL, wherein said antibody or fragment thereof comprises (i) a heavy chain variable region comprising CDR-H1, CDR-H2 and CDR-H3 of SEQ ID NO:2 and (ii) a light chain variable region comprising CDR-L1, CDR-L2 and CDR-L3 of SEQ ID NO:3, or a variant thereof comprising a heavy chain variable region having at least 95% identity to SEQ ID NO:2 and a light chain variable region having at least 95% identity to SEQ ID NO:3;
wherein the formulation has a pH from about 5.0 to about 7.0, a viscosity of between 2 and 50 centipoise (cP), and wherein the formulation is stable when stored at between 2° C. and 8° C. for at least one month.

72. The formulation of any of paragraphs 1-71 wherein the antibody or fragment thereof comprises a heavy chain variable region comprising the amino acid sequence set forth in SEQ ID NO:2 and a light chain variable region comprising the amino acid sequence set forth in SEQ ID NO:3.

73. A sealed container containing a formulation according to any one of paragraphs 1-72.

74. A subcutaneous administration device containing the formulation of any one of paragraphs 1-72 therein.

75. A kit comprising a pre-filled container comprising the pharmaceutical formulation comprising the MASP-2 antibody of any of paragraphs 1-72 and instructions for use of the formulation.

76. The kit of paragraph 75 wherein the pre-filled container is selected from the group consisting of: a syringe, a pen injector, a sealed vial, an auto-injector and a pump device (e.g., an on-body patch pump or a tethered pump).

77. A kit comprising:
(a) a first pre-filled container comprising the pharmaceutical formulation comprising the MASP-2 antibody of any of paragraphs 1-60 or paragraphs 63-72;
(b) a second pre-filled container comprising an amount of hyaluronidase enzyme effective to increase the dispersion and/or absorption of the MASP-2 antibody following subcutaneous administration; and
(c) instructions for use.

78. The kit of paragraph 77 wherein at least one of the first or second pre-filled container(s) is selected from the group consisting of: a syringe, a pen injector, a sealed vial, an auto-injector and a pump device (e.g., an on-body patch pump or a tethered pump).

79. A pharmaceutical unit dosage form suitable for parental administration to a human, comprising a formulation according to any of paragraphs 1-72 in a suitable container.

80. A method of treating a subject suffering from a disease or disorder amenable to treatment with a MASP-2 inhibitory antibody comprising administering a formulation of any one of paragraphs 1-72 to the subject in need thereof.

81. The method of paragraph 80, wherein the formulation is administered subcutaneously to the subject.

82. The method of paragraph 80, wherein the method further comprises administering to the subject a hyaluronidase enzyme in an amount effective to increase the dispersion and/or absorption of the antibody.

83. The method of paragraph 82, wherein the hyaluronidase enzyme is administered simultaneously with the formulation comprising the MASP-2 inhibitory antibody.

84. The method of paragraph 82 or 83, wherein the formulation comprises the MASP-2 inhibitory antibody and the hyaluronidase enzyme.

85. The method of paragraph 82, wherein the hyaluronidase enzyme is administered to the subject prior to the formulation comprising the MASP-2 inhibitory antibody.

86. The method of paragraph 82, wherein the hyaluronidase enzyme is administered to the subject after the formulation comprising the MASP-2 inhibitory antibody.

87 The method of paragraph 80, wherein the formulation is administered via a pre-filled syringe containing the formulation therein.

88. A method of inhibiting MASP-2 dependent complement activation in a subject suffering from, or at risk of developing, a complement-associated disease or disorder comprising administering a formulation of any one of paragraphs 1-72 to the subject in need thereof 89. The method of paragraph 88, wherein the formulation is administered subcutaneously to the subject.

90. The method of paragraph 79, wherein the formulation is administered via a pre-filled syringe containing the formulation therein.

91. The method of paragraph 88, wherein the subject is suffering from or at risk of developing a complement-associated disease or disorder selected from the group consisting of a thrombotic microangiopathy (TMA), a renal condition, an inflammatory reaction resulting from tissue or organ transplantation, an ischemia reperfusion injury, a complication associated with diabetes, a cardiovascular disease or disorder, an inflammatory gastrointestinal disorder, a pulmonary disorder, an ophthalmic disease or disorder, and disseminated intravascular coagulation.

92. The method of paragraph 91, wherein the thrombotic microangiopathy is atypical hemolytic syndrome (aHUS).

93. The method of paragraph 91, wherein the thrombotic microangiopathy is associated with hematopoietic stem cell transplant.

94. The method of paragraph 91, wherein the renal condition is IgA nephropathy.

95. The method of paragraph 91, wherein the renal condition is lupus nephritis.

96. A method of inhibiting MASP-2 dependent complement activation in a subject suffering from, or at risk of developing, a complement-associated disease or disorder comprising diluting a formulation of any one of paragraphs 1-72 into a pharmaceutically-acceptable diluent and administering the diluted formulation systemically to the subject in need thereof 97. The method of paragraph 96, wherein the diluted formulation is administered intravenously to the subject.

98. The method of paragraph 96, wherein the subject is suffering from or at risk of developing a complement-associated disease or disorder selected from the group consisting of a thrombotic microangiopathy (TMA), a renal condition, an inflammatory reaction resulting from tissue or organ transplantation, an ischemia reperfusion injury, a complication associated with diabetes, a cardiovascular disease or disorder, an inflammatory gastrointestinal disorder, a pulmonary disorder, an ophthalmic disease or disorder, and disseminated intravascular coagulation.

99. The method of paragraph 98, wherein the thrombotic microangiopathy is atypical hemolytic syndrome (aHUS).

100. The method of paragraph 98, wherein the thrombotic microangiopathy is associated with hematopoietic stem cell transplant.

101. The method of paragraph 98, wherein the renal condition is IgA nephropathy.

102. The method of paragraph 98, wherein the renal condition is lupus nephritis.

103. A pharmaceutical composition for use in treating a patient suffering from, or at risk for developing a MASP-2-dependent complement-associated disease or disorder, wherein the composition is a sterile, single-use dosage form comprising from about 350 mg to about 400 mg of MASP-2 inhibitory antibody, wherein the composition comprises about 1.8 mL to about 2.2 mL of a 185 mg/mL antibody formulation, wherein the antibody comprises (i) a heavy chain variable region comprising the amino acid sequence set forth in SEQ ID NO:2 and (ii) a light chain variable region comprising the amino acid sequence set forth in SEQ ID NO:3, and wherein the composition is stable when stored at between 2° C. and 8° C. for at least six months.

104. The composition of paragraph 103, wherein composition comprises a buffer system having a pH of 5.0 to 7.0.

105. The composition of paragraph 104, wherein the buffer system comprises at least one pharmaceutically acceptable buffering agent selected from the group consisting of succinate, histidine and citrate.

106. The composition of paragraph 103, wherein the composition comprises from 1.8 mL to 2.2 mL of a 185 mg/mL MASP-2 inhibitory antibody formulation of any one of paragraphs 1-72.

107. The composition of any one of paragraphs 103-107, wherein the MASP-2 dependent complement-associated disease or disorder is aHUS.

108. The composition of any one of paragraphs 103-107, wherein the MASP-2 dependent complement-associated disease or disorder is HSCT-TMA.

109. The composition of any one of paragraphs 103-107, wherein the MASP-2 dependent complement-associated disease or disorder is IgAN.

110. The composition of any one of paragraphs 103-107, wherein the MASP-2 dependent complement-associated disease or disorder is Lupus Nephritis (LN).

While the preferred embodiment of the invention has been illustrated and described, it will be appreciated that various changes can be made therein without departing from the spirit and scope of the invention.

The invention claimed is:

1. A stable aqueous pharmaceutical formulation suitable for subcutaneous administration to a mammalian subject, consisting of:
   (a) a sodium citrate or histidine buffer system having a pH of 5.5 to 6.5, wherein the sodium citrate or histidine is at a concentration of from 10 mM to 50 mM;
   (b) a monoclonal antibody that specifically binds to human Mannan-binding lectin-associated serine protease-2 (MASP-2) at a concentration of from 150 mg/mL to 200 mg/mL, wherein said antibody is a human IgG4 antibody comprising (i) a heavy chain variable region comprising the amino acid sequence set forth in SEQ ID NO:2, and (ii) a light chain variable region comprising the amino acid sequence set forth in SEQ ID NO:3;
   (c) arginine at a concentration of from 200 mM to 300 mM, wherein the arginine is present in a sufficient amount for the formulation to be hypertonic; and
   (d) polysorbate 80 (PS-80) at a concentration from 0.001% (w/v) to 0.1% (w/v);
   wherein the formulation has a viscosity suitable for subcutaneous administration of between 2 and 25 centipoise (cP) as measured at about 25° C. with a shear rate in the range of 100,000 to 250,000 1/sec, and wherein the formulation has at least 95% monomeric antibody as determined by size exclusion chromatography (SEC) after storage at between 2° C. and 8° C. for at least six months.

2. The pharmaceutical formulation of claim 1, wherein the concentration of the antibody in the formulation is from 175 mg/mL to 195 mg/mL.

3. The pharmaceutical formulation of claim 1, wherein the viscosity of the formulation is from 2 cP to 20 cP.

4. The pharmaceutical formulation of claim 1, wherein the at least one buffering agent is sodium citrate.

5. The pharmaceutical formulation of claim 1, wherein the arginine is L-arginine HCl.

6. The pharmaceutical formulation of claim 1, wherein the solution comprises about 20 mM citrate.

7. The pharmaceutical formulation of claim 6, wherein the solution comprises arginine at a concentration of 200 mM.

8. The pharmaceutical formulation of claim 1, wherein the formulation is stable when stored between 2° C. and 8° C. for at least 12 months.

9. The pharmaceutical formulation of claim 1, wherein the viscosity is less than about 20 cP.

10. The pharmaceutical formulation of claim 1, wherein the injection glide force of the formulation is about 25 Newton or less when injected through a 27GA 1.25" needle at room temperature.

11. The pharmaceutical formulation of claim 1, wherein the injection glide force of the formulation is about 20 Newton or less when injected through a 25GA 1" needle at room temperature.

12. The pharmaceutical formulation of claim 1, wherein the formulation comprises:
   20 mM sodium citrate, 200 mM L-arginine HCl, wherein the concentration of the antibody in the formulation is from 175 mg/mL to 195 mg/mL, and wherein the viscosity is less than 25 cP.

13. The pharmaceutical formulation of claim 12, wherein the formulation comprises from 0.001% w/v to 0.05% w/v polysorbate 80.

14. The pharmaceutical formulation of claim 1, wherein the formulation is sterile.

15. The pharmaceutical formulation of claim 1, wherein the IgG4 comprises a S228P mutation in the hinge region.

16. The pharmaceutical formulation of claim 1, wherein the concentration of the antibody is about 185 mg/mL.

17. The pharmaceutical formulation of claim 1, wherein the formulation comprises:
   (a) polysorbate 80 at a concentration from 0.01 to 0.08% w/v;
   (b) L-arginine HCl at a concentration of 200 mM;
   (c) sodium citrate at a concentration from 10 mM to 50 mM; and
   (d) 150 mg/mL to 200 mg/mL of the antibody.

18. The pharmaceutical formulation of claim 1, wherein the formulation comprises:
(a) polysorbate 80 at a concentration of about 0.01 w/v;
(b) L-arginine HCl at a concentration of 200 mM;
(c) sodium citrate at a concentration of 20 mM; and
(d) 175 mg/mL to 195 mg/mL of the antibody.

19. A stable aqueous pharmaceutical formulation suitable for parenteral administration to a mammalian subject, the formulation consisting of:
(a) polysorbate 80 at a concentration from 0.01 to 0.08% w/v;
(b) L-arginine HCl at a concentration of 200 mM;
(c) sodium citrate at a concentration of 20 mM; and
(d) a monoclonal antibody that specifically binds to human Mannan-binding lectin-associated serine protease-2 (MASP-2) at a concentration of from 175 mg/mL to 195 mg/mL, wherein said antibody is a human IgG4 isotype antibody comprising (i) a heavy chain variable region comprising the amino acid sequence set forth in SEQ ID NO:2, and (ii) a light chain variable region comprising the amino acid sequence set forth in SEQ ID NO:3;
wherein the formulation has a pH from about 5.5 to about 6.5, a viscosity of between 2 and 25 centipoise (cP) as measured at about 25° C. with a shear rate in the range of 100,000 to 250,000 1/sec, and wherein the formulation has at least 95% monomeric antibody as determined by size exclusion chromatography (SEC) after storage at between 2° C. and 8° C. for at least six months.

20. A sealed container containing a formulation according to claim 1 or 19.

21. A subcutaneous administration device containing the formulation of claim 1 or 19 therein.

22. A kit comprising a pre-filled container comprising the pharmaceutical formulation consisting the MASP-2 antibody of claim 1 or 19 and instructions for use of the formulation.

23. The kit of claim 22 wherein the pre-filled container is selected from the group consisting of: a syringe, a pen injector, a sealed vial, an auto-injector and a pump device.

24. The kit of claim 22, wherein the pre-filled container is a sealed vial.

25. The kit of claim 22, wherein the kit further comprises at least one injection device suitable for administering the formulation in the sealed vial to a human subject.

26. A pharmaceutical unit dosage form suitable for parental administration to a human, comprising a formulation according to claim 1 or 19 in a suitable container.

27. The pharmaceutical formulation of claim 1, wherein the monoclonal antibody is a tetramer consisting of two identical heavy chains having the amino acid sequence set forth in SEQ ID NO:4 and two identical light chains having the amino acid sequence set forth in SEQ ID NO:5.

28. The pharmaceutical formulation of claim 19, wherein the monoclonal antibody is a tetramer consisting of two identical heavy chains having the amino acid sequence set forth in SEQ ID NO:4 and two identical light chains having the amino acid sequence set forth in SEQ ID NO:5.

* * * * *

UNITED STATES PATENT AND TRADEMARK OFFICE
CERTIFICATE OF CORRECTION

PATENT NO. : 11,628,217 B2
APPLICATION NO. : 15/691266
DATED : April 18, 2023
INVENTOR(S) : Gregory A. Demopulos It is certified that error appears in the above-identified patent and that said Letters Patent is hereby corrected as shown below:

On the Title Page

On page 2, in Column 1, item (56), under OTHER PUBLICATIONS, Line 21, delete "PharmaSciTech" and insert -- PharmSciTech --, therefor.

On page 2, in Column 2, item (56), under OTHER PUBLICATIONS, Line 8, delete "kinectics,"" and insert -- kinetics," --, therefor.

On page 2, in Column 2, item (56), under OTHER PUBLICATIONS, Line 10, delete ""Anibody" and insert -- "Antibody --, therefor.

On page 2, in Column 2, item (56), under OTHER PUBLICATIONS, Line 23, delete "Pharmecutical" and insert -- Pharmaceutical --, therefor.

In the Specification

In Column 2, Line 44, delete "US 2015/0166675;" and insert -- US2015/0166675; --, therefor.

In Column 4, Line 55, delete "NO:1 human" and insert -- NO:1: human --, therefor.

In Column 4, Line 55, delete "(mature)" and insert -- (mature). --, therefor.

In Column 4, Line 57, delete "polypeptide" and insert -- polypeptide. --, therefor.

In Column 4, Line 59, delete "polypeptide" and insert -- polypeptide. --, therefor.

In Column 4, Line 61, delete "polypeptide" and insert -- polypeptide. --, therefor.

In Column 4, Lines 62-63, delete "polypeptide" and insert -- polypeptide. --, therefor.

Signed and Sealed this
Twenty-third Day of May, 2023

Katherine Kelly Vidal
*Director of the United States Patent and Trademark Office*

In Column 4, Line 65, delete "polypeptide" and insert -- polypeptide. --, therefor.

In Column 5, Line 23, delete "3d" and insert -- 3rd --, therefor.

In Column 6, Line 28, delete "F(ab')2," and insert -- F(ab')$_2$, --, therefor.

In Column 6, Line 60, delete "editions." and insert -- editions). --, therefor.

In Column 8, Line 12, delete "mOsmol/" and insert -- mOsm/ --, therefor.

In Column 8, Line 22, delete "asceptic" and insert -- aseptic --, therefor.

In Column 11, Line 61, delete "iii)" and insert -- (iii) --, therefor.

In Column 13, Line 51, delete "MSP-2" and insert -- MASP-2 --, therefor.

In Column 16, Lines 62-63, delete "polyoxyethylensorbitan" and insert -- polyoxyethylenesorbitan --, therefor.

In Columns 17-18, Lines 67 and 1, delete ""Syringeablity,"" and insert -- "Syringeability," --, therefor.

In Column 18, Line 26, delete "(2006)." and insert -- (2006)). --, therefor.

In Column 20, Line 28, delete "1:5000." and insert -- 1:5,000. --, therefor.

In Column 25, Line 32, delete "US 2015/0166675," and insert -- US2015/0166675, --, therefor.

In Column 26, Line 35, delete "hemolytic syndrome" and insert -- hemolytic uremic syndrome --, therefor.

In Column 26, Line 36, delete "hemolytic syndrome," and insert -- hemolytic uremic syndrome, --, therefor.

In Column 26, Line 43, delete "mesangioproliferative" and insert -- mesangialproliferative --, therefor.

In Column 26, Line 59, delete "glomerulonepthritis" and insert -- glomerulonephritis --, therefor.

In Columns 26-27, Lines 67 and 1, delete "orthostatis" and insert -- orthostatic --, therefor.

In Column 27, Lines 21-22, delete "glomerulonepthritis." and insert -- glomerulonephritis. --, therefor.

In Column 27, Line 32, delete "FR," and insert -- I/R, --, therefor.

In Column 27, Line 33, delete "FR" and insert -- I/R --, therefor.

In Column 27, Line 34, delete "FR" and insert -- I/R --, therefor.

In Column 28, Line 10, delete "a extracorporeal" and insert -- an extracorporeal --, therefor.

In Column 28, Line 14, delete "leukopheresis," and insert -- leukapheresis, --, therefor.

In Column 29, Line 32, delete "injury," and insert -- injury), --, therefor.

In Column 29, Line 49, delete "Nepthritis" and insert -- Nephritis --, therefor.

In Column 30, Line 15, delete "thrombodulin)" and insert -- thrombomodulin) --, therefor.

In Column 30, Line 55, delete "an Phase" and insert -- a Phase --, therefor.

In Column 33, Line 26, delete "Ringers" and insert -- Ringer's --, therefor.

In Column 34, Line 28, delete "4)" and insert -- SEQ ID NO:4) --, therefor.

In Column 34, Line 49, delete "(L3)" and insert -- (L3)) --, therefor.

In Column 34, Line 60, delete "QVTLKESGPVLVKPTETLTLTCTVSGESLSRGKMGVSWIRQPPGKALEWL" and insert -- QVTLKESGPVLVKPTETLTLTCTVSGFSLSRGKMGVSWIRQPPGKALEWL --, therefor.

In Column 34, Line 66, delete "CNVDHKPSNTKVDKRVESKYGPPCPPCPAPEFLGGPSVFLEPPKPKDTLM" and insert -- CNVDHKPSNTKVDKRVESKYGPPCPPCPAPEFLGGPSVFLFPPKPKDTLM --, therefor.

In Column 35, Line 12, delete "KQRPSGIPERFSGSNSGNTATLTISGTCQAMDEADYYCQAWDSSTAVEGGG" and insert -- KQRPSGIPERFSGSNSGNTATLTISGTQAMDEADYYCQAWDSSTAVFGGG --, therefor.

In Column 35, Line 14, delete "TKLTVLGQPKAAPSVTLEPPSSEELQANKATLVCLISDFYPGAVTVAWKA" and insert -- TKLTVLGQPKAAPSVTLFPPSSEELQANKATLVCLISDFYPGAVTVAWKA --, therefor.

In Column 35, Line 44, delete "(i)" and insert -- i) --, therefor.

In Column 37, Line 30, delete "UVettes" and insert -- cuvettes --, therefor.

In Column 37, Line 48, delete "UVette" and insert -- cuvette --, therefor.

In Column 39, Line 40, delete "15" and insert -- 15 μm --, therefor.
In Column 43, Line 12, delete "Ca'." and insert -- $Ca^{2+}$. --, therefor.

In Columns 43-44, under Table 3, Line 4, delete "(49.2 Claim)" and insert -- (49.2 cP Claim) --, therefor.

In Column 44, Line 21, delete "Ca'" and insert -- $Ca^{2+}$ --, therefor.

In Column 44, Line 48, delete "Ca'" and insert -- $Ca^{2+}$ --, therefor.

In Column 45, Line 65, delete "pH 5.0" and insert -- pH 5.0; --, therefor.

In Column 46, Line 37, delete "6.0" and insert -- 6.0. --, therefor.

In Column 55, Line 58, delete "Fluorotec" and insert -- Flurotec --, therefor.

In Column 60, Line 53, delete "The" and insert -- 64. The --, therefor.

In Column 63, Line 1, delete "thereof" and insert -- thereof. --, therefor.

In Column 63, Lines 1-3, delete "89. The method of ...... to the subject." and insert the same at Line 2 as a new paragraph.

In Column 63, Line 18, delete "hemolytic syndrome" and insert -- hemolytic uremic syndrome --, therefor.

In Column 63, Line 32, delete "thereof" and insert -- thereof. --, therefor.

In Column 63, Lines 32-34, delete "97. The method of ...... subject." and insert the same at Line 33 as a new paragraph.

In Column 63, Line 46, delete "hemolytic syndrome" and insert -- hemolytic uremic syndrome --, therefor.